(12) United States Patent
Sakaguchi

(10) Patent No.: US 10,179,169 B2
(45) Date of Patent: *Jan. 15, 2019

(54) ADJUVANT COMPOSITION, VACCINE COMPOSITION CONTAINING THE SAME, AND METHOD FOR PRODUCING BOTH OF THEM

(71) Applicant: TERUMO KABUSHIKI KAISHA, Shibuya-ku, Tokyo (JP)

(72) Inventor: Naoki Sakaguchi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/165,718

(22) Filed: May 26, 2016

(65) Prior Publication Data
US 2016/0271246 A1    Sep. 22, 2016

Related U.S. Application Data

(63) Continuation of application No. PCT/JP2014/080380, filed on Nov. 17, 2014.

(30) Foreign Application Priority Data

Nov. 29, 2013 (JP) ................. 2013-248543

(51) Int. Cl.
*A61K 39/39* (2006.01)
*A61K 9/10* (2006.01)
(Continued)

(52) U.S. Cl.
CPC ............. *A61K 39/39* (2013.01); *A61K 9/10* (2013.01); *A61K 9/107* (2013.01); *A61K 47/12* (2013.01);
(Continued)

(58) Field of Classification Search
None
See application file for complete search history.

(56) References Cited

U.S. PATENT DOCUMENTS 4,882,164 A    11/1989  Ferro et al.
9,248,192 B2 *  2/2016  Sakaguchi ............. A61K 47/28
(Continued)

FOREIGN PATENT DOCUMENTS

JP    63-201133 A    8/1988
JP    4-360832 A    12/1992
(Continued)

OTHER PUBLICATIONS

Hafez et al., "Cholestryl hemisuccinate exhibits pH sensitive polymorphic phase behavior", Biochim. Biophys. Acta, 1463, 107-114 (2000).*

(Continued)

*Primary Examiner* — Bethany P Barham
*Assistant Examiner* — Barbara S Frazier
(74) *Attorney, Agent, or Firm* — Buchanan Ingersoll & Rooney PC

(57) ABSTRACT

An adjuvant composition includes a pH-sensitive carrier and a substance with stimulus to activate innate immune system. The adjuvant composition serves as a carrier which is highly safe and capable of efficient induction of CTL.

11 Claims, 23 Drawing Sheets

(51) Int. Cl.
  A61K 9/107    (2006.01)
  A61K 47/12   (2006.01)
  A61K 47/28   (2006.01)
  A61K 39/00   (2006.01)
(52) U.S. Cl.
  CPC .... *A61K 47/28* (2013.01); *A61K 2039/55572* (2013.01)

(56) References Cited

U.S. PATENT DOCUMENTS

| | | | |
|---|---|---|---|
| 2004/0126421 A1* | 7/2004 | Turk | A61K 9/1271 424/450 |
| 2007/0298093 A1 | 12/2007 | Konur et al. | |
| 2013/0323320 A1 | 12/2013 | Sakaguchi | |

FOREIGN PATENT DOCUMENTS

| | | |
|---|---|---|
| JP | 2007-515451 A | 6/2007 |
| WO | 01/21152 A1 | 3/2001 |
| WO | 02/097072 A2 | 12/2002 |
| WO | 2005/113756 A1 | 12/2005 |
| WO | WO 2013/180253 A1 | 12/2013 |

OTHER PUBLICATIONS

Feb. 24, 2015 Written Opinion of the International Searching Authority issued in International Application No. PCT/JP2014/080380.

Park, Yeong-Min et al., "Nanoparticle-Based Vaccine Delivery for Cancer Immunotherapy," Immune Network, Oct. 2013, pp. 177-183, vol. 13, No. 5.

Flanary, Suzanne, "Antigen Delivery with Poly(Propylacrylic Acid) Conjugation Enhances MHC-1 Presentation and T-Cell Activation," NIH Public Access, Feb. 2009, pp. 1-18, Bioconjug Chem.

Yoshizaki, Yuta et al., "pH Otosei Kobunshi Shushoku Liposome no Men'eki Yudo Kino eno Adjuvant Bunshi Donyu no Koka," Dai 35 Kai The Annual Meeting of the Japanese Society for Biomaterials Yokoshu, Nov. 25, 2013, p. 239 (with English language translation).

International Search Report (PCT/ISA/210) dated Feb. 24, 2015, by the Japanese Patent Office as the International Searching Authority for International Application No. PCT/JP2014/080380.

X. Zhao et al., "Immunological Adjuvant Efficacy of Glycyrrhetinic Acid Liposome Against Newcastle Disease Vaccine", Vaccine, Elsevier, Oct. 22, 2011, vol. 29, No. 52, pp. 9611-9617, XP028397080.

J. Kim et al., "18β-Glycyrrhetinic Acid Induces Immunological Adjuvant Activity of Th1 Against Candida Albicans Surface Mannan Extract", Phytomedicine, Elsevier, Aug. 1, 2013, vol. 20, No. 11, pp. 951-955, XP055386214.

S. Rao Chavali et al., "An In Vitro Study of Immunomodulatory Effects of Some Saponins", International Journal of Immunopharmacology, Jan. 1, 1987, vol. 9, No. 6, pp. 675-683, XP023811366.

C. Wu et al., "Protective Effects of Glycyrrhizic Acid and 18β-Glycyrrhetinic Acid Against Cisplatin-Induced Nephrotoxicity in BALB/c Mice ", Journal of Agricultural and Food Chemistry, Feb. 4, 2015, vol. 63, No. 4, pp. 1200-1209, XP055386341.

The extended European Search Report dated Jul. 14, 2017, by the European Patent Office in corresponding European Application No. 14865764.6. (18 pages).

Office Action (Notification of Reasons for Refusal) dated Nov. 13, 2018, by the Japanese Patent Office in corresponding Japanese Patent Application No. 2015-550654 and an English Translation of the Office Action. (6 pages).

* cited by examiner

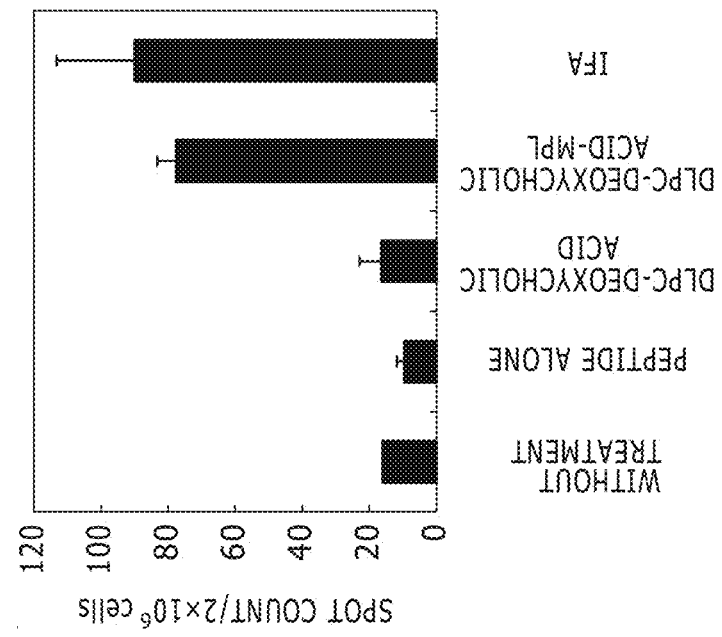

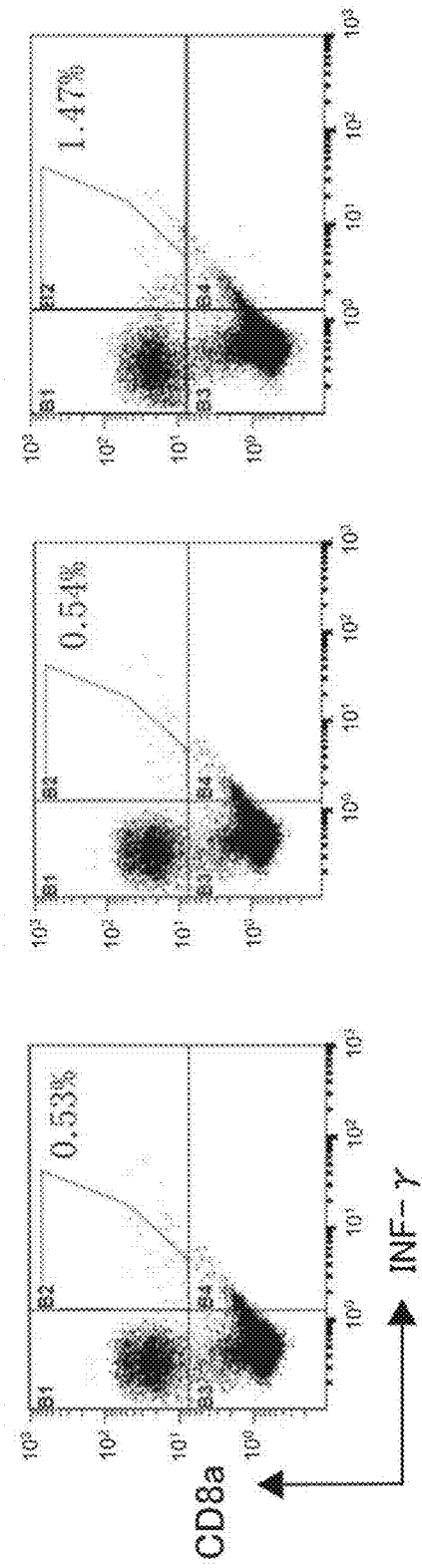

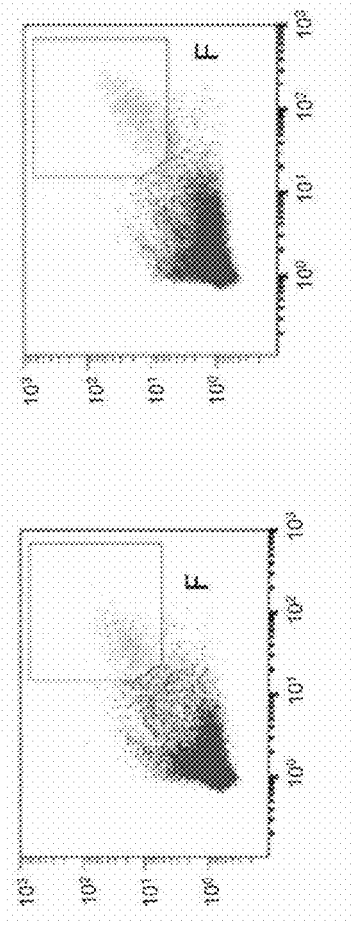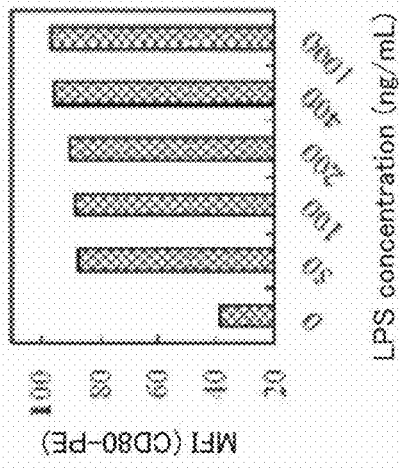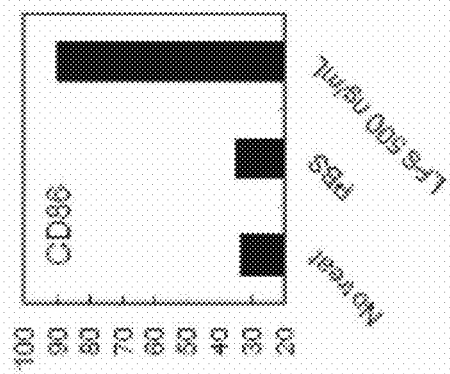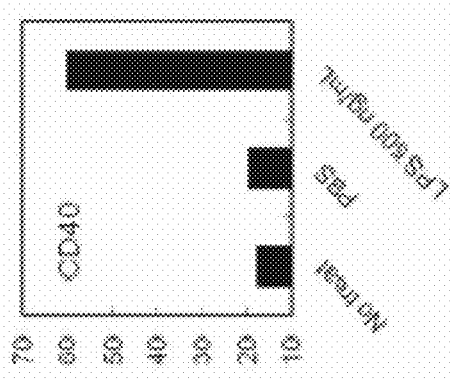

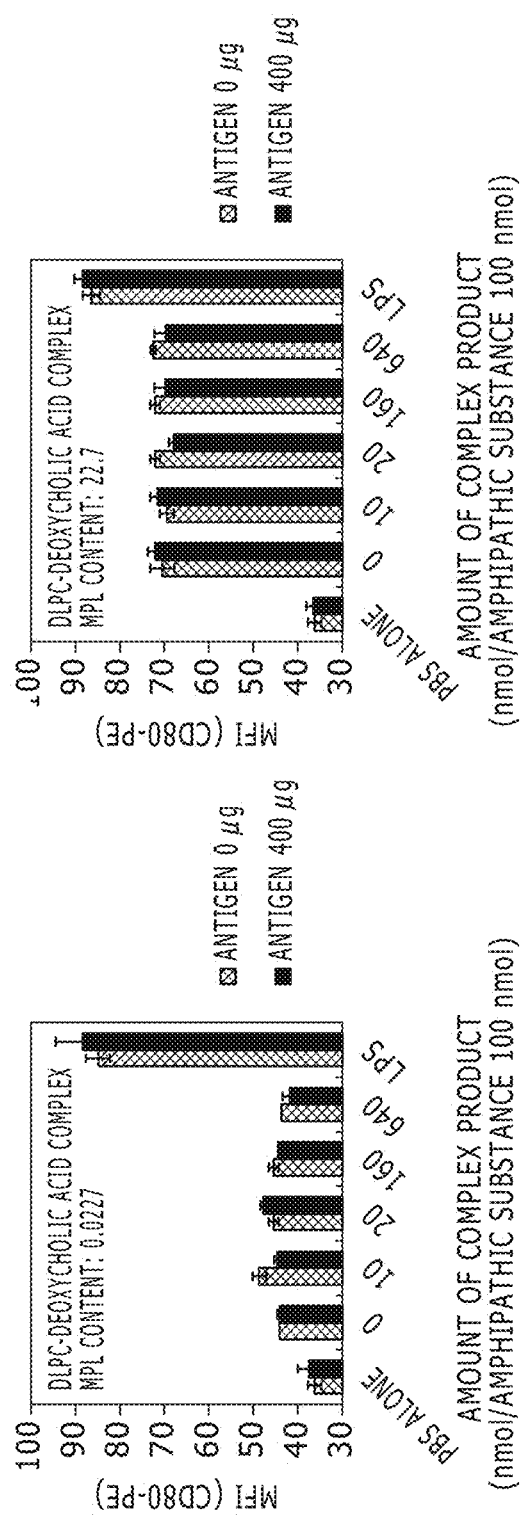

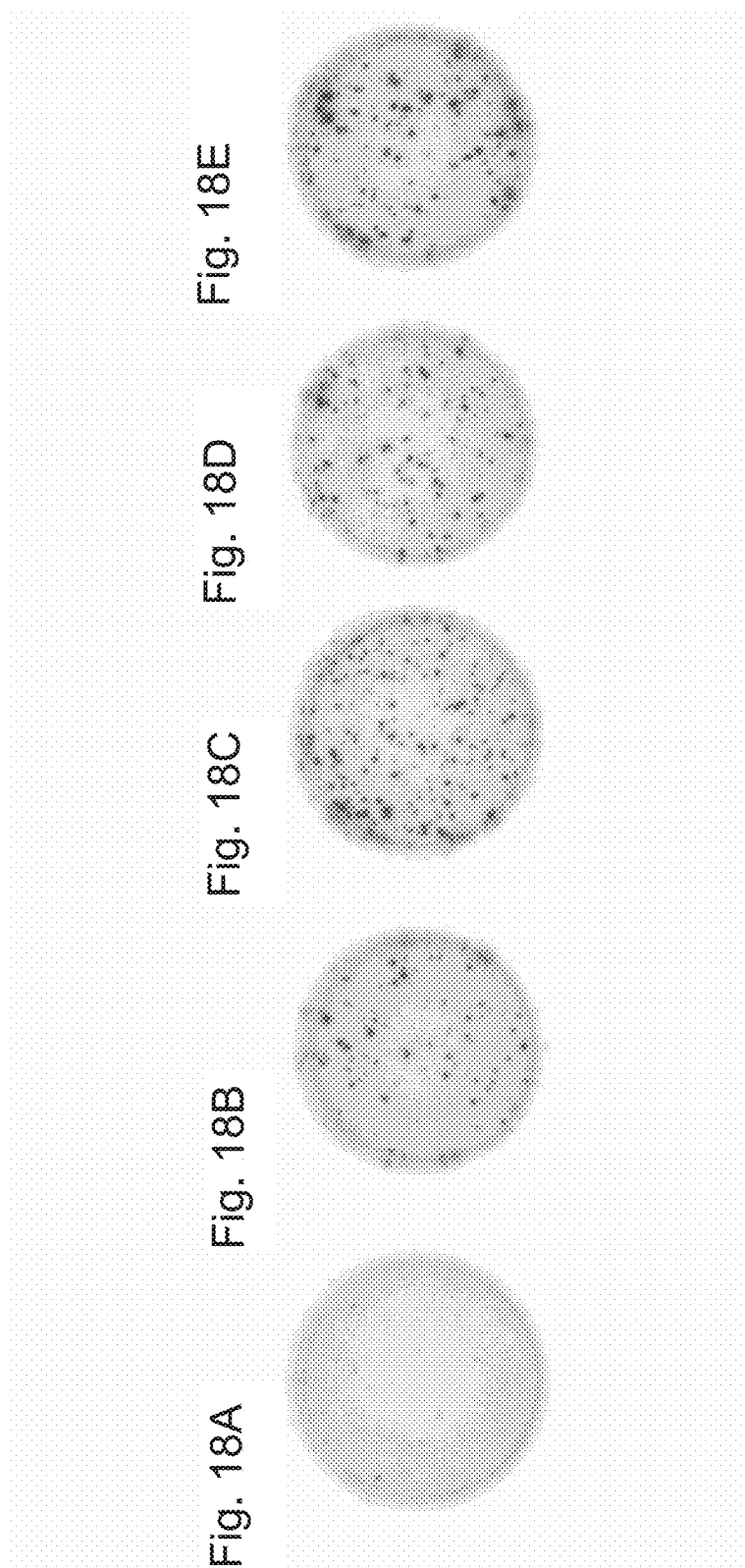

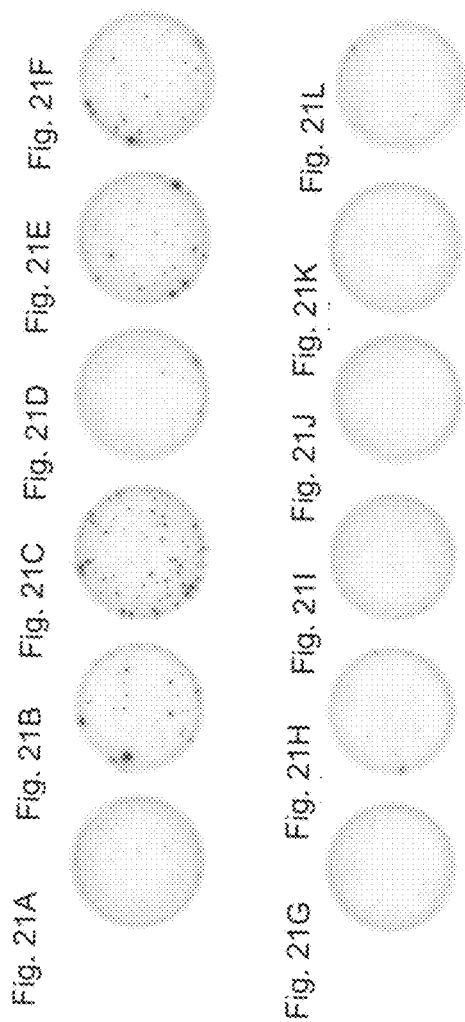

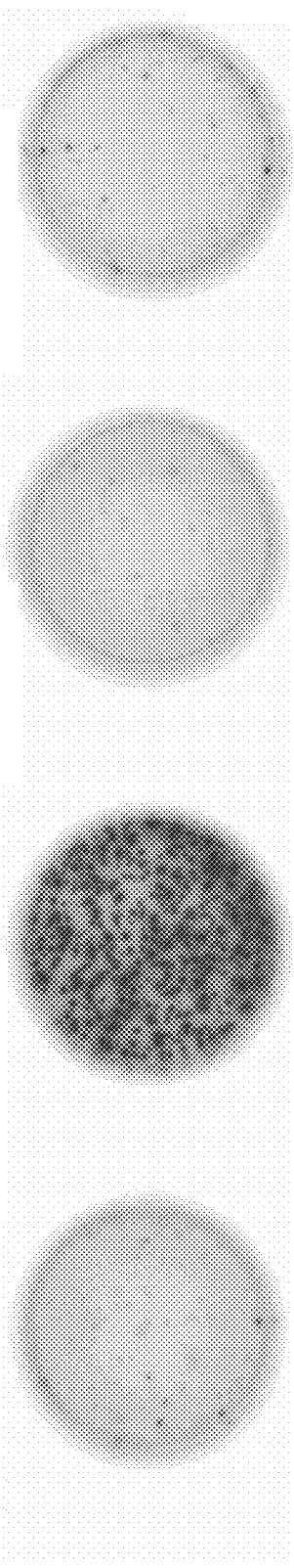

ADJUVANT COMPOSITION, VACCINE COMPOSITION CONTAINING THE SAME, AND METHOD FOR PRODUCING BOTH OF THEM

CROSS-REFERENCES TO RELATED APPLICATIONS

This application is a continuation of International Application No. PCT/JP2014/080380 filed on Nov. 17, 2014, and claims priority to Japanese Patent Application No. 2013-248543, filed Nov. 29, 2013, the entire content of both of which is incorporated herein by reference.

TECHNICAL FIELD

The present disclosure relates to an adjuvant composition, a vaccine composition containing the same, and a method for producing both of them.

BACKGROUND ART

The immune system is defined as a protective mechanism that saves an organism from diseases by eliminating foreign matter, abnormal cells, etc. which might have invaded the organism.

The immune system usually functions through one of two mechanisms—humoral immunity and cell-mediated immunity.

The response of humoral immunity usually expresses itself in the following manner. First, an exogenous antigen such as bacteria which has invaded an organism is captured by antigen presenting cells through endocytosis. Next, it is digested and degraded into peptide fragments by protease in endosomes in the antigen presenting cells. The peptide fragments are loaded on major histocompatibility complex (MHC) Class II molecules. The resulting complex is presented to CD4 positive T cells on the surface of the antigen presenting cells, so that the CD4 positive T cells are activated. Finally, the CD4 positive T cells activated in this manner release cytokine, eventually causing B cells to produce antibodies. The above-mentioned MHC Class II molecules express themselves in macrophages, dendritic cells, activated T cells, B cells, and the like.

By contrast, the response of cell-mediated immunity usually expresses itself in the following manner. First, an endogenous antigen, such as protein, which has been generated in virus-infected cells or cancer cells, is ubiquitinated and then degraded into peptide by proteasome. The peptide resulting from degradation combines with MHC Class I molecules. The resulting complex is presented to CD8 positive T cells on the surface of the antigen presenting cells, so that the CD8 positive T cells are activated. Finally, the activated CD8 positive T cells differentiate into cytotoxic T lymphocytes (CTL). The above-mentioned MHC Class I cells exist on the surface of almost all nucleated cells and blood platelets.

Meanwhile, the CTL responsible for cell-mediated immunity attracts attention because of its ability to eliminate virus-infected cells and cancer cells. Recently, efforts are being made to investigate so-called cross-presentation which induces CTL by exogenous antigens. To be more specific, the exogenous antigen is degraded in endosomes in the antigen presenting cells and then loaded on MHC Class II molecules, as mentioned above. However, the cross-presentation causes even part amount of exogenous antigen to pass through the cell membrane or endosome membrane so that it transfers to the cytosol. The exogenous antigen which has thus been transferred to the cytosol functions as an endogenous antigen, thereby eventually is loaded on MHC Class I molecules to induce CTL.

The cross-presentation requires that the exogenous antigen passes through the endosome membrane. This is being investigated extensively. For example, Non-Patent Document 1 describes that pH-sensitive poly(propylacrylic acid) (PPAA) conjugates efficiently transport the antigen to the cytosol. Also, Non-Patent Document 2 describes the vaccine delivery by nano-particles for cancer immune therapy.

Non-Patent Documents

Non-Patent Document 1: Bioconjug Chem. 2009 Feb. 20(2): 241-248

Non-Patent Document 2: Immune Netw. 2013 Oct. 13(5) 177-183

SUMMARY

There is a strong desire to realize the induction of CTL responsible for cell-mediated immunity from the standpoint of developing new vaccines for therapy. From this point of view, efforts are being made toward the search and improvement of adjuvant molecules. However, satisfactory effects for the induction of CTL remain desirable.

Some research has been conducted, with attention paid to the cross-presentation, to realize strong induction of CTL. However, such research is apprehensive about safety because it often relies on new synthetic materials or virus-derived components.

Thus, the present disclosure was undertaken to provide a new carrier which is safe and effectively induces CTL.

The present inventors conducted extensive research, which has led to a finding that the above-mentioned problems are solved if a pH-sensitive carrier is used in combination with a substance with stimulus to activate innate immune system. This finding is the basis of the present disclosure.

Thus, the present disclosure has solved the above-mentioned problems owing to the compositions and methods defined below as (1)-(9).

(1) An adjuvant composition including a pH-sensitive carrier and a substance with stimulus to activate innate immune system.

(2) The adjuvant composition as defined in Paragraph (1) above, wherein the pH-sensitive carrier contains:
at least one species of pH-sensitive compound; and
at least one species of amphipathic substance, and
produces the membrane disruptive function promoting effect,
the pH-sensitive compound being selected from the group consisting of deoxycholic acid, cholic acid, ursodeoxycholic acid, chenodeoxycholic acid, hyodeoxycholic acid, 27C(higher) bile acid, glycodeoxycholic acid, glycyrrhizinic acid, and glycyrrhetinic acid, and salts thereof;
the amphipathic substance being selected from the group consisting of phosphatidylcholine having 10 to 12 carbon atoms, polyoxyethylene sorbitan monofatty acid ester having 12 to 18 carbon atoms, sorbitan fatty acid ester having 16 to 18 carbon atoms, glycerol monooleate, glycerol dilaurate, glycerol distearate, glycerol dioleate, polyoxyethylene castor oil, and α-tocopherol.

(3) The adjuvant composition as defined in Paragraph (1) or (2) above, wherein the substance with stimulus to activate innate immune system is monophosphoryl lipid A.

(4) The adjuvant composition as defined in Paragraph (2) or (3) above, wherein the substance with stimulus to activate innate immune system is contained in an amount of 0.0227 to 22.7 mol for 100 mol of the amphipatic substance.

(5) A vaccine composition including the adjuvant composition defined in any one of Paragraphs (1) to (4) above and an antigen.

(6) The vaccine composition as defined in Paragraph (5) above, wherein the antigen is a peptide or protein.

(7) The vaccine composition as defined in Paragraph (5) or (6) above, wherein the antigen is contained in an amount of 3.2 to 400 μg for 100 nmol of the amphipathic substance.

(8) A method for producing an adjuvant composition, including:
associating among
at least one species of pH-sensitive compound,
at least one species of amphipathic substance, and
a substance with stimulus to activate innate immune system;
the pH-sensitive compound being selected from the group consisting of deoxycholic acid, cholic acid, ursodeoxycholic acid, chenodeoxycholic acid, hyodeoxycholic acid, 27C (higher) bile acid, glycodeoxycholic acid, glycyrrhizinic acid, and glycyrrhetinic acid, and salts thereof;
the amphipathic substance being selected from the group consisting of phosphatidylcholine having 10 to 12 carbon atoms, polyoxyethylene sorbitan monofatty acid ester having 12 to 18 carbon atoms, sorbitan fatty acid ester having 16 to 18 carbon atoms, glycerol monooleate, glycerol dilaurate, glycerol distearate, glycerol dioleate, polyoxyethylene castor oil, and α-tocopherol.

(9) A method for producing a vaccine composition, including:
associating among at least one species of pH-sensitive compound, at least one species of amphipathic substance, and a substance with stimulus to activate innate immune system, the pH-sensitive compound being selected from the group consisting of deoxycholic acid, cholic acid, ursodeoxycholic acid, chenodeoxycholic acid, hyodeoxycholic acid, 27C(higher) bile acid, glycodeoxycholic acid, glycyrrhizinic acid, and glycyrrhetinic acid, and salts thereof, the amphipathic substance being selected from the group consisting of phosphatidylcholine having 10 to 12 carbon atoms, polyoxyethylene sorbitan monofatty acid ester having 12 to 18 carbon atoms, sorbitan fatty acid ester having 16 to 18 carbon atoms, glycerol monooleate, glycerol dilaurate, glycerol distearate, glycerol dioleate, polyoxyethylene castor oil, and α-tocopherol;
mixing the product of the association with an antigen to obtain a mixture;
freeze-thawing the mixture obtained by the mixing to obtain a melt; and
freeze-drying the melt obtained by the freeze-thawing.

BRIEF DESCRIPTION OF THE DRAWINGS

FIGS. 2(A)-2(C) depict the result of evaluation of CTL induction by ELIspot method. FIG. 2(A) is a graph depicting the number of IFNγ spots. FIG. 2(B) depicts spot formation in the case where peptide is used alone. FIG. 2(C) depicts spot formation in the case where peptide is used in combination with MPL-containing DLPC-deoxycholic acid complex (adjuvant composition). The condition of evaluation is $2\times10^6$ cells/well.

FIG. 3(A) depicts the result in the case where peptide is used alone. FIG. 3(B) depicts the result in the case where peptide and MPL-dispersion are used. FIG. 3(C) depicts the result in the case where peptide is used in combination with monophosphoryl lipid A (MPL)-containing DLPC-deoxycholic acid complex (adjuvant composition).

FIGS. 4(A)-4(C) depict the result obtained in the case where the CTL induction rate was evaluated by using any one of the vaccine compositions prepared by various preparation methods. FIG. 4(A) depicts the result in the case where MPL-containing DLPC-deoxycholic acid complex (prepared by the preparation method by dispersion) was used. FIG. 4(B) depicts the result in the case where MPL-containing DLPC-deoxycholic acid complex (prepared by the preparation method by mixing) was used. FIG. 4(C) depicts the result in the case where MPL-containing DLPC-deoxycholic acid complex (prepared by the preparation method by freeze-thawing and freeze-drying) was used.

FIG. 5(A) is a graph depicting absorbance determined by Lowry method before and after the peptide solution was filtered. FIG. 5(B) is a graph depicting absorbance determined by lipid test Wako before and after the adjuvant composition was filtered. FIG. 5(C) depicts the result of evaluation of the incorporation rate determined for various vaccine compositions.

FIGS. 6(A)-6(F) depict the result of test on the stimulus to activate innate immune system. This test is intended to verify the evaluation system. FIG. 6(A) depicts the result of evaluation of flow cytometry, with the cultured mice spleen cells not stained. FIG. 6(B) depicts the enhanced expression of CD80 in the case where PBS is added alone. FIG. 6(C) depicts the enhanced expression of CD80 in the case where LPS is added. FIG. 6(D) is a graph depicting the result of flow cytometry in the case where LPS is added in various concentrations. FIG. 6(E) depicts the enhanced expression of CD86 as other costimulatory molecules. FIG. 6(F) depicts the enhanced expression of CD40 as other costimulatory molecules.

FIG. 8(A) depicts the result of examination for the enhanced expression of CD80 in the case where MPL-free DLPC-deoxycholic acid complex is added in various amounts. FIG. 8(B) depicts the result of examination for the enhanced expression of CD80 in the case where the sample solutions in various kinds are added.

FIG. 11(A) depicts the result in the case where the amount is 10. FIG. 11(B) depicts the result in the case where the amount is 20. FIG. 11(C) depicts the result in the case where the amount is 640.

FIG. 13(A) depicts the result in the case where peptide is used. FIG. 13(B) depicts the result in the case where OVA is used.

FIGS. 15(A)-15(B) depict the result of examination for the influence of the complexing of the pH-sensitive compound on the strength of the adjuvant composition's and the vaccine composition's stimulus to activate innate immune system. FIG. 15(A) depicts the result in the case where the compositions are prepared by using deoxycholic acid varying in complex amount, with the MPL content fixed at 0.0227 mol. FIG. 15(B) depicts the result in the case where the compositions are prepared by using deoxycholic acid varying in complex amount, with the MPL content fixed at 22.7 mol.

FIG. 16(A) depicts the result in the case where the vaccine composition is prepared by using the pH-sensitive compound varying in kind, with the MPL content fixed at 0.0227 mol. FIG. 16(B) depicts the result in the case where the vaccine composition is prepared by using the pH-sensitive compound varying in kind, with the MPL content fixed at 22.7 mol.

FIG. 17(A) depicts spot formation in the case where the peptide and the MPL dispersion are used under the condition of high MPL level. FIG. 17(B) depicts spot formation in the case where the peptide and the adjuvant composition are used under the condition of high MPL level. The condition of evaluation is $1\times10^6$ cells/well.

FIGS. 18(A)-18(E) depict the result of evaluation by ELIspot method for the vaccine composition prepared with the pH-sensitive compound varying in kind. In this examination, the antigen is OVA, and the substance to stimulate innate immune system or the adjuvant composition is varied as follows. FIG. 18(A) depicts spot formation in the case where MPL dispersion is used. FIG. 18(B) depicts spot formation in the case where MPL-containing DLPC-deoxycholic acid is used. FIG. 18(C) depicts spot formation in the case where MPL-containing DLPC-cholic acid is used. FIG. 18(D) depicts spot formation in the case where MPL-containing DLPC-ursodeoxycholic acid is used. FIG. 18(E) depicts spot formation in the case where MPL-containing DLPC-hyodeoxycholic acid is used. The condition of evaluation is $2\times10^6$ cells/well.

FIG. 20(A) depicts the CTL induction rate in the case where the antigen is given restimulation. FIG. 20(B) depicts the CTL induction rate in the case where the antigen is not given restimulation.

FIGS. 21(A)-21(L) depict the result of evaluation by ELIspot method for the antigen specificity of CTL. FIGS. 21(A) to 21(F) depict spot formation in the case where there is restimulation. FIGS. 21(G)-21(L) depict spot formation in the case where there is no restimulation. FIGS. 21(A) and 21(G) depict the result in the case where OVA (80 μg) and MPL dispersion are used. FIGS. 21(B) and 21(H) depict the result in the case where OVA (80 μg) and the adjuvant composition which is prepared with deoxycholic acid (160 nmol) are used. FIGS. 21(C) and 21(I) depict the result in the case where OVA (80 μg) and the adjuvant composition which is prepared with deoxycholic acid (640 nmol) are used. FIGS. 21(D) and 21(J) depict the result in the case where peptide (80 μg) and MPL dispersion are used. FIGS. 21(E) and 21(K) depict the result in the case where peptide (80 μg) and the adjuvant composition which is prepared with deoxycholic acid (160 nmol) are used. FIGS. 21(F) and 21(L) depict the result in the case where peptide (80 μg) and the adjuvant composition which is prepared with deoxycholic acid (640 nmol) are used for administration to mice. The condition of evaluation is $2\times10^6$ cells/well.

FIGS. 23(A)-23(D) depict the result of evaluation by ELIspot method in the case where CpG-ODN is used. FIG. 23(A) depicts spot formation in the case OVA (80 μg) and CpG-ODN alone are administered to the mice. FIG. 23(B) depicts spot formation in the case where OVA (80 μg) and the adjuvant composition containing CpG-ODN are used. FIG. 23(C) depicts spot formation in the case where OVA (80 μg) and CpG-ODN alone are administered to the mice, with the antigen given no restimulation. FIG. 23(D) depicts spot formation in the case where OVA (80 μg) and the adjuvant composition containing CpG-ODN are used, with the antigen given no restimulation.

DETAILED DESCRIPTION

According to embodiments, there is provided an adjuvant composition containing a pH-sensitive carrier and a substance with stimulus to activate innate immune system. The foregoing adjuvant composition serves as a carrier for effective induction of CTL. The adjuvant composition is also a safe carrier.

<Adjuvant Composition>

The adjuvant composition contains a pH-sensitive carrier and a substance with stimulus to activate innate immune system. (The pH-sensitive carrier will be simply referred to as "carrier," "associated body," or "complex" in some instances hereinafter.)

The adjuvant composition may be characterized in that the pH-sensitive carrier therein may be composed of at least one species of pH-sensitive compound and at least one species of amphipathic substance, and the adjuvant composition produces the membrane disruptive function promoting effect. The pH-sensitive compound is selected from the group consisting of deoxycholic acid, cholic acid, ursodeoxycholic acid, chenodeoxycholic acid, hyodeoxycholic acid, 27C(higher) bile acid, glycodeoxycholic acid, glycyrrhizinic acid, and glycyrrhetinic acid, and salts thereof, and the amphipathic substance is selected from the group consisting of $C_{10-12}$ phosphatidylcholine, $C_{12-18}$ polyoxyethylene sorbitan monofatty acid ester, $C_{16-18}$ sorbitan fatty acid ester, glycerol monooleate, glycerol dilaurate, glycerol distearate, glycerol dioleate, polyoxyethylene castor oil, and α-tocopherol.

The embodiments will be described below in more detail with reference to the accompanying drawings. The following description is not intended to restrict or limit the technical scope of the present invention, which should be defined according to the claims appended hereto. The attached drawings may not be on the correct scale, and may be exaggerated for the sake of explanation.

Figure 1:
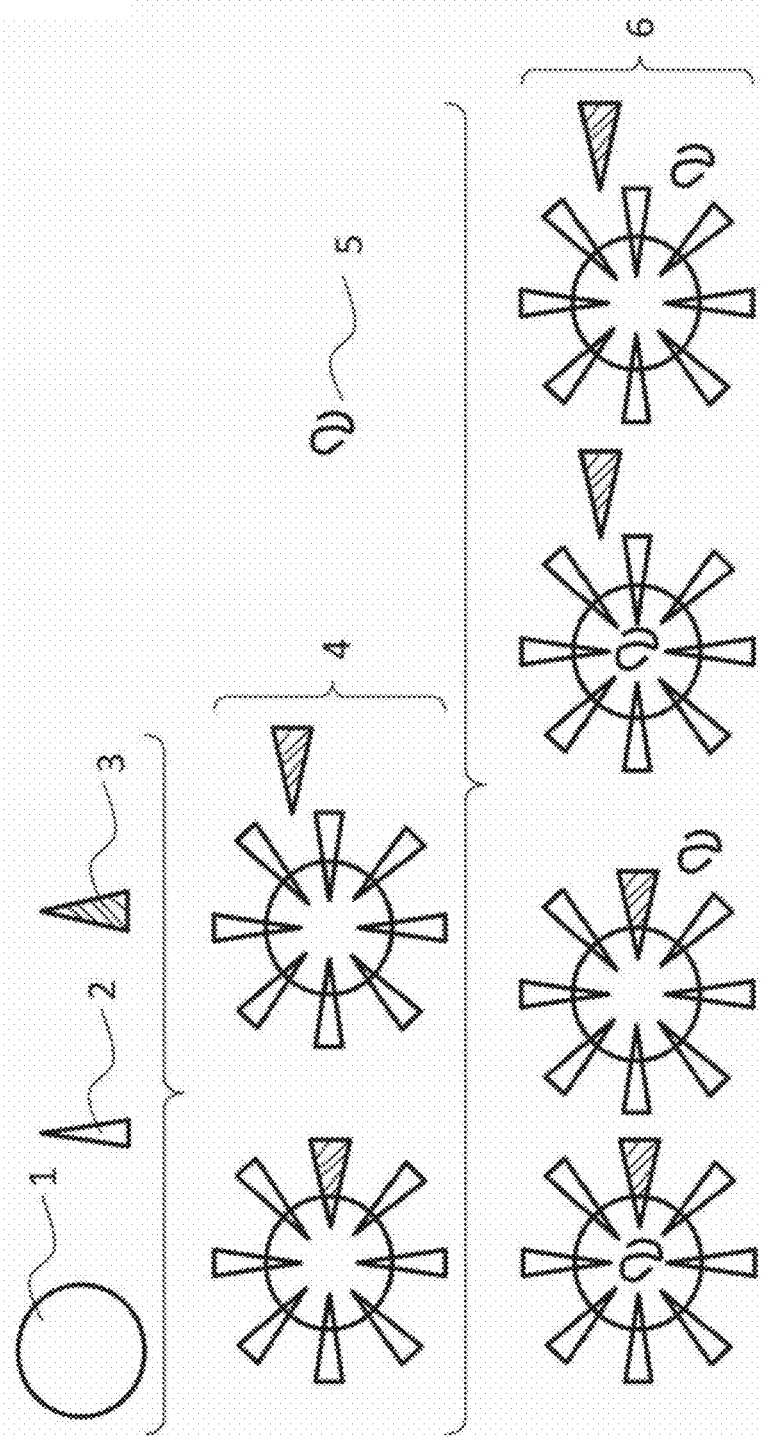
FIG. 1 is a schematic diagram depicting an adjuvant composition and a vaccine composition containing the same according to one embodiment of the present disclosure.

FIG. 1 is a schematic diagram depicting the adjuvant composition and the vaccine composition containing the same.

It is noted from FIG. 1 that an adjuvant composition 4 contains an amphipathic substance 1, a pH-sensitive compound 2, and a substance 3 with stimulus to activate innate immune system. It is also noted from FIG. 1 that both the substance 3 with stimulus to activate innate immune system and the pH-sensitive compound 2 associate with the hydrophobic moiety of the amphipathic substance 1. In this case, the adjuvant composition 4 may be regarded as an adjuvant complex. It is also noted that the substance 3 with stimulus to activate innate immune system exists independently of the pH-sensitive carrier containing the amphipathic substance 1 and the pH-sensitive compound 2.

Moreover, a vaccine composition 6 contains the adjuvant composition 4 and an antigen 5. As depicted in FIG. 1, the antigen 5 may exist either inside or outside the adjuvant composition 4. The vaccine composition 6 in which the adjuvant composition 4 contains the antigen 5 may be regarded as a vaccine complex.

The term "adjuvant composition" denotes a composition which contains the pH-sensitive carrier and the substance with stimulus to activate innate immune system. It may take on any form without specific restrictions or limitations. In other words, the "adjuvant composition" may be a mixture composed of the pH-sensitive carrier and the substance with stimulus to activate innate immune system. It may also be one (adjuvant complex) in which the pH-sensitive carrier supports thereon or contains therein the substance with stimulus to activate innate immune system. Both may be collectively referred to as "adjuvant composition" in this specification.

The term "vaccine composition" denotes any composition which contains the adjuvant composition and the antigen. It may take on any form without specific restrictions or limitations. In other words, the "vaccine composition" may be a mixture composed of two or more components selected from the group consisting of the constituents of the adjuvant composition and the antigen, or one (vaccine complex) in which the adjuvant complex supports thereon or contains therein the antigen. In this specification, both may be collectively referred to as "vaccine composition."

[pH-Sensitive Carrier]

The pH-sensitive carrier may be sensitive to pH, so that it transports the antigen in cells to the cytosol when its surrounding decreases in pH.

The pH-sensitive carrier may not be specifically restricted or limited. However, it should preferably be one which may be composed of at least one species of pH-sensitive compound and at least one species of amphipathic substance, and may be capable of producing the membrane disruptive function promoting effect. The pH-sensitive compound may be selected from the group consisting of deoxycholic acid, cholic acid, ursodeoxycholic acid, chenodeoxycholic acid, hyodeoxycholic acid, 27C(higher) bile acid, glycodeoxycholic acid, glycyrrhizinic acid, and glycyrrhetinic acid, and salts thereof. The amphipathic substance may be selected from the group consisting of $C_{10-12}$ phosphatidylcholine, $C_{12-18}$ polyoxyethylene sorbitan monofatty acid ester, $C_{16-18}$ sorbitan fatty acid ester, glycerol monooleate, glycerol dilaurate, glycerol distearate, glycerol dioleate, polyoxyethylene castor oil, and α-tocopherol. The "carbon number" for the amphipathic substance denotes the number of carbon atoms in the fatty acid (acyl group) constituting the hydrophobic moiety of the amphipathic substance.

The following is a detailed description of the pH-sensitive carrier which may be composed of the pH-sensitive compound and the amphipathic substance, and produces the membrane disruptive function promoting effect.

(Structure of pH-Sensitive Carrier)

It is considered that the pH-sensitive carrier may be formed by association between the pH-sensitive compound and the amphipathic substance at a physiological pH or higher. To be more specific, it is considered that the pH-sensitive carrier is formed when the pH-sensitive compound associates with the hydrophobic moiety of the amphipathic substance. The form of association of the pH-sensitive carrier is hypothetical, and pH-sensitive carrier is not restricted or limited by the form of association.

(Membrane Disruptive Function Promoting Effect)

The term "Membrane disruptive function" denotes the function to bring about release in the release test. The release test described in this specification is a test comprising or consisting of adding liposomes (dispersion) encapsulating an aqueous solution containing a quenching substance and a fluorescent substance and a dispersion of a sample for evaluation to a properly pH-adjusted aqueous solution, incubating the resulting aqueous solution at 37° C. for 90 minutes or 30 minutes, and measuring the fluorescence intensity of the incubated aqueous solution. This method permits the measurement of the amount of the fluorescent substance which has been released from the liposomes. In this way it is possible to verify that the pH-sensitive carrier functions to disrupt the membrane of the liposomes. The release test will be described in more detail in the Examples.

The term "to produce the membrane disruptive function promoting effect" means that the following two conditions are satisfied simultaneously.

(1) The release test indicates that the leakage is higher at a prescribed pH (lower than the physiological pH) than that at the physiological pH, and the amount of increase is larger than that observed in the experiment which is carried out with the pH-sensitive compound alone.

(2) The release test at a prescribed pH lower than the physiological pH indicates that the leakage in the case where the pH-sensitive compound and the amphipathic substance form a complex (or the pH-sensitive carrier) is larger than the sum of the leakage due to the pH-sensitive compound used alone and the leakage due to the amphipathic substance used alone.

More specifically, the term "to produce the membrane disruptive function promoting effect" means the following. The release test at pH 7.4 and pH 5.0 or pH 4.5 indicates that the relation among La, Lb, and Lc exists as indicated by the following two equations, where La represents the leakage for the pH-sensitive compound existing alone, Lb represents the leakage for the amphipathic substance existing alone, and Lc represents the leakage for the pH-sensitive carrier (which is a complex of the pH-sensitive compound and the amphipathic substance). In other words, what is mentioned in (1) and (2) above is expressed respectively in terms of the equations (1) and (2) below. In the following equations, $La_{7.4}$, $Lb_{7.4}$, and $Lc_{7.4}$ denote the leakage at pH 7.4, and $La_x$, $Lb_x$, and $Lc_x$ denote the leakage at pH 5.0 or pH 4.5.

[Math 1]

$$\Delta = (Lc_x - Lc_{7.4}) - (La_x - La_{7.4}) > 0 \quad \text{Equation (1)}$$

$$\Delta' = Lc_x - (La_x + Lb_x) > 0 \quad \text{Equation (2)}$$

In the equation (1) above, $\Delta$ should be larger than 0, preferably 5 or larger, more preferably 10 or larger, and most preferably be 30 or larger. Also, in the equation (2) above, $\Delta'$ should be larger than 0, preferably 5 or larger, more preferably 10 or larger than, and most preferably 15 or larger.

According to embodiments, it is desirable that the values of both $\Delta$ and $\Delta'$ in the equations (1) and (2) above should be 5 or larger, and that the pH-sensitive carrier should be one which contains bile acid and lipid. According to embodiments, it is desirable that the values of both $\Delta$ and $\Delta'$ in the equations (1) and (2) above should be 5 or larger and that the pH-sensitive carrier should be one which contains glycyrrhizinic acid or both glycyrrhetinic acid and lipid.

The term "physiological pH" means a pH value in normal tissue or normal body fluid. The physiological pH is usually 7.4, but it may slightly vary (±0.1) from one normal tissue or one normal body fluid to another. The term "prescribed pH lower than the physiological pH" means a pH lower than 7.4, preferably a pH 3.0 or more but less than 7.4, more preferably a pH 4.0 or more but less than 7.3, and most preferably a pH 4.5 or more but less than 7.0.

Without wishing to be bound by any particular theory, it is believed that the mechanism by which the pH-sensitive carrier produces the membrane disruptive function promoting effect. However, the following discussion is not intended to restrict or limit the scope of the present invention and disclosure.

It is assumed that the pH-sensitive carrier changes the mode of association between the pH-sensitive compound and the amphipathic substance when the environment decreases in pH lower than the physiological pH, and this leads to the membrane disruptive function promoting effect. For example, if a system containing a pH-sensitive carrier and a biomembrane (such as cell membrane and vesicle membrane) changes such that its pH decreases below the physiological pH, the pH-sensitive carrier would change in the mode of association after contact with the biomembrane, thereby undergoing change in the structure of the biomembrane. In other words, the pH-sensitive carrier would bring about change in the structure of the biomembrane. Without wishing to be bound by any particular theory, a probable reason for this may be that the environment of weakly acidic pH makes unstable the pH-sensitive compound in the pH-sensitive carrier in the structure of the carrier, with the result that the pH-sensitive carrier undergoes rearrangement with the biomembrane existing in the system, thereby producing the membrane disruptive function promoting effect. The foregoing may be put in another way as follows. The pH-sensitive compound comprises or consists of molecules which, when it becomes weakly acidic pH, undergo protonation and change in solubility for hydrophobic association. In other words, the hydrophobic association involving the pH-sensitive compound responds to the weak acid environment, thereby producing its function. The term "membrane disruption" means the change in membrane structure as mentioned above. It does not necessarily mean that the membrane-constituting components are entirely separated or decomposed. As the result of such "membrane disruption," any component that may be contained inside the biomembrane (such as endosome) is released to the outside (e.g., cytosol) of the biomembrane.

The pH-sensitive carrier may preferably be one which has a leakage lower than 20% at pH 7.4 and higher than 20% at pH 4.0 in the release test. The leakage in the release test may preferably be lower than 20% at pH 6.5 and higher than 20% at pH 4.0. The leakage at pH 7.4 or pH 6.5 may preferably be 15% or lower, more preferably 10% or lower. The leakage at pH 4.0 may preferably be 40% or higher, more preferably 50% or higher. With the leakage as defined above, the pH-sensitive carrier easily produces the effect of promoting the membrane-disruption effect at a slightly low pH.

In addition, the pH-sensitive carrier produces not only the membrane disruptive function promoting effect but also the membrane fusion function promoting effect.

The term "membrane-fusion function" means the function that brings about membrane-fusion in the membrane-fusion test. The membrane-fusion test denotes a test which comprises or consists of adding liposomes (dispersion) having two kinds of fluorescent substances built into the liposomal-menbrane and a dispersion of sample for evaluation into an aqueous solution adjusted to a prescribed pH, incubating the resulting aqueous solution at 37° C. for 60 minutes, and measuring the fluorescence intensity of the incubated aqueous solution. This test permits the measurement of change in energy resonance transfer for the two kinds of fluorescent substances incorporated into the liposomes, thereby verifying the membrane-fusion function of the pH-sensitive carrier. The membrane-fusion test will be described in more detail in the Examples.

The term "to produce the membrane fusion function promoting effect" means a situation in which the membrane-fusion test indicates that the fusion rate at a prescribed pH lower than the physiological pH is higher than the fusion rate at the physiological pH and the amount of increase is larger than that observed when the pH-sensitive compound is tested alone. More specifically, the term "to produce the membrane fusion function promoting effect" means that the membrane-fusion tests at pH 7.4 and pH 5.0 indicate that there exists the relation represented by the following equation (3) between the fusion rate Rc (%) of the pH-sensitive carrier (which is a complex of a pH-sensitive compound and an amphipathic substance) and the fusion rate Ra (%) of the pH-sensitive compound used alone. In the equation below, $Rc_{7.4}$ and $Ra_{7.4}$ represent the fusion rate at pH 7.4, and $Rc_x$ and $Ra_x$ represent the fusion rate at pH 5.0.

[Math 2]

$$\Delta R = (Rc_x - Rc_{7.4}) - (Ra_x - Ra_{7.4}) > 0 \quad \text{Equation (3)}$$

The value of $\Delta R$ in equation (3) above should be larger than 0, preferably 2 or larger, more preferably 5 or larger, and most desirably 10 or larger.

The pH-sensitive carrier should preferably be one which has $\Delta R$ equal to or larger than 2 in equation (3) and contains bile acid and lipid.

The pH-sensitive carrier produces the membrane fusion function promoting effect at a slightly low pH (or a prescribed pH lower than the physiological pH). Without wishing to be bound by any particular theory, it is believed that the mechanism may be similar to that in the membrane disruptive function promoting effect. This discussion is not intended to restrict or limit the scope of the present invention and disclosure.

It is assumed that the pH-sensitive carrier contributes to membrane-fusion as the result of rearrangement of biomembranes existing in the system when the environment decreases in pH lower than the physiological pH so as to change the mode of association between the pH-sensitive compound and the amphipathic substance. The membrane-fusion takes place as the result of rearrangement among components having affinity with each other, and hence those components (such as antigen) which have no or little affinity with biomembrane are excluded and released from the membrane which undergoes rearrangement.

As mentioned above, the antigen may be surrounded by endosome, which is one kind of biomembrane, so that it is taken into cells (such as antigen presenting cells). After that, the endosome decreases in pH due to proton pumping action. The endosome further fuses with lysosome containing hydrolases. In this way, the antigen is degraded. Subsequently, the degraded antigen forms a complex with MHC Class II molecules, thereby presenting the antigen to CD4 positive T cells. Therefore, most of the antigen is not delivered into the cytosol.

By contrast, the pH-sensitive carrier permits the antigen (such as exogenous antigen) to be delivered to the cytosol. More specifically, an environment with a decreased pH similarly occurs when the antigen together with the pH-sensitive carrier is surrounded by endosomes and taken into cells. As the result of pH decrease (or acidification), the pH-sensitive compound makes unstable the pH-sensitive carrier, so that the rearrangement of membrane takes place between the endosome and the pH-sensitive carrier. This causes the pH-sensitive carrier to produce the membrane-disruption function (which produces itself together with the membrane-fusion function in some cases). This membrane-disruption function (or both the membrane-fusion function and the membrane-disruption function) causes the antigen to be delivered into the cytosol from the endosome. The foregoing mechanism suggests that, in principle, the antigen can be transported to the cytosol once it has been taken into the endosome together with the pH-sensitive carrier. This indicates the possibility of using the antigen and the pH-sensitive carrier in the form of their mixed composition or using the antigen in such a form that it is supported on or contained in the pH-sensitive carrier.

(pH-Sensitive Compound)

As mentioned above, the pH-sensitive compound may be at least one species selected from the group consisting of deoxycholic acid, cholic acid, ursodeoxycholic acid, chenodeoxycholic acid, hyodeoxycholic acid, 27C(higher) bile acid, glycodeoxycholic acid, glycyrrhizinic acid, and glycyrrhetinic acid, and salts thereof. The pH-sensitive compounds in salt form include, without limitation, alkali metal salts (such as lithium salt, sodium salt, and potassium salt), alkaline earth metal salts (such as magnesium salt, calcium salt, and barium salt), and ammonium salt. These pH-sensitive compounds may be used alone or in combination with one another.

According to embodiments, the pH-sensitive compound may preferably be at least one species selected from the group consisting of deoxycholic acid, cholic acid, ursodeoxycholic acid, chenodeoxycholic acid, hyodeoxycholic acid, glycodeoxycholic acid, and glycyrrhizinic acid, and salts thereof.

According to embodiments, the pH-sensitive compound may preferably be at least one species selected from the group consisting of deoxycholic acid, ursodeoxycholic acid, chenodeoxycholic acid, hyodeoxycholic acid, glycodeoxycholic acid, glycyrrhizinic acid, and salts thereof. More preferably, it may be at least one species selected from the group consisting of deoxycholic acid, ursodeoxycholic acid, and glycyrrhizinic acid, and salts thereof.

The pH-sensitive compounds, such as deoxycholic acid, cholic acid, ursodeoxycholic acid, chenodeoxycholic acid, hyodeoxycholic acid, 27C(higher) bile acid, and glycodeoxycholic acid, are generally called bile acid. Bile acid has been known as a steroid derivative since before the 1920s, and has been used in the field of bacteriology. The bile acid in the living human body forms a complex with cholesterol, lipid, and fat-soluble vitamin, thereby assisting their absorption. Moreover, bile acid forms a complex with lipid, protein, or hydrophobic material owing to its physicochemical properties, and hence it has long been used for protein separation and purification and also as a solubilizer or emulsifier. Recently, it has attracted attention in the field of vaccine production and drug absorption promoter, which is enabled bile acid transporter. Examples of bile acid for such purposes are sodium deoxycholate (also known as sodium desoxycholate) and ursodeoxycholic acid (also known as ursodesoxycholic acid); they have found use as pharmaceutical additives suitable for injection into human bodies owing to their safety. For this reason, the pH-sensitive compound may preferably be selected from deoxycholic acid, and ursodeoxycholic acid, and salts thereof (such as sodium salt).

The amount of the pH-sensitive compound for 100 mol of the amphipathic substance may be 10 mol or more, preferably 10 to 640 mol, more preferably 20 to 320 mol, and most preferably 20 to 160 mol. The term "amount of the complex of the pH-sensitive compound" may be used to denote the content of the pH-sensitive compound for 100 mol of the amphipathic substance.

(Amphipathic Substance)

As mentioned above, the amphipathic substance may be at least one species selected from the group consisting of $C_{10-12}$ phosphatidylcholine, $C_{12-18}$ polyoxyethylene sorbitan monofatty acid ester, $C_{16-18}$ sorbitan fatty acid ester, glycerol monooleate, glycerol dilaurate, glycerol distearate, glycerol dioleate, polyoxyethylene castor oil, and α-tocopherol. These amphipathic substances may be used alone or in combination with one another.

The term "carbon number" of the amphipathic substance denotes the number of carbon atoms in the fatty acid (acyl group) constituting the hydrophobic moiety of the amphipathic substance.

The $C_{10-12}$ phosphatidylcholine may preferably be diacylphosphatidylcholine having saturated acyl groups. Non-limiting examples of this compound include didecanoylphosphatidylcholine (DDPC; 1,2-didecanoyl-sn-glycero-3-phosphatidylcholine) and dilauroylphosphatidylcholine (DLPC; 1,2-dilauroyl-sn-glycero-3-phosphatidylcholine). The phosphatidylcholine may be natural, synthetic prepared by any known method, or commercial.

The $C_{12-18}$ polyoxyethylene sorbitan monofatty acid ester includes, for example, polyoxyethylene sorbitan monolauric acid ester (polyoxyethylene sorbitan monolaurate), polyoxyethylene sorbitan myristic acid ester (polyoxyethylene sorbitan monomyristate), polyoxyethylene sorbitan monopalmitic acid ester (polyoxyethylene sorbitan palmitate), polyoxyethylene sorbitan monostearic acid ester (polyoxyethylene sorbitan monostearate), and polyoxyethylene sorbitan monooleic acid ester (polyoxyethylene sorbitan monooleate). Although the polyoxyethylene is not specifically restricted or limited in the degree of polymerization, the polyoxyethylene chains (combined together) are preferably added to sorbitan have the degree of polymerization of 10 to 200, preferably 15 to 100, and more preferably 20 to 50. The polyoxyethylene sorbitan monofatty acid ester may be synthetic or commercial. The polyoxyethylene sorbitan monofatty acid ester may be commercially available under the trade name of Tween 20 (polyoxyethylene sorbitan monolaurate ester), Tween 40 (polyoxyethylene sorbitan monopalmitate ester), Tween 60 (polyoxyethylene sorbitan monostearate ester), and Tween 80 (polyoxyethylene sorbitan monooleate ester). Preferable among these products are $C_{16-18}$ polyoxyethylene sorbitan monofatty acid ester (Tween 20, Tween 40, Tween 60, and Tween 80).

The $C_{16-18}$ sorbitan fatty acid ester includes sorbitan monofatty acid ester, such as sorbitan monopalmitic acid ester (sorbitan monopalmitate), sorbitan monostearic acid ester (sorbitan monostearate), and sorbitan monooleic acid ester (sorbitan monooleate). It also includes sorbitan trifatty acid ester, such as ester of sorbitan tripalmitic acid (sorbitan tripalmitate), ester of sorbitan tristearic acid (sorbitan tristearate), and ester of sorbitan trioleic acid (sorbitan trioleate). The sorbitan fatty acid ester may be synthetic or commercial. The sorbitan fatty acid ester may be commercially available under the trade name of SPAN 40 (sorbitan palmitic acid ester), SPAN 60 (sorbitan stearic acid ester), SPAN 80 (sorbitan oleic acid ester), SPAN 65 (sorbitan tristearic acid ester), and SPAN 85 (sorbitan trioleic acid ester). Preferable among them are SPAN 80, SPAN 65, and SPAN 85.

The glycerol monooleate (glyceryl monooleate), glycerol dilaurate (glyceryl dilaurate), glycerol distearate (glyceryl distearate), and glycerol dioleate (glyceryl dioleate) are acyl glycerol formed by ester linkage from glycerin and one or two molecules of fatty acid. The site of linkage for the fatty acid is not specifically restricted or limited. In the case of glycerol monooleate which is monoacyl glycerol, for example, the ester linkage of the fatty acid may exist at the C1 or C2 position of glycerin. Also, in the case of glycerol dilaurate, glycerol distearate, or glycerol dioleate which is diacyl glycerol, the ester linkage of the fatty acid may exist at the C1 and C2 positions of glycerin or at the C1 and C3 positions of glycerin. A preferable example of glycerol dilaurate is α,α'-dilaurin, in which substitution occurs at the C1 and C3 positions. Preferable examples of the glycerol distearate and glycerol dioleate include diacyl glycerol in which substitution occurs at the C1 and C2 positions. These glycerol derivatives may be synthetic or commercial.

The polyoxyethylene castor oil may be formed by addition of polyoxyethylene to castor oil. The polyoxyethylene may have a degree of polymerization (which is not specifically restricted or limited) in the range of 3 to 200, preferably 5 to 100, more preferably 10 to 50. The polyoxyethylene castor oil may be synthetic or commercial.

The α-tocopherol may be natural, synthetic prepared by any known method, or commercial.

Preferable among the above-mentioned amphipathic substances are those selected from the group consisting of $C_{10-12}$ phosphatidylcholine, polyoxyethylene sorbitan monolaurate, polyoxyethylene sorbitan monooleate, sorbitan monooleate, polyoxyethylene castor oil, and α-tocopherol. More preferable examples are those selected from the group consisting of dilauroyl phosphatidylcholine, didecanoyl phosphatidylcholine, polyoxyethylene sorbitan monolaurate, polyoxyethylene sorbitan monooleate, sorbitan monooleate, polyoxyethylene castor oil, and α-tocopherol.

(Combination of pH-Sensitive Compound and Amphipathic Substance)

The pH-sensitive carrier produces the membrane disruptive function promoting effect at a desired pH because it may be composed of the pH-sensitive compound and the amphipathic substance which are combined together. The combination of the pH-sensitive compound and the amphipathic substance affects the pH at which the pH-sensitive carrier starts to produce the membrane disruptive function promoting effect. Without wishing to be bound by any particular theory, it is believed that a probable reason for this is that the pH-sensitive compound varies in pKa and the mode of association with the amphipathic substance also varies depending on the combination of the pH-sensitive compound and the amphipathic substance. This implies that an adequate combination of the pH-sensitive compound and the amphipathic substance makes it possible to select any pH suitable for the desired effect and to meticulously set up the mode of delivery.

The following are non-limiting preferable examples of the combination of the pH-sensitive compound and the amphipathic substance in the pH-sensitive carrier.

Cholic acid and DLPC; deoxycholic acid and DDPC; deoxycholic acid and DLPC; deoxycholic acid and Tween 20; deoxycholic acid and Tween 40; deoxycholic acid and Tween 60; deoxycholic acid and Tween 80; deoxycholic acid and SPAN 40; deoxycholic acid and SPAN 60; deoxycholic acid and SPAN 80; deoxycholic acid and SPAN 65; deoxycholic acid and SPAN 85; deoxycholic acid and α-tocopherol; deoxycholic acid and glycerol monooleate; deoxycholic acid and glycerol distearate; deoxycholic acid and glycerol dioleate; deoxycholic acid and glycerol dilaurate (α,α'-dilaurin); deoxycholic acid and polyoxyethylene castor oil; chenodeoxycholic acid and DLPC; hyodeoxycholic acid and DLPC; glycodeoxycholic acid and DLPC; ursodeoxycholic acid and DDPC; ursodeoxycholic acid and DLPC; ursodeoxycholic acid and Tween 20; ursodeoxycholic acid and Tween 40; ursodeoxycholic acid and Tween 60; ursodeoxycholic acid and Tween 80; ursodeoxycholic acid and SPAN 40; ursodeoxycholic acid and SPAN 60; ursodeoxycholic acid and SPAN 80; ursodeoxycholic acid and SPAN 65; ursodeoxycholic acid and SPAN 85; ursodeoxycholic acid and α-tocopherol; ursodeoxycholic acid and glycerol monooleate; ursodeoxycholic acid and glycerol distearate; ursodeoxycholic acid and glycerol dioleate; ursodeoxycholic acid and glycerol dilaurate (α,α'-dilaurin); ursodeoxycholic acid and polyoxyethylene castor oil; glycyrrhizinic acid and DDPC; glycyrrhizinic acid and DLPC; glycyrrhizinic acid and Tween 20; glycyrrhizinic acid and Tween 40; glycyrrhizinic acid and Tween 60; glycyrrhizinic acid and Tween 80; glycyrrhizinic acid and SPAN 40; glycyrrhizinic acid and SPAN 60; glycyrrhizinic acid and SPAN 80; glycyrrhizinic acid and SPAN 65; glycyrrhizinic acid and SPAN 85; glycyrrhizinic acid and α-tocopherol; glycyrrhizinic acid and glycerol monooleate; glycyrrhizinic acid and glycerol distearate; glycyrrhizinic acid and glycerol dioleate; glycyrrhizinic acid and glycerol dilaurate (α,α'-dilaurin); and glycyrrhizinic acid and polyoxyethylene castor oil.

More non-limiting preferable examples are listed below.

Cholic acid and DLPC; deoxycholic acid and DDPC; deoxycholic acid and DLPC; deoxycholic acid and Tween 20; deoxycholic acid and Tween 40; deoxycholic acid and Tween 60; deoxycholic acid and Tween 80; deoxycholic acid and SPAN 40; deoxycholic acid and SPAN 65; deoxycholic acid and SPAN 80; deoxycholic acid and SPAN 85; deoxycholic acid and α-tocopherol; deoxycholic acid and glycerol monooleate; deoxycholic acid and polyoxyethylene castor oil; chenodeoxycholic acid and DLPC; hyodeoxycholic acid and DLPC; glycodeoxycholic acid and DLPC; ursodeoxycholic acid and DDPC; ursodeoxycholic acid and DLPC; ursodeoxycholic acid and Tween 40; ursodeoxycholic acid and Tween 60; ursodeoxycholic acid and Tween 80; ursodeoxycholic acid and SPAN 40; ursodeoxycholic acid and SPAN 65; ursodeoxycholic acid and SPAN 85; ursodeoxycholic acid and α-tocopherol; ursodeoxycholic acid and monooleate; ursodeoxycholic acid and polyoxyethylene castor oil; glycyrrhizinic acid and DDPC; glycyrrhizinic acid and DLPC; glycyrrhizinic acid and Tween 40; glycyrrhizinic acid and Tween 60; glycyrrhizinic acid and Tween 80; glycyrrhizinic acid and SPAN 40; glycyrrhizinic acid and SPAN 65; glycyrrhizinic acid and SPAN 85; glycyrrhizinic acid and α-tocopherol; glycyrrhizinic acid and glycerol monooleate; and glycyrrhizinic acid and polyoxyethylene castor oil.

[Substance with Stimulus to Activate Innate Immune System]

The substance with stimulus to activate innate immune system may be defined as a substance which is recognized by the receptor for structural pattern recognition and activates immunocompetent cells.

The substance with stimulus to activate innate immune system is not specifically restricted or limited; however, it may preferably be an agonist for Toll-like receptors.

The substance with stimulus to activate innate immune system includes the following non-limiting examples.

Mineral salts such as alum; gel-type adjuvants such as aluminum hydroxide, aluminum phosphate, and calcium phosphate; immunoregulatory DNA sequences including CpG motif; immunostimulatory RNA molecules; endotoxins (lipopolysaccharide (LPS: endotoxin)); monophosphoryl lipid A (MPL: registered trademark), exotoxins such as cholera toxin, E. coli, thermolabile toxin, and pertussis toxin; microbial adjuvants such as muramyl dipeptide and flagellin; oil adjuvants such as incomplete Freund's adjuvant (IFA); oil adjuvants such as liquid paraffin and lanolin; biodegradable microspheres; saponins (QS-21, Quil-A, etc.); nonionic block copolymers; muramyl peptide analogs; polyphosphazenes; synthetic polynucleotides such as non-CpG synthetic polynucleotide; synthetic adjuvants such as imidazoquinoline; cationic lipids such as DOTAP, DC-Chol, and DDA; single-stranded RNA; and double-stranded RNA.

Preferable non-limiting examples of the substance with stimulus to activate innate immune system among the foregoing are listed below. Mineral salts such as alum; gel-type adjuvants such as aluminum hydroxide, aluminum phosphate, and calcium phosphate; immunoregulatory DNA sequences including CpG motif; immunostimulatory RNA molecules; monophosphoryl lipid A (MPL: registered trademark), exotoxins such as cholera toxin, E. coli, thermolabile toxin, and pertussis toxin; microbial adjuvants such as flagellin; saponins (QS-21, Quil-A, etc.); synthetic polynucleotides such as non-CpG synthetic polynucleotide; synthetic adjuvants such as imidazoquinoline; single-stranded RNA; and double-stranded RNA. Most preferable are monophosphoryl lipid A and immunoregulatory DNA sequences including CpG motif.

The substance with stimulus to activate innate immune system may be used alone or in combination with one another.

The substance with stimulus to activate innate immune system may vary in content depending on the kind of the substance with stimulus to activate innate immune system used. An adequate content for 100 mol of the amphipathic substance may be 0.0227 to 22.7 mol, preferably 0.227 to 2.27 mol. A content of the substance with stimulus to activate innate immune system, which content may be equal to or more than 0.0227 mol, is desirable because it is high enough to adequately induce the immune response. Also, a content of the substance with stimulus to activate innate immune system, which content may be equal to or lower than 22.7 mol, is desirable for cost reduction.

[Aqueous Solvent]

The adjuvant composition may contain an aqueous solvent.

In the case where the adjuvant composition contains an aqueous solvent, the pH-sensitive carrier and the substance with stimulus to activate innate immune system may form a dispersion in the aqueous solvent.

In this situation, the pH-sensitive carrier may preferably form in the aqueous medium a complex containing the pH-sensitive compound and the amphipathic substance. This complex may take on any form without specific restrictions or limitations. That is, the pH-sensitive compound and the amphipathic substance may form a membrane. Alternatively, the amphipathic substance may form a structure in which the pH-sensitive compound is partly or entirely embedded by association. It is desirable that the pH-sensitive compound and the amphipathic substance form micelle particles together. (Micelle particles result from hydrophobic interaction between the pH-sensitive compound and the amphipathic substance. They are typically particles of monomolecular film structure.) The micelle particles may have a diameter of 10 to 200 nm, preferably 10 to 100 nm, because they actively perform phagocytosis and endocytosis only when they have a particle diameter equal to or larger than a certain level. The above-mentioned micelle particles do not include those which form lipid bimolecular membrane structure (such as liposome). The particle diameter of the pH-sensitive carrier may be measured by the dynamic light scattering method (with NanoZS90 made by MALVERN Instruments Co., Ltd.).

The adjuvant composition may preferably be one which forms in an aqueous medium a complex (adjuvant complex) which may be composed of the pH-sensitive carrier in the form of complex and the substance with stimulus to activate innate immune system. Although the complex is not specifically restricted or limited in its form, it may preferably take on the form of micelle particles composed of the pH-sensitive compound and the amphipathic substance composing the pH-sensitive carrier and the substance with stimulus to activate innate immune system. The micelle particles may have a particle diameter of 10 to 200 nm, preferably 10 to 100 nm.

The aqueous solution containing the adjuvant composition, at least one of the pH-sensitive compound, the amphipathic substance, and the substance to activate innate immune system remains free without undergoing association.

The medium for the aqueous solution containing the pH-sensitive carrier may preferably be an aqueous solution containing a buffering agent, NaCl, sugar (such as glucose and sucrose), etc.

The buffering agent is not specifically restricted or limited; any known one may be used so long as it may keep the pH of the adjuvant composition equal to or higher than the physiological pH. Non-limiting examples of the buffering agent are listed below.

Phosphate buffers; citrate buffers; citrate-phosphate buffers; tris(hydroxymethyl)aminomethane-HCl buffers (trishydrochloric acid buffer); MES buffers (2-morpholinoethane sulfonate buffer); TES buffers (N-tris(hydroxymethyl)

methyl-2-aminoethane sulfonate buffer); acetate buffers; MOPS buffers (3-morpholinopropane sulfonate buffer); MOPS-NaOH buffers; HEPES buffers (4-(2-hydroxyethyl)-1-piperazine ethanesulfonate buffer); HEPES-NaOH buffers and other GOOD buffers; amino acid buffers such as glycine-hydrochloric acid buffer, glycine-NaOH buffer, glycylglycine-NaOH buffer, and glycylglycine-KOH buffer; boric acid-based buffers such as Tris-borate buffer, borate-NaOH buffer, and borate buffer; and imidazole buffers. Preferable among these buffers are phosphate buffers; citrate buffers; citrate-phosphate buffers; Tris-hydrochloric acid buffers; MES buffers; acetate buffers; and HEPES-NaOH buffers. These buffers may be used in any concentration without specific restrictions or limitations. An adequate concentration is 0.1 to 200 mM, preferably 1 to 100 mM. The term "concentration of buffer" denotes the concentration (mM) of the buffer contained in the aqueous solution.

The concentration of NaCl and sugar (such as glucose and sucrose) are not specifically restricted or limited; and may preferably be 0.1 to 200 mM, more preferably 1 to 150 mM.

The concentration of the pH-sensitive carrier in the aqueous solution is not specifically restricted or limited; and may be such that the total molar concentration of the pH-sensitive compound and the amphipathic substance is 0.73 µmol/L to 7.4 mmol/L, preferably 7.3 µmol/L to 6.5 mmol/L, and more preferably 8.0 µmol/L to 4.2 mmol/L.

Moreover, the aqueous solution may contain the substance with stimulus to activate innate immune system in any molar concentration without specific restrictions or limitations. An adequate concentration may be 0.14 nmol/L to 0.227 mmol/L, preferably 1.4 nmol/L to 0.19 mmol/L, and more preferably 1.6 nmol/L to 0.12 mmol/L.

[Additional Components]

The adjuvant composition may further contain additional components without specific restrictions or limitations such as a stabilizer.

The stabilizer is not specifically restricted or limited and any known one may be used so long as it does not adversely affect the pH-sensitive carrier and the substance with stimulus to activate innate immune system. Non-limiting examples of the stabilizer are listed below.

Saturated or unsaturated $C_{4-20}$ alcohols, such as 1-octanol, 1-dodecanol, 1-hexadodecanol, and 1-eicosanol; saturated or unsaturated $C_{12-18}$ fatty acids such as lauric acid, myristic acid, palmitic acid, stearic acid, and oleic acid; $C_{1-3}$ alkyl esters of saturated or unsaturated $C_{8-18}$ fatty acids such as methyl caprylate (methyl octanoate), ethyl caprylate (ethyl octanoate), methyl laurate, ethyl laurate, ethyl myristate, ethyl palmitate, ethyl stearate, methyl oleate, and ethyl oleate; D(L)-amino acids such as D(L)-alanine, arginine, asparagine, aspartic acid, cysteine, glutamine, glycine, histidine, leucine, isoleucine, lysine, methionine, proline, serine, threonine, tryptophan, tyrosine, valine, and phenylalanine; amino acid triglycerides such as tricaproin and tricaprylin; $C_{12-18}$ polyoxyethylene sorbitan trifatty acid esters such as polyoxyethylene sorbitan tripalmitic acid ester and polyoxyethylene sorbitan trioleic acid ester (known, for example, as Tween 65 and Tween 85); $C_{12-18}$ polyoxyethylene alkyl esters such as polyoxyethylene lauric acid ester, polyoxyethylene myristic acid ester, polyoxyethylene palmitic acid ester, and polyoxyethylene stearic acid ester (known, for example, as PEG20 stearyl ether and PEG23 lauryl ether); polyoxyalkylene hardened castor oil (known, for example, as PEG10 hardened castor oil, PEG40 hardened castor oil, and PEG60 hardened castor oil); saturated or unsaturated $C_{8-18}$ monofatty acid glycerol esters such as caprylin (glycerol octanoate), glycerol monocaprylate, glycerol monolaurate, glycerol monomyristate, glycerol monopalmitate, glycerol monostearate, and glycerol monooleate; glycerols of $C_{8-16}$ difatty acids such as glycerol dioctanoate, glycerol dicaprylate, glycerol dilaurate, glycerol dimyristate ester, and glycerol dipalmitate; α-tocopherol acetate ester; castor oil; soybean oil; cholesterol; squalene; squalane; lactose; ascorbyl palmitate; benzyl benzoate; methyl paraoxybenzoate; ethyl paraoxybenzoate; propyl paraoxybenzoate; and butyl paraoxybenzoate. The "carbon number" for the stabilizer denotes the number of carbon atoms in the fatty acid component (acyl group) constituting the hydrophobic moiety.

The content of the additional components is not specifically restricted or limited so long as it does not adversely affect the pH-sensitive carrier and the substance with stimulus to activate innate immune system. An adequate content for 100 mol of the amphipathic substance may be 150 mol or lower, preferably more than 0 mol and 66.4 mol or lower.

The adjuvant composition effectively induces CTL when administered together with an antigen.

In other words, the adjuvant composition permits the pH-sensitive carrier used in combination with the substance with stimulus to activate innate immune system to appropriately exhibit its function e.g., its membrane disruptive function promoting effect and its membrane fusion function promoting effect. Moreover, the pH-sensitive carrier used in combination with the substance with stimulus to activate innate immune system allows the substance with stimulus to activate innate immune system to appropriately exhibit its function. Without wishing to be bound by any particular theory, this may be reasoned as follows.

The pH-sensitive carrier in its desirable form contains the pH-sensitive compound and the amphipathic substance and also has the membrane disruptive function promoting effect (and the membrane disruptive function promoting effect as well as the membrane fusion function promoting effect in some cases). The membrane disruptive function promoting effect (and the membrane fusion function promoting effect) may be attributable to the fact that the pH-sensitive carrier changes in the state of association owing to the pH-sensitive compound in an acidic environment and the rearrangement with the cell membrane (such as endosome) may be brought about by the amphipathic substance in such a situation. The pH-sensitive compound changes the state of association of the pH-sensitive carrier because it does not change in pH sensitivity even though the pH-sensitive carrier is combined with the substance with stimulus to activate innate immune system. Moreover, the amphipathic substance does not affect the rearrangement with cell membranes even though the substance with stimulus to activate innate immune system is incorporated into the amphipathic substance or exists independently of the pH-sensitive carrier. Thus, the substance with stimulus to activate innate immune system does not impair the function of the pH-sensitive carrier even though it is used in combination with the pH-sensitive carrier. Further, the substance with stimulus to activate innate immune system keeps its function unimpaired because it may be merely incorporated into the amphipathic substance of the pH-sensitive carrier by the hydrophobic mutual action and it also merely exists independently of the pH-sensitive carrier. Consequently, the adjuvant composition causes the antigen to be introduced into a cytosol by the function of the pH-sensitive carrier and, at the same time, the substance with stimulus to activate innate immune system acts when it is administered together with the antigen. As a result, the adjuvant composition effectively induces cross-presentation due to the antigen introduced into the cytosol and hence effectively induces CTL.

According to embodiments, the adjuvant composition also effectively induces humoral immunity.

As mentioned above, any exogenous antigen may be degraded into peptide fragments by the endosome in the antigen presenting cells and forms a complex with MHC class II molecules to be presented to the CD4 positive T cells.

The adjuvant composition leads the antigen administered together with it to cross-presentation, thereby inducing CTL. Thus, when the pH-sensitive carrier brings about rearrangement of the cell membrane of endosome, the antigen and the substance with stimulus to activate innate immune system are introduced into the cytosol. However, there may exist an instance in which the antigen and the substance with stimulus to activate innate immune system remain partly or entirely in the endosome even though the rearrangement is brought about. Also, there may also exist an instance in which only the antigen is taken up in part of endosome if the antigen and the adjuvant composition exist mutually independently. Thus, the antigen may be degraded into peptide fragments by endosome and such peptide fragments form a complex with MHC class II molecules, thereby presenting antigen to the CD4 positive T cells and inducing humoral immunity. The induction of humoral immunity appropriately occurs because the dendritic cells which effectively induce cross-presentation are in the immunologically activated state. Alternatively, the dendritic cells which effectively induce cross-presentation actively generates cytokine (e.g., IFNγ), which activates immunity, thereby leading the surrounding environment to the environment suitable for immune induction.

Therefore, the adjuvant composition may induce the cross-presentation or the humoral immunity in place of the cross-presentation.

<Vaccine Composition>

The vaccine composition may contain an adjuvant composition and an antigen.

[Adjuvant Composition]

The adjuvant composition may be the same or similar to those previously described and hence, its description is omitted here.

[Antigen]

The antigen may not be specifically restricted or limited so long as it produces immune response; and may preferably be a peptide or protein.

Non-limiting examples of the peptide and protein include viral antigens; bacterial antigens; mycotic antigens; protozoan antigens or verminous antigens; cancer antigens; allergy-related antigens; disease-related antigens; and graft rejection-related antigens.

Non-limiting examples of the foregoing viral antigen include the following without specific restrictions or limitations.

Human immunodeficiency virus (HIV) antigens such as gene product of gag, pol, and env genes, Nef protein, reverse transcriptase, and other HIV components; hepatitis virus antigens such as S, M, and L protein of hepatitis B virus, pre-S antigen of hepatitis B virus, hepatitis C virus RNA, and virus components of hepatitis A, B, and C; influenza virus antigens such as hemagglutinin, neuraminidase, and other influenza virus components; measles virus antigens; rubella virus antigens; rotavirus antigens; cytomegalovirus antigens; respiratory syncytial virus antigens; herpes simplex virus antigens; varicella zoster virus antigens; Japanese encephalitis virus antigens; and rabies virus antigens. Additional non-limiting examples include peptides derived from adenoviruses; retroviruses; picornaviruses; herpesviruses; rotaviruses; hantaviruses; coronaviruses; togaviruses; flaviviruses; rhabdoviruses; paramyxoviruses; orthomyxoviruses; bunyaviruses; arenaviruses; reoviruses; papillomaviruses; parvoviruses; poxviruses; hepadnaviruses; and spongy viruses;

Non-limiting examples of the foregoing bacterial antigens include the following without specific restrictions or limitations. Bacterial antigens such as pertussis toxin, filamentous hemagglutinin, pertactin, FIM2, FIM3, cyclase adenylate, and other pertussis bacterial antigen components; diphteria bacterial antigens such as diphteria toxin or toxoid, and other diphteria bacterial antigen components; bacterial antigens of tetanus *bacillus* and *streptococcus*, such as tetanus toxin or toxoid, and other tetanus bacterial antigen components; Gram-negative bacillary bacterial antigens such as lipopolysaccharide, and other Gram-negative bacterial antigen components; tubercle *bacillus* bacterial antigens such as mycolic acid, heat-shock protein 65 (HSP 65), 30 kDa major secretory protein, antigen 85A, and other mycobacteria antigen components; *helicobacter* and *pylori* bacterial antigen components; pneumococcus bacterial antigen; influenza *bacillus* bacterial antigen; anthrax *bacillus* bacterial antigen; and rikettsia bacterial antigen.

Non-limiting examples of the foregoing mycotic antigen include the following without specific restrictions or limitations. *Candida* mycotic antigen components; *histoplasma* mycotic antigens; *cryptococcus* mycotic antigens; *coccidioides* mycotic antigens; and ringworm mycotic antigens.

Non-limiting examples of the foregoing protozoan antigen or verminous antigen include the following without specific restrictions or limitations. *Plasmodium falciparum* antigens; *toxoplasma* antigens; *schistosoma* antigens; *Leishmania* antigens; and trypanosome *cruzi* antigens.

Non-limiting examples of the foregoing cancer antigen unrestrictedly include those cancer antigens derived from the cell surface of cells of tumor tissue, protoplasm, nuclei, and cell organelles. Non-limiting examples of the cancer include the following. Leukemia; lymphoma; nervous tumor; melanoma; breast cancer; lung cancer; head and neck cancer; stomach cancer; colon cancer; liver cancer; pancreatic cancer; cancer of the uterine cervix; uterine cancer; ovarian cancer; vaginal cancer; testis cancer; prostatic cancer; penile cancer; bone tumors; hemangioma; lip cancer; cancer of epipharynx; pharyngeal cancer; carcinoma of the esophagus; rectal cancer; carcinoma of the gallbladder; cancer of the bile duct; laryngeal cancer; lung cancer; bladder carcinoma; kidney cancer; brain tumor; thyroid carcinoma; Hodgkin's disease; and non-Hodgkin lymphoma. Non-limiting examples of the cancer antigen are listed below. HER2/neu (Human EGFR related 2); CEA (Carcinogenic Embryonic Antigen); MAGE (Melanoma-associated Antigen); XAGE (X antigen family member); NY-ESO-1; gp100; Melan/mart-1; Tyrosinase; PSA (Prostate Sepecific Antigen); PAP (Prostate Acid Phosphatase); p53; K-ras; N-ras; Bcr-Abl; MUC-1 (Mucin-1); PSMA (Prostate Specific Membrane Antigen); survivin; WT-1 (Wilms tumor suppressor gene 1); AFP (Alpha Fetoprotein); GPC (Glypican); and EGFR (Epidermal Growth Factor Receptor).

Non-limiting examples of the foregoing allergy-related antigens include the following without specific restrictions or limitations. Pollen antigens such as cedar pollen antigen, ragweed pollen antigen, and ryegrass pollen antigen; animal-derived antigens such as rat mite antigen and cat antigen; histocompatible antigens; and therapeutic drugs such as penicillin.

The foregoing disease-related antigen (autoimmune disease and allergy) results from the diseases whose examples are listed below without specific restrictions or limitations. Diabetes; articular rheumatism; myasthenia gravis; systemic lupus erythematosus; atopic dermatitis; psoriasis; Sjögren's syndrome; alopecia areata; Crohn's disease; ulcerative colitis; conjunctivitis; keratoconjunctivitis; asthma; allergic asthma; proctitis; drug eruption; allergic encephalomyelitis; acute necrotizing hemorrhagic encephalopathy; hypoplastic anemia; erythroblast anemia; idiopathic thrombocytsopenia; Wegener granulomatosis; Stevens-Johnson syndrome; and interstitial pulmonary fibrosis. Specific non-limiting examples of the antigens involved in autoimmune disease include, for example, glutamic acid decarboxylase 65 (GAD 65); natural DNAs; myelin basic proteins; myelin proteolipid proteins; acetylcholine receptor components; thyroglobulins; and thyroid stimulating hormone (TSH) receptors.

Non-limiting examples of the foregoing graft rejection-related antigens unrestrictedly includes the antigenic components of the graft to be transferred to the graft recipient, the graft including heart; lung; liver; pancreas; kidney; and nerve.

The above-mentioned antigens may be used alone or in combination with one another.

The antigen may be contained in an amount of 3.2 to 400 µg, preferably 16 µg to 80 µg, for 100 nmol of the amphipathic substance as a constituent of the pH-sensitive carrier.

Although the antigen may exist independently of the adjuvant composition, the ratio of the antigen to be incorporated into the adjuvant composition may be equal to or higher than 3%, preferably 5 to 80%, more preferably 10 to 60%. The ratio equal to or higher than 3% is desirable because, when the vaccine composition is incorporated into cells by endocytosis, the antigen may be readily introduced into the same endosome as that into which the adjuvant composition may be introduced. This leads to desirable effects The "incorporation rate of the antigen" denotes the ratio of the antigen to the adjuvant composition which contains or supports the antigen. The value of the ratio may be obtained by methods described in the Examples.

[Additives]

The vaccine composition may additionally contain pharmaceutical additives.

The suitable additives vary depending on the dosage form of the vaccine composition. The vaccine composition may be solid preparations, such as tablets; powders; and capsules or liquid preparations such as parenteral solution; with the latter being preferable. The liquid preparations may be supplied in a dried form which may be restored with water or any other adequate diluent at the time of use.

The vaccine composition in the form of tablets or capsules may preferably be provided with enteric coatings. The enteric coating may be one which is ordinarily used in the field concerned. The vaccine composition may also contain any one of capsules, powders, and liquids.

The vaccine composition in the form of solid preparations may contain a diluent such as sugar (e.g., lactose and sucrose); starch (e.g., corn starch); cellulose (e.g., crystalline cellulose); acacia; magnesium metasilicate aluminate; and calcium phosphate; a lubricant such as magnesium stearate, talc, and polyethylene glycol); a binder such as sugar (e.g., mannitol and sucrose, crystalline cellulose, polyvinylpyrrolidone, and hydroxypropylmethyl cellulose); a disintegrator such as starch (e.g., potato starch, cellulose e.g., carboxymethyl cellulose, and crosslinked polyvinylpyrrolidone); a coloring agent, and a corrigent.

On the other hand, the vaccine composition in the form of liquid preparations may contain a solvent such as physiological saline, sterilized water, and buffer solution; a membrane stabilizer such as cholesterol; a tonicity adjusting agent such as sodium chloride, glucose, and glycerin; an antioxidant such as tocopherol, ascorbic acid, and glutathione; and anticeptics such as chlorobutanol and paraben. The solvent may be the same one as used for preparation of the vaccine composition.

The vaccine composition may induce cell-mediated immunity through effective cross-presentation of the antigen. This permits the induction of CTL. The term "induce cell-mediated immunity" means that the CTL induction rate is higher than that in control which is not treated with the vaccine composition. Additionally, the term "CTL induction rate" means the ratio of IFNγ-secreting cells that accounts for in all the CD8 positive cells.

The adjuvant composition produces the effect of enhancing cell-mediated immunity in view of the fact that it gives a higher CTL induction rate than in control treated with the substance to activate innate immune system even though the same antigen may be administered. The term "produce the effect of enhancing CTL induction" means that a higher CTL induction rate is obtained than in the case where the substance to stimulate innate immune system is used alone. Thus, the effect of enhancing CTL induction may be accompanied by the induction of cell-mediated immunity.

The vaccine composition may be able to induce immune response for humoral immunity. Thus, it may be able to produce an antibody such as IgG. Here, the term "induce humoral immunity" means that the IgG antibody titer is higher than in that of control which is not treated with the vaccine composition.

The vaccine composition involves the effect of enhancing humoral immunity in view of the fact that it gives a higher IgG antibody titer than in control treated with the substance to activate innate immune system.

[Applications]

The vaccine composition produces the membrane disruptive function promoting effect or the membrane disruptive function promoting effect and the membrane fusion function promoting effect, thereby allowing the antigen to efficiently release to the cytosol, when it is administered to a subject and the external environment of the vaccine composition decreases in pH below the physiological pH (e.g., pH 6.5). Thus, it appropriately induces cell-mediated immune to develop immunity.

Thus, the vaccine composition provides a method for therapy or prevention of diseases by including administration of the vaccine composition in an effective amount to a subject who needs therapy or prevention of diseases.

The method for administration of the vaccine composition is not specifically restricted or limited and may include oral administration and parenteral administration such as intravenous injection; arterial injection; subcutaneous injection; endodermic injection; intramuscular injection; intrathecal injection; dermal administration; and percutaneous absorption. The vaccine composition that contains peptide or protein as the antigen may suitable for parenteral administration, particularly subcutaneous injection; endodermic injection; intramuscular injection; and intravenous injection. Note that the vaccine composition in which the antigen is simply mixed with the adjuvant composition without being supported on or contained in it may be suitable for local administration, specifically subcutaneous injection, endodermic injection, and intramuscular injection.

The above-mentioned subject may preferably be a mammal, especially human.

The above-mentioned diseases include, for example, virus infectious diseases such as human immunodeficiency syndrome (HIV), hepatitis, and influenza; bacterial infections such as pertussis, diphtheria, tetanus, tuberculosis, *Helicobacter pylori*, and microbism caused by pneumococcus; mycosis such as *candida*; protozoiassis or vermiculous infections such as malaria; cancers such as leukemia, lymphoma, nervous tumor, melanoma, breast cancer, lung cancer, head and neck cancer, stomach cancer, colon cancer, liver cancer, pancreatic cancer, cancer of the uterine cervix, uterine cancer, ovarian cancer, vaginal cancer, testis cancer, prostatic cancer, penile cancer, osteoncus, hemangioma, lip cancer, cancer of epipharynx, pharyngeal cancer, carcinoma of the esophagus, rectal cancer, carcinoma of the gallbladder, cancer of the bile duct, laryngeal cancer, lung cancer, bladder carcinoma, kidney cancer, brain tumor, thyroid carcinoma, Hodgkin's disease, and non-Hodgkin lymphoma; allergy caused by cedar pollen; autoimmune diseases such as diabetes, articular rheumatism, myasthenia gravis, and systemic lupus erythematosus; and graft rejections such as graft-versus-host disease (GVHD).

In embodiments there is provided a method for therapy or prevention of diseases. Such a method may be found in the common technical knowledge.

According to embodiments, the vaccine composition permits the antigen to be transported to cells by culture. In other words, the vaccine composition provides a method for culture to transport the antigen to cells.

The above-mentioned method for culture includes cultivating cells by using a culture medium containing the vaccine composition.

The culture medium is not specifically restricted or limited; any known ones can be used. Non-limiting examples include MEM, DMEM, and RPMI.

No specific restrictions or limitations are imposed on the amount of the vaccine composition to be added to the culture medium. An adequate amount is such that the molar concentration of the amphipathic substance may be 0.66 µmol/L to 1.0 mmol/L, preferably 6.6 µmol/L to 0.88 mmol/L, and more preferably 7.2 µmol/L to 0.56 mmol/L.

The above-mentioned culture medium may have a pH value equal to or higher than 7.0, preferably 7.2 to 7.8. Any culture medium with a pH value equal to or higher than 7.0 is desirable because it keeps stable the pH-sensitive compound constituting the pH-sensitive carrier in the culture medium.

The above-mentioned cells include, without specific restrictions, those cells collected from the subject and established cultured cells.

Non-limiting examples of the cells collected from the subject or the cells collected from established cultured cells include dendritic cells, NK (Natural Killer) cells; T lymphocytes; B lymphocytes; and lymphoblasts.

Preferable among the cells mentioned above are cells collected from the subject, more preferably dendritic cells; NK cells; T lymphocytes; and lymphoblasts collected from the subject; and most desirably dendritic cells.

Collection of cells from the subject may be accomplished by blood collection or biopsy. The method of culture includes collecting cells from the subject.

The cultured cells may be administered to the subject for therapy or prevention of the subject's disease.

The method for treating and preventing disease, includes collecting cells from the subject, cultivating the collected cells by using a culture medium containing the vaccine composition, and administrating the cultured cells to the subject.

Thus, the foregoing method may be used to treat and prevent diseases, whose examples were mentioned above.

<Method for Producing the Adjuvant Composition>

The adjuvant composition may be produced by various methods without specific restrictions.

The adjuvant composition in which the pH-sensitive carrier and the substance with stimulus to activate innate immune system exist independently may be produced by mixing together the pH-sensitive carrier and the substance with stimulus to activate innate immune system. In addition, the adjuvant composition in which the substance with stimulus to activate innate immune system is supported on or contained in the pH-sensitive carrier may be produced by associating the pH-sensitive carrier with the substance with stimulus to activate innate immune system.

The following is a description of a preferred embodiment of the method for producing the adjuvant composition in which the pH-sensitive carrier may be composed of a prescribed pH-sensitive compound and a prescribed amphipathic substance, the pH-sensitive carrier possessing the membrane disruptive function promoting effect.

The method for producing the adjuvant composition involves associating with one other at least one species of pH-sensitive compound, at least one species of amphipathic substance, and a substance with stimulus to activate innate immune system. The pH-sensitive compound may be selected from the group consisting of deoxycholic acid; cholic acid; ursodeoxycholic acid; chenodeoxycholic acid; hyodeoxycholic acid; 27C(higher) bile acid; glycodeoxycholic acid; glycyrrhizinic acid; and glycyrrhetinic acid; and salts thereof. The amphipathic substance may be selected from the group consisting of $C_{10-12}$ phosphatidylcholines; $C_{12-18}$ polyoxyethylene sorbitan monofatty acid esters; $C_{16-18}$ sorbitan fatty acid esters; glycerol monooleates; glycerol dilaurates; glycerol distearates; glycerol dioleates; polyoxyethylene castor oils; and α-tocopherols.

Associating with one other the pH-sensitive compound, the amphipathic substance, and the substance with stimulus to activate innate immune system may be accomplished in such a way that they come into contact with one another in an aqueous solution. Therefore, the adjuvant composition may be produced by causing the pH-sensitive compound, the amphipathic substance, and the substance with stimulus to activate innate immune system to come into contact with one another in an aqueous solution. The associating described above (e.g., associating of the at least one species of pH-sensitive compound, the at least one species of amphipathic substance, and a substance with stimulus to activate innate immune system) refers to, for example, the state of assembling by hydrophobic interaction. etc.

There are no specific restrictions or limitations as to the method for bringing the pH-sensitive compound, the amphipathic substance, and the substance with stimulus to activate innate immune system into contact with one another in an aqueous solution. Any method is acceptable so long as it forms an associated body. Thus the adjuvant composition may be produced by either of the following methods.

(1) The first method comprises or consists of preparing separately an aqueous solution containing a pH-sensitive compound, an aqueous solution containing an amphipathic substance, and an aqueous solution containing a substance with stimulus to activate innate immune system, mixing these aqueous solutions, and vigorously stirring the mixed solution by means of an emulsifier, vortex mixer, ultrasonic wave, or the like to achieve their dispersion.

(2) The second method may be known as Bangham method for producing liposome. The Bangham method comprises or consists of the following. First, the constituents of the adjuvant composition may be dissolved in an organic solvent (e.g., methanol and chloroform) in a glass container. The resulting solution may be freed of the organic solvent by means of a rotary evaporator or the like, so that a thin film may be formed on the wall of the glass container. Then, the glass container, in which a thin film has been formed, is given an aqueous solution, so that the thin film is moistened at 5 to 35° C. The glass container may be vigorously shaken at 5 to 35° C. by means of an emulsifier, vortex mixer, ultrasonic wave, or the like, so that the thin film is thoroughly dispersed into the aqueous solution. The details of Bangham method may be found in the literature on the method for producing liposome, such as "Liposome" (compiled by Shoshichi Nojima, Junzo Sunamoto, and Keizo Inoue, published by Nankoudo), and "Liposome in Life Science" (compiled by Hiroshi Terada and Tetsuro Yoshimura, published by Springer-Verlag, Tokyo).

The first method (1) mentioned above may be modified such that the aqueous solution containing the amphipathic substance may be mixed with the pH-sensitive compound and the substance with stimulus to activate innate immune system. The solvent for the aqueous solution may be the same one as mentioned above. In the first method (1) mentioned above, no specific restrictions or limitations are imposed on the temperature at which the aqueous solutions are prepared and stirred. An adequate temperature may be 5 to 35° C., preferably 15 to 25° C. at normal temperature.

The adjuvant composition containing an aqueous solvent as a component thereof may be incorporated with additional components such as stabilizer in any way without specific restrictions or limitations. For example, it may be incorporated with an aqueous solution containing a pH-sensitive compound, an aqueous solution containing an amphipathic substance, and/or an aqueous solution containing a substance with stimulus to activate innate immune system. It may also be possible to prepare an aqueous solution containing the adjuvant composition from the thin film prepared by Bangham method in which they are dissolved together with the constituents of the adjuvant composition.

<Method for Producing Vaccine Composition>

The vaccine composition may be produced in various ways without specific restrictions or limitations. The method for producing the vaccine composition may includedispersion, mixing, and freeze-thawing and freeze-drying.

(Preparation Method by Dispersion)

The preparation method by dispersion may include mixing together the pH-sensitive compound, the amphipathic substance, the substance with stimulus to activate innate immune system, and the antigen. That is, the constituents of the adjuvant composition may be allowed to form a thin film on the wall of a glass container. Then, the glass container, in which a thin film has been formed, may be given a solution containing the antigen, so that the thin film may be moistened at 5 to 35° C. The glass container may be vigorously shaken for dispersion by means of an emulsifier, vortex mixer, ultrasonic wave, or the like. In this way, the vaccine composition may be prepared. Alternatively, a thin film containing the pH-sensitive compound and the amphipathic substance may be formed on the wall of a glass container. Then, the glass container, in which a thin film has been formed, may be given a solution containing the antigen and the substance with stimulus to activate innate immune system, so that the thin film may be moistened at 5 to 35° C. The glass container may be vigorously shaken by means of an emulsifier, vortex mixer, ultrasonic wave, or the like. In this way, the vaccine composition may be prepared.

The foregoing solution containing the antigen and the foregoing solution containing the antigen and the substance with stimulus to activate innate immune system may be the same ones or the referenced ones as prepared by mixing.

(Preparation Method by Mixing)

The preparation method by mixing may include mixing solutions each containing the pH-sensitive compound, the amphipathic substance, the substance with stimulus to activate innate immune system, and the antigen. In other words, the preparation method by mixing may include preparing the adjuvant composition by the above-mentioned methods (1) and (2). In the case where the adjuvant composition may be prepared by the method (2), the vaccine composition may be obtained by mixing together a dispersion of the adjuvant composition and the antigen or a solution containing the antigen. Alternatively, in the case where the adjuvant composition is obtained by the method (1), it may be desirable to prepare the following solutions.

Solution Containing pH-Sensitive Compound

The above-mentioned solution containing the pH-sensitive may include one of the pH-sensitive compound and the solvent. It may also contain optional additives.

The above-mentioned pH-sensitive compound may be the same one as mentioned above. Therefore its description is not repeated here.

The above-mentioned solvent may be an aqueous solution containing buffer, NaCl, or sugar (such as glucose and sucrose), or sterilized water. It may be desirable to use physiological saline, sterilized water, or buffer solution from the standpoint of administrating the vaccine composition into a living body.

The concentration of the pH-sensitive carrier in the solution containing the pH-sensitive compound may be one which is attained when the molar concentration of the pH-sensitive compound may be 0.066 µmol/L to 6.4 mmol/L, preferably 0.66 µmol/L to 5.6 mmol/L, and more preferably 0.72 µmol to 3.6 mmol/L.

Solution Containing Amphipathic Substance

The solution containing the amphipathic substance mentioned above may be composed of an amphipathic substance and a solvent. It may also contain optional additives.

The above-mentioned amphipathic substance and the above-mentioned solvent may be the same as mentioned earlier. Therefore their descriptions are not repeated here.

The concentration of the amphipathic substance in the solution containing the amphipathic substance may be such that the molar concentration of the amphipathic substance may be 0.66 µmol/L to 1.0 mmol/L, preferably 6.6 µmol/L to 0.88 mmol/L, and more preferably 7.2 µmol to 0.56 mmol/L.

Solution Containing Substance with Stimulus to Activate Innate Immune System

The above-mentioned solution containing the substance with stimulus to activate innate immune system includes the substance with stimulus to activate innate immune system and a solvent. It may also contain optional additives.

The substance with stimulus to activate innate immune system and the solvent may be the same as mentioned earlier. Therefore their descriptions are not repeated here.

The concentration of the substance with stimulus to activate innate immune system in the solution containing the substance with stimulus to activate innate immune system may be attained when the molar concentration of the substance with stimulus to activate innate immune system is 0.14 nmol/L to 0.227 mmol/L, preferably 1.4 nmol/L to 0.19 mmol, and more preferably 1.6 nmol/L to 0.12 mmol/L.

Solution Containing Antigen

The solution containing the antigen may include the antigen and a solvent.

The antigen and the solvent may be the same as mentioned earlier. Therefore their descriptions are not repeated here.

Mixing

No specific restrictions or limitations are imposed on the method of mixing together the solution containing the pH-sensitive compound, the solution containing the amphipathic substance, the solution containing the substance with stimulus to activate innate immune system, and the antigen.

The resulting mixed solution may preferably undergo dispersion. This dispersion may be accomplished with the help of emulsifier, vortex mixer, ultrasonic wave, or the like.

In embodiments, it may not be necessary prepare separately the solution containing the pH-sensitive compound, the solution containing the amphipathic substance, the solution containing the substance with stimulus to activate innate immune system, and the solution containing the antigen. Instead, it may be possible to use equal to or not less than two solutions in the form of mixture. For example, a first solution may be prepared which contains the pH-sensitive compound and the substance with stimulus to activate innate immune system, and a second solution is prepared which contains the amphipathic substance and the antigen. Then the two solutions are mixed together.

(Preparation Method by Freeze-Thawing and Freeze-Drying)

The preparation method by freeze-thawing and freeze-drying may include freeze-thawing a solution obtained by dispersion or mixing, thereby giving a molten solution, and freeze-drying the molten solution.

Preparing Molten Solution

The molten solution may be obtained by freeze-thawing the solution obtained by the preparation method by dispersion or mixing.

The term "freeze-thawing" means freeze-drying a solution and melting the resulting dried product.

The method for freeze-drying is not specifically restricted or limited and may be be achieved preferably by sublimation water with the help of liquefied nitrogen or cooled methanol.

The dried product may be molten in any way without specific restrictions or limitations. It may be desirable to heat the dried product resulting from cooling, or it may be desirable to add a solvent to the dried product.

Freeze-Drying

Freeze-drying is intended to freeze-dry the molten solution obtained as mentioned above.

The method for freeze-drying is not specifically restricted or limited as in the above-mentioned case, and it may be desirable to sublime water by means of liquefied nitrogen or cooled methanol.

Preferable among the above-mentioned methods for production of the vaccine composition may be the preparation method by freeze-thawing and freeze-drying of the antigen. The preparation method by freeze-thawing and freeze-drying permits the antigen to be easily supported on or contained in the adjuvant composition. This leads to a high incorporation rate of the antigen. More specifically, the preparation method by freeze-thawing and freeze-drying proceeds in such a way that thawing takes a certain period of time when the dried product obtained by freeze-drying may be molten in the stage of freeze-thawing. The result may be that the antigen and the adjuvant composition approach each other in the early stage of thawing. Once the antigen and the adjuvant composition approach each other, this state remains steady, and hence the antigen and the adjuvant composition stay close to each other in the solution which has undergone thawing. Freeze-drying in this state permits the antigen to be easily supported on or contained in the adjuvant composition, this leads to a high incorporation rate with the antigen.

The pH-sensitive carrier may contain a prescribed pH-sensitive compound and a prescribed amphipathic substance. Therefore, the method for producing the vaccine composition may include associating with one another at least one species of pH-sensitive compound, which may be selected from the group consisting of deoxycholic acid; cholic acid; ursodeoxycholic acid; chenodeoxycholic acid; hyodeoxycholic acid; 27C(higher) bile acid glycodeoxycholic acid; glycyrrhizinic acid; and glycyrrhetinic acid; and salts thereof, at least one species of amphipathic substance may be selected from the group consisting of $C_{10-12}$ phosphatidylcholine; $C_{12-18}$ polyoxyethylene sorbitan monofatty acid ester; $C_{16-18}$ sorbitan fatty acid ester; glycerol monooleate; glycerol dilaurate; glycerol distearate; glycerol dioleate; polyoxyethylene castor oil; and α-tocopherol; and a substance with stimulus to activate innate immune system; mixing the product obtained by the association with an antigen; freeze-thawing the thus obtained mixture; and freeze-drying the molten product obtained in freeze-thawing mentioned above.

EXAMPLES

The adjuvant composition, vaccine composition and method for producing both will be described below in more detail with reference to non-limiting Examples to be given later.

<Raw Materials>

The non-limiting examples were carried out with the following compounds. In case where the reagent name is identical with the product name, the product name is omitted.

(1) pH-Sensitive Compound

Sodium deoxycholate (from Nacalai Tesque Inc.)

Sodium cholate (from Nacalai Tesque Inc.)

Sodium ursodeoxycholate (from Tokyo Chemical Industry Co., Ltd.)

Chenodeoxycholic acid (from Tokyo Chemical Industry Co., Ltd.)

Hyodeoxycholic acid (from Tokyo Chemical Industry Co., Ltd.)

Sodium glycodeoxycholate (from Nacalai Tesque Inc.)

Monoammonium glycyrrhizinate (from Tokyo Chemical Industry Co., Ltd.)

(2) Amphipathic Substance

DDPC (1,2-didecanoyl-sn-glycero-3-phosphatidylcholine: from NOF Corporation, COATSOME MC-1010)

DLPC (1,2-dilauroyl-sn-glycero-3-phosphatidylcholine: from NOF Corporation, COATSOME MC-1212)

Polyoxyethylene sorbitan monofatty acid ester (Tween 20, 80: from Tokyo Chemical Industry Co., Ltd.)

Sorbitan fatty acid ester (SPAN 80: from Nacalai Tesque Inc.—sorbitan nomooleate)

Polyoxyethylene castor oil (from Wako Pure Chemical Industries, Ltd. Polyoxyethylene 10 castor oil)

α-tocopherol (from Nacalai Tesque Inc., DL-α-tocopherol)

(3) Substance with Stimulus to Activate Innate Immune System

MPL (Monophosphoryl lipid A) (from Sigma Corporation, Lipid A, Monophosphory *salmonella* serotype/from InvivoGen, Monophosphoryl Lipid A (synthetic)

WA (Freund's Incomplete Adjuvant) (from Santa Cruz Biotechnology, Inc.)

CpG-DNA (CpG-ODN: from InvivoGen, ODN-2395)

LPS (endotoxin) (from Wako Pure Chemical Industries, Ltd., derived from *Escherichia coli* 0111, extracted by phenol)

(4) Solvent, etc.

Water for injection (from Otsuka Pharmaceutical Co., Ltd.)

MES-Na (from Merck Ltd.)

Sodium chloride (from Kanto Chemical Co., Inc.)

PBS Tablets (Phosphate buffered saline: from Takara Bio Inc.)

Methanol (from Nacalai Tesque Inc.)

Chloroform (from Wako Pure Chemical Industries, Ltd.)

Sodium hydroxide aqueous solution (0.1 mol/L: from Nacalai Tesque Inc.)

Hydrochloric acid (0.1 mol/L, 1 mol/L: from Nacalai Tesque Inc.)

OVA peptide: SIINFEKL, (outsourced for synthesis by PH Japan Co., Ltd.) (This may be simply referred to as "peptide" hereinafter.)

OVA protein: OVA (EndoFit Ovalbumin: from InvivoGen) (This may be simply referred to as "OVA" hereinafter.)

(5) Culture Medium, Etc.

RPMI (from Nacalai Tesque Inc. RPMI 1640 culture medium (liquid))

Penicillin-Streptomycin Mixed Solution (from Nacalai Tesque Inc.)

FBS (Fetal Bovine Serum, certified, heat inactivated, US origin: from Gibco)

(6) Reagents

EYPC (Egg yolk phosphatidylcholine with no water added: from NOF Corporation, COATSOME NC-50)

Phosphlipid C-test wako (from Wako Pure Chemical Industries, Ltd.): Reagent for phospholipid assay Pyranine (from Tokyo Chemical Industry Co., Ltd.): Fluorescent substance DPX (p-xylene-bis-pyridiniumn bromide: from Molecular Probes Inc.): Quencher Triton-X100 (from Wako Pure Chemical Industries, Ltd.): Surface active agent NBD-PE (1,2-dioleoyl-sn-glycero-3-phosphoethanolamine-N-(7-nitro-2-1,3-benzoxadiazol-4-yl)ammonium: from Avanti Polar Lipids, Inc.)

Rh-PE (1,2-dioleoyl-sn-glycero-3-phosphoethanolamine-N-(lissamine rhodamine B sulfonyl)ammonium: from Avanti Polar Lipids, Inc.): fluorescence labeling lipid Rh-PE (1,2-dioleoyl-sn-glycero-3-phosphoethanolamine-N-(lissamine rhodamine B sulfonyl)ammonium: from Avanti Polar Lipids, Inc.): fluorescence labeling lipid Bio-Rad DC Protein Assay Reagent A, B (from Bio-Rad Laboratories, Inc.): Protein assay kit IsoFlow (from Beckman Coulter, Inc.): Sheath fluid for flow cytometry RBC lysis buffer (from Santa Cruz Biotechnology, Inc.): Buffer for hematolysis of erythrocyte Collagenase for cell dispersion (from Wako Pure Chemical Industries, Ltd.): Reagent for cell dispersion Anti-CD11cFITC (from eBioscience Inc., Anti-Mouse CD11cFITC): Fluorescein isothiocyanate (FITC), labeled antibody Anti-CD80PE (from eBioscience, Inc., Anti-Mouse CD80 (B7-1) PE): R-phycoerythrin (PE), labeled antibody (This may be referred to as CD80PE hereinafter.)

Anti-CD86PE (from eBioscience, Inc., Anti-Mouse CD86 (B7-2) PE): PE labeled antibody (This may be referred to as CD86PE hereinafter.)

Anti-CD40PE (from eBioscience, Inc., Anti-Mouse CD40PE): PE labeled antibody (This may be referred to as CD40PE hereinafter.)

Anti-mouse CD16/32 (from BD Biosciences, Inc.)

Cytofix/Cytoperm (from BD Biosciences, Inc.): cell immobilization-cell membrane permeation kit BD Stain Buffer: Buffer for staining BD GolgPlug: Cell stimulating kit Anti-CD8αPE (from eBioscience, Inc.): PE labeled antibody Mouse IFNγ ELISPOT Set (from BD Biosciences, Inc.)

AEC Substrate Set (from BD Biosciences, Inc.)

Sodium hydrogen carbonate (from Wako Pure Chemical Industries, Inc.)

Sodium carbonate (from Wako Pure Chemical Industries, Inc.)

Secondary antibody (anti-mouse IgG HRP conjugate, from R&D systems, Inc.)

Albumin (Albumin from bovine serum, from Sigma Corporation)

Color development kit for peroxidase (from Sumitomo Bakelite Co., Ltd.)

(7) Animals

C57BL/6N mice, female, (6 to 8 weeks old), were bought from Japan S.L.C, Inc. Experiments were carried out according to the guideline for animal experiments drafted by Terumo Corporation.

<Sample Preparation, Etc.>

MES Buffer

Prepared from MES (25 mM) and NaCl (125 mM). The MES Buffer has a pH value of 7.4, unless otherwise specified.

PBS

Prepared from PBS Tablets (from Takara Bio Inc.). More specifically, PBS was prepared by dissolving 10 pieces of PBS Tablets in distilled water and diluting the solution to 1000 mL. It has a pH of 7.35 to 7.65.

Preparation of MPL Stock Solution

Prepared by dissolution in a 7:3 mixed solvent of chloroform and methanol, so that the concentration was 100 ng/μL. It was further diluted according to need.

RPMI Medium

RPMI medium containing 10% serum was prepared by adding penicillin (100 unit/mL) and streptomycin (100 mg/mL), both as antibiotics. It was supplemented with additional FBS according to need.

<Apparatus Used>

Ultrasonic irradiator: USC-J

Spectrophotometer: FP-6500

Flow cytometer: (FC500; software: CXP Software ver. 2)

UV-vis spectrophotometer: UV-3600

Freeze-dryer: EYELA FREEZE DRYER FDU506

Vacuum pump: GCD 135XA $CO_2$ incubator: MCO20AIC

Separation filter: Amicon Ultra 30K

<Cell Culture>

Cell culture was carried out at 37° C. by using an incubator (MCO20AIC) containing 5% $CO_2$.

(Preparation of Adjuvant Composition and Vaccine Composition)
Production by Preparation Method by Dispersion A mixture was prepared in a 10-mL eggplant-shaped flask from an amphipathic substance (1000 nmol dissolved in methanol (or chloroform), a pH-sensitive compound dissolved in methanol (or chloroform), and MPL stock solution. The resulting mixture was made into thin film by using a rotary evaporator.

With the help of an ultrasonic irradiator, the thus produced thin film was dispersed together with 1.0 mL of MES Buffer (for the release test and the membrane-fusion test) or 1.0 mL of PBS (for the measurement of incorporation rate, the evaluation of stimulus to activate innate immune system, and the immunization of mice) added thereto. In this way there was prepared a dispersion of the adjuvant composition. For preparation of the vaccine composition, the MES Buffer or the PBS was replaced by one which contains a prescribed amount of antigen dissolved therein.

The ratio between the amount of the amphipathic substance and the amount of the pH-sensitive compound was properly adjusted as desired. In the case where a plurality of amphipathic substances are used, adjustments were made so that their total amount is 1000 nmol (which is as desired molar concentration). The amount of the pH-sensitive compound used indicated in the Examples and the explanation of Figures is the amount for 100 nmol of the amphipathic substance used.

Production by Preparation Method by Mixing

A mixture was prepared in a 10-mL eggplant-shaped flask from the amphipathic substance (1000 nmol dissolved in methanol (or chloroform), the pH-sensitive compound dissolved in methanol (or chloroform), and the MPL stock solution. The resulting mixture was made into thin film by means of a rotary evaporator. The thus produced thin film was dispersed at 5 to 35° C. by means of an ultrasonic irradiator together with 0.5 mL of MES Buffer (for the release test and the membrane-fusion test) or 0.5 mL of PBS (for the measurement of incorporation rate, the evaluation of stimulus to activate innate immune system, and the immunization of mice) added thereto. In this way there was prepared a dispersion of the adjuvant composition.

The thus obtained adjuvant composition in dispersion form was incorporated with the same amount of the antigen solution in varied concentrations. In this way there was obtained the vaccine composition in dispersion form.

Production by the Preparation Method by Freeze-Thawing and Freeze-Drying

The adjuvant composition in dispersion form was prepared in the same way as the preparation method by mixing. The dispersion of the adjuvant composition was incorporated with the same amount of the antigen solution in varied concentrations. The resulting solution underwent sequentially freeze-thawing and freeze-drying. The thus obtained freeze-dried product was dispersed again into 1.0 mL of water for injection at 5 to 35° C. In this way there was prepared the dispersion of the vaccine composition.

The freeze-thawing was accomplished by dipping the 10-mL eggplant-shaped flask in cooled methanol, thereby freezing the dispersion, and then dipping the eggplant-shaped flask in distilled water at 5 to 35° C.

Also, the dispersion underwent freeze-drying, which was accomplished by using the freeze dryer (EYELA FREEZE DRYER FDU506) and the vacuum pump (GCD135XA).

In the case where CpG-DNA (CpG-ODN) was used, thin film was produced from a mixture of 1000 nmol of the amphipathic substance and a prescribed amount of the pH-sensitive compound, and the resulting thin film, together with 0.5 mL of PBS, was made into a dispersion by using an ultrasonic irradiator. The resulting dispersion was further incorporated with 0.5 mL of PBS containing a prescribed mount of CpG-DNA and a prescribed mount of antigen dissolved therein. The thus prepared dispersion was used for experiments.

(Preparation of Samples for Comparison)

Samples for comparison were prepared as follows from a dispersion of MPL alone (MPL dispersion), a dispersion of an amphipathic substance alone, and a dispersion of a pH-sensitive carrier alone. They additionally contain a prescribed amount of antigen in the case where they are used to immunize mice.

A 10-mL eggplant-shaped flask with a prescribed amount of amphipathic substance or pH-sensitive carrier dissolved in MPL stock solution or methanol (or chloroform) may be prepared. Then, the content in the flask was made into thin film by means of a rotary evaporator. The thus obtained thin film was dispersed together with 1.0 mL of MES Buffer (for the release test and the membrane-fusion test) or 1.0 mL of PBS (for the measurement of incorporation rate, the evaluation of stimulus to activate innate immune system, and the immunization of mice) added thereto by means of an ultrasonic irradiator. Thus, there were obtained the dispersion of MPL alone, the dispersion of the amphipathic substance alone, or the dispersion of the pH-sensitive carrier alone. For evaluation of the CTL induction rate, PBS containing a prescribed amount of antigen dissolved therein was used.

<Method for Measurement>
(Release Test: Measurement of Leakage)

The leakage was evaluated according to the method described in K. Kono et al., Bioconjugate Chem. 2008 19 1040-1048. The evaluation was performed with the help of EYPC liposomes which contain Pyranine (as a fluorescent substance) and DPX (as a quencher).

EYPC (3000 nmol) dissolved in chloroform was measured and placed in a 10-mL eggplant-shaped flask, and the EYPC was made into thin film with a rotary evaporator. To the flask was added a Pyranine solution (500 µL), which is composed of Pyranine (35 mM), DPX (50 mM), and MES (25 mM), and has pH 7.4. The thin film in the flask was dispersed with the help of an ultrasonic irradiator (USC-J). The resulting dispersion was passed through a porous polycarbonate film having a pore diameter of 100 nm with the help of an extruder, so as to make the particle size uniform. The resulting dispersion underwent substitution of the outer aqueous layer with the help of MES Buffer and G100 column. Thus, there was obtained a dispersion of EYPC liposomes encapsulating the fluorescent substance. The concentration of the lipid was determined with the help of phospholipid C-test Wako, and then it was adjusted with MES Buffer so that phospholipid became 1.0 mmol/L.

The dispersion of EYPC liposomes (with its concentration adjusted) in an amount of 20 µL and the dispersion of a sample for evaluation in an amount of 20 µL were added to MES Buffer (with its pH adjusted) in an amount of 2960 µL. The resulting mixture underwent incubation at 37° C. for 90 or 30 minutes. Values resulting from incubation for 90 minutes are adopted in the Examples, unless otherwise indicated. Finally, fluorescence at Ex416 nm and Em512 nm was measured by means of the spectrometer FP-6500 to monitor the Leakage.

The leakage was calculated assuming that the sheer dispersion of EYPC liposomes has 0% and the dispersion of EYPC liposomes incorporated with 30 µL of 10-fold diluted Triton-X100 has 100%. Specifically, the leakage was calculated from the following formula, L denotes the intensity of fluorescence measured, $L_0$ denotes the intensity of fluorescence of the sheer dispersion of EYPC liposomes containing the fluorescent substance, and $L_{100}$ denotes the intensity of fluorescence of the dispersion of EYPC liposomes incorporated with Triton-X100.

$$\text{Leakage (\%)} = \frac{(L - L_0)}{L_{100} - L_0} \times 100 \quad \text{[Math 3]}$$

(Membrane-Fusion Test: Measurement of Fusion (Membrane-Fusion))

The Fusion (membrane-fusion) was evaluated according to the method described in K. Kono et al. Biomaterials 2008 29 4029-4036, by means of FRET (Fluorescence Resonance Energy Transfer). The fluorescence labeling employed NBD-PE and Rh-PE.

A dispersion of EYPC liposomes (with double fluorescence labeling) was prepared as follows. First, there was produced thin film from EYPC (1000 nmol) containing 0.6 mol % of NBD-PE and Rh-PE. Then, the thin film was dispersed together with MES Buffer (1.0 mL) added thereto by means of an ultrasonic irradiator (USC-J). Finally, the resulting dispersion was passed through a polycarbonate film having a pore diameter of 100 nm by means of an extruder.

The dispersion of EYPC liposomes with double fluorescence labeling (20 μL) and the dispersion of sample for evaluation (20 μL) were added to the pH-adjusted MES Buffer (2960 μL), followed by incubation at 37° C. for 60 minutes. The resulting liquid was measured for fluorescent spectrum at 500 nm to 620 nm (with excitation light at 450 nm) by means of the spectrophotometer (FP-6500). There was obtained the ratio between the fluorescence intensity at 520 nm and the fluorescence intensity at 580 nm.

The fusion rate was calculated on the following assumptions. The fluorescence intensity ratio of the dispersion of double fluorescence labeled EYPC liposomes and the amphipathic substance, which have undergone incubation, is 0%. The fluorescence intensity ratio of the dispersion of double fluorescence labeled EYPC liposomes and the dispersion of sample for evaluation, which have undergone methanol treatment, is 100%. The methanol treatment comprises or consists of dissolving the dispersion of double fluorescence labeled EYPC liposomes and the dispersion of sample for evaluation in methanol, making the resulting solution into thin film by means of a rotary evaporator, and dispersing the thin film into MES Buffer (3.0 mL) by means of the ultrasonic irradiator.

More specifically, the fusion rate was calculated from the following formula, wherein R denotes the intensity ratio of fluorescence measured, $R_0$ denotes the intensity ratio of fluorescence of the dispersion of double fluorescence labeled EYPC liposomes and the amphipathic substance, both of which underwent incubation, and $R_{100}$ denotes the intensity ratio of fluorescence of the dispersion of double fluorescence labeled EYPC liposomes and the dispersion of sample for evaluation, both of which underwent methanol treatment.

$$\text{Fusion rate (\%)} = \frac{(R - R_0)}{R_{100} - R_0} \times 100 \quad \text{[Math 4]}$$

(Measurement of Incorporation Rate)

The incorporation rate was evaluated as follows on the basis of the fact that the dispersion in which the antigen exists alone passes through the filter and the dispersion in which the antigen is supported on or contained in the adjuvant composition does not pass through the filter.

The dispersion containing the adjuvant and the antigen was passed through the Amicon Ultra 30K Filter at room temperature, at 7000 rpm, and for 10 minutes.

The incorporation rate was calculated by determining the antigen before and after filtration. Before and after filtration, the antigen underwent color reaction by Lowry method and was tested for absorbance at 750 nm by means of the spectrometer UV-vis. The incorporation rate was calculated from the following formula. The test for color reaction was performed by using 200 pt. In the following formula, $A_{before}$ denotes absorbance observed before filtration, due to color reaction caused by the antigen in the dispersion; $A_{after}$ denotes absorbance observed after filtration, due to color reaction caused by the antigen in the dispersion; and $A_{buffer}$ denotes absorbance in the case where PBS was used. In other words, the numerator represents the antigen which did not pass through the filter or the antigen which was incorporated into (supported on or contained in) the adjuvant composition.

$$\text{Incorporation rate (\%)} = [(A_{before} - A_{buffer}) - (A_{after} - A_{buffer})]/(A_{before} - A_{buffer}) \times 100 \quad \text{[Math 5]}$$

(Evaluation of Stimulus to Activate Innate Immune System)

The evaluation of stimulus to activate innate immune system was performed as follows.

A spleen was harvested from C57BL/6N mice. The harvested spleen was injected with 500 μL of collagenase solution, 2 mg/mL (prepared with RPMI medium) followed by incubation at 37° C. for 30 minutes. The spleen was made into cell suspension by treatment with BD Falcon cell strainer. The cells underwent hemolysis with RBC lysis buffer, followed by washing with RPMI medium. The cells were dispersed into RPMI medium, and the number of cells was counted. The cells were used for the subsequent procedure.

The cells were inoculated into a 96-well dish such that $1.0 \times 10^6$ cells/100 μL. The cell dispersion was given 100 μL of RPMI medium containing a dispersion of different kind, followed by incubation overnight. These procedures were performed by using serum-free RPMI medium.

The cells were recovered and washed with BD stain buffer. Then, the cells underwent incubation together with Anti-CD11cFITC, 0.25 μg/100 μL (4° C. for 30 minutes), so that the cells were stained. After washing, the cells underwent again incubation with Anti-CD80PE, Anti-CD86PE, or Anti-CD40PE, 0.25 μg/100 μL (4° C. for 30 minutes), so that the cells were stained. After washing at least more than three times, the cells were evaluated by using the flow cytometer (Cytomics FC500, Software: CXP software ver. 2).

(Immunization of Mice)

Administration (100 μL/head) was performed by subcutaneous injection at one position on the back under anesthesia. The dose of the amphipathic substance was 100 nmol/head; the dose of the pH-sensitive compound was 10 to 640 nmol/head; MPL content was 0.0227 to 22.7 nmol/head; and the amount of the antigen was 3.2 to 400 μg/head. For evaluation of cell-mediated immunity, administration was performed once and the assay was performed seven days after administration. For evaluation of humoral immunity, administration was performed twice. The second administration was performed 14 days after the first administration, and assay was performed seven days after the second administration.

(Preparation of Dispersion of Cells from Mice's Spleen)

The mice were sacrificed on the seventh day after the last administration and had its spleen harvested. The spleen was given RPMI medium (3.0 mL) containing 10% serum and then treated by the BD Falcon cell strainer. Thus there was obtained a suspension of cells. The cells underwent hemolysis with RBC lysis buffer, followed by washing with RPMI medium containing 10% serum. The cells were dispersed into RPMI medium containing 10% serum. The number of cells was counted. Thus there was obtained a dispersion of spleen cells.

(Evaluation of CTL Induction Rate—ICS Method)

The dispersion of spleen cells was inoculated into the medium containing 10% serum such that $1.0 \times 10^6$ cells/100 µL. For restimulation of the antigen, 10% serum-containing RPMI medium (100 µL) containing OVA peptide (40 µg/mL) was added, followed by incubation for three hours. Then, BD GolgiPlug was added such that its concentration was 0.2 µL/100 µL. Cell culture was performed overnight. In the case where the restimulation was not given, a 10% serum-containing RPMI medium not containing OVA peptide was used.

The cells were recovered and washed with BD stain buffer. Then, the cells underwent incubation together with Anti-mouse CD16/32 at 4° C. for 10 minutes. After washing, the cells were stained with Anti-CD8αPE (at 4° C. for 30 minutes), followed by washing again. Then the cells were permeabilized with Cytofix/Cytoperm. After washing, the cells were stained with Anti-IFNγFITC (at 4° C. for 30 minutes). After washing equal to or more than three times, the cells were evaluated by using the flow cytometer (Cytomics FC500, Software: CXP software ver. 2). CTL induction rate was calculated in terms of the ratio between the IFNγ secreting cells and the total CD8 positive cells.

(ELIspot Method)

The ELIspot method was practiced by using the Mouse IFNγ ELISPOT Set. One day before cell inoculation, the 96-well ELIspot plate was allowed to adsorb the detection antibody attached to the kit, so that the plate was made ready for use. The plate made in this manner was washed with 10% serum-containing RPMI medium and then given 10% serum-containing RPMI medium in an amount of 200 µL. The plate was allowed to stand at 37° C. for two hours for blocking. The plate was washed with 10% serum-containing RPMI medium. In the case where the antigen undergoes restimulation, the plate was given 10% serum-containing RPMI medium (100 µL) containing OVA peptide (40 µg/mL). In the case where the antigen does not undergo restimulation, the plate was given 10% serum-containing RPMI medium (100 µL). The foregoing plate was inoculated with the dispersion of spleen cells so that there existed a prescribed number of cells. Finally, the 10% serum-containing RPMI medium was added so that the total amount per well was adjusted to 200 µL. After that, cell culture was performed for two nights so that the plate assumed a color.

The procedure for the plate to assume a color conformed to the protocol described in the Mouse IFNγ ELISPOT Set and the AEC Substrate Set.

(Measurement of Antibody Titer)

Serum was obtained by blood collection which was performed seven days after the second administration. Block buffer was prepared by dissolving albumin (5 g) in PBS (500 mL). Coating buffer was prepared by dissolving sodium hydrogen carbonate (1.47 g) and sodium carbonate (0.80 g) in water (500 mL). Washing of the plate was performed with PBS (500 mL) added with Tween 20 (2.5 mL).

In the coating buffer was dissolved OVA protein, and the resulting solution as added to the 96-well plate such that the amount was 0.1 µg/well (100 µL). After standing at 37° C. for two hours, the coating buffer was replaced by the Block buffer. After standing overnight at 4° C., the plate was washed, and then each well was given 100 µL of serum diluted at a prescribed ratio. After standing at 37° C. for two hours, the plate was washed, and each well was given 100 µL of secondary antibody solution diluted 1000 fold. After standing at 37° C. for two hours, the plate was washed and allowed to develop color with the help of the coloring kit for peroxidase. In this way there was obtained the antibody titer.

[Evaluation]

Various evaluations were performed by using the dispersions prepared according to the above-mentioned methods.

(1) Induction of Immune Response

The induction of cell-mediated immunity was reviewed. The amphipathic substance in the adjuvant composition is DLPC, and the pH-sensitive compound in the adjuvant composition is deoxycholic acid (160 nmol). The MPL content is 0.227, and the model antigen is OVA peptide (occasionally referred to as "peptide" hereinafter). The MPL content denotes the amount (in nmol) of MPL relative to the amount (100 nmol) of the amphipathic substance. The amount of the pH-sensitive compound denotes the amount relative to the amount (100 nmol) of the amphipathic substance. The adjuvant composition was prepared by dispersion.

Samples used for comparison include a solution of the peptide alone, a dispersion of the pH-sensitive carrier (DLPC-deoxycholic acid) and the peptide, and a solution of incomplete Freund's adjuvant (IFA) and peptide. The above-mentioned solution or dispersion was subcutaneously administered once to the back of C57BL/6N mice. The number of IFNγ-secreting cells in the spleen was counted, and the CTL induction was evaluated.

Evaluation was typically accomplished by the ELIspot method. The result of evaluation is depicted in FIGS. 2(A)-(C). This result was obtained under the condition of $2 \times 10^6$ cells/well. FIG. 2(A) represents a graph depicting the number of IFNγ spots. FIG. 2(B) represents the spots formed in the case where peptide is used alone. FIG. 2(C) represents the spots formed in the case where peptide is used in combination with MPL-containing DLPC-deoxycholic acid complex (adjuvant composition). The sample with peptide alone gave the equivalent number of spots as the untreated sample, with no CTL induction (FIG. 2(A)). The sample with MPL-free DLPC-deoxycholic acid complex also gave the equivalent number of spots as the untreated sample, with no CTL induction (FIG. 2(A)). This is a very interesting result. It suggests that the CTL induction needs stimulus to activate innate immune system.

By contrast, the sample with a complex of MPL-containing DLPC-deoxycholic acid (which is the adjuvant composition) gave a larger number of spots than the untreated sample or the sample containing peptide alone (FIGS. 2(B) and 2(C)). The fact that the number of spots is almost equal to that in the positive control (or IFA) suggests that the adjuvant composition induced CTL as strongly as IFA. In view of the fact that IFA is widely used in clinical studies as the adjuvant to induce CTL, the adjuvant of the present invention, which is as active as IFA, is expected to be effective for clinical use.

(2) Comparison with MPL

It is known that MPL activates innate immune system and functions as an adjuvant even when used alone. It is also known that MPL induces cell-mediated immunity. Thus, a comparison was made as to the induction of cell-mediated immunity between MPL used alone and MPL used in combination with a pH-sensitive carrier in the form of the adjuvant composition. Each of the MPL and the adjuvant composition is administered together with an antigen. The antigen is peptide (80 μg), and the MPL is that which contains MPL in an amount of 0.227 mol or in an amount equivalent to that mentioned above. The adjuvant composition is a dispersion of the MPL-containing DLPC-deoxycholic acid complex, as mentioned in (1) above. The above-mentioned solution or dispersion was subcutaneously administered once to the back of C57BL/6N mice, and the CTL induction rate was obtained according to the ICS method. The CTL induction rate is expressed in terms of the ratio of the IFNγ-secreting cells to the total CD8 positive cells in a specific area which is hardly affected by dead cells (IFNγ-secreting cells/total CD8 positive cells).

Figure 3A:
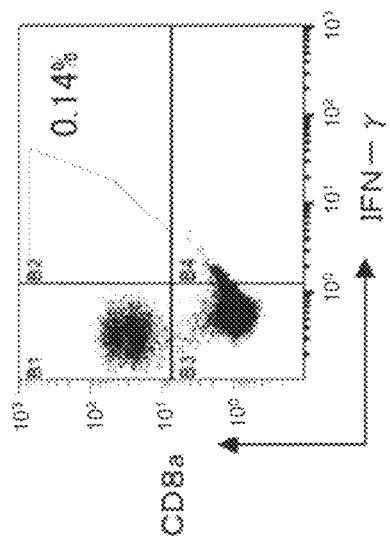
FIGS. 3(A)-3(C) depict the result obtained in the case where the CTL induction rate was evaluated by Intracellular Cytokine Staining (ICS) method.
Figure 3B:
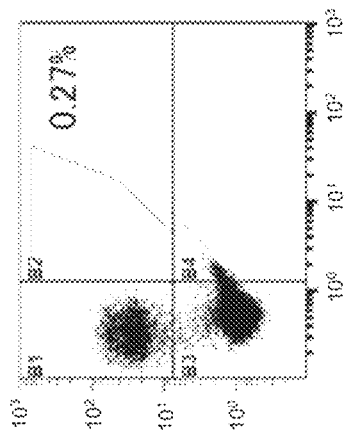
Figure 3C:
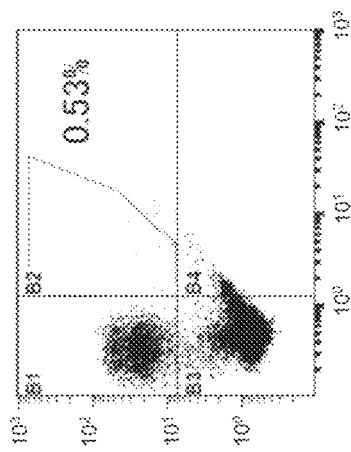

The results are depicted in FIGS. 3(A)-3(C). FIG. 3(A) represents the result in the case where a solution of peptide alone was use. FIG. 3(B) represents the result in the case where peptide and a dispersion of MPL alone were used. FIG. 3(C) represents the result in the case where an MPL-containing DLPC-deoxycholic acid complex (as the adjuvant composition) was used.

In the case where peptide and MPL dispersion were used, the CTL induction rate is 0.27%, which is slightly higher than that (0.14%) in the case where peptide was used alone, as depicted in FIGS. 3(A) and 3(B). Also, in the case where peptide and MPL-containing DLPC-deoxycholic acid complex were used, the CTL induction rate is 0.53%, which is higher than that in the case where MPL dispersion was used, as depicted in FIGS. 3(B) and 3(C). In spite of the fact that the same antigen was used, the pH-sensitive carrier containing MPL (as the adjuvant composition) gave a higher CTL induction rate than the MPL dispersion. This result suggests that the adjuvant composition produces the effect of enhancing the CTL induction.

The foregoing results demonstrate that the effect of CTL induction by MPL is enhanced by the pH-sensitive carrier. A probable reason for this is that the pH-sensitive carrier promotes the membrane-disruption function, thereby enabling the delivery of the antigen to the cytosol, and enhances the effect of CTL induction through promotion of cross-presentation.

(3) Discussion on Method for Preparation

The vaccine composition is composed of the antigen and the adjuvant composition. The discussion on the method for the preparation of the vaccine composition will help to improve the adjuvant composition in its effect of inducing CTL. This idea led to the following discussion.

Several vaccine compositions in dispersion form were prepared by the preparation method by dispersion, the preparation method by mixing, and the preparation method by freeze-thawing and freeze-drying. The resulting vaccine compositions were examined for the CTL induction rate in the similar way as mentioned in (2) above. The amphipathic substance is DLPC, and the pH-sensitive compound is deoxycholic acid (160 nmol). The content of MPL is 0.227, and the antigen is peptide (80 μg).

The results are depicted in FIGS. 4(A)-4(C). FIG. 4(A) depicts the result in the case where an MPL-containing DLPC-deoxycholic acid complex was used (prepared by the preparation method by dispersion). FIG. 4(B) depicts the result in the case where an MPL-containing DLPC-deoxycholic acid complex was used (prepared by the preparation method by mixing). FIG. 4(C) depicts the result in the case where an MPL-containing DLPC-deoxycholic acid complex was used (prepared by preparation method by freeze-thawing and freeze-drying).

All of the vaccine compositions prepared by the preparation method by dispersion, the preparation method by mixing, and the preparation method by freeze-thawing and freeze-drying gave a higher CTL induction rate than the vaccine composition containing MPL alone (0.53%, 0.54%, 1.47%; FIGS. 4(A)-4(C)). These results suggest that the adjuvant composition in each vaccine composition produces the effect of enhancing the CTL induction regardless of the method for preparation. Particularly, the vaccine composition prepared by the preparation method by freeze-thawing and freeze-drying gave a very high CTL induction rate. This result apparently suggests that the preparation method by freeze-thawing and freeze-drying yields the adjuvant composition (in the vaccine composition) which produces the effect of greatly enhancing the CTL induction rate (FIG. 4(C)).

(4) Evaluation of Incorporation Rate

It has been depicted in (3) above that the vaccine composition prepared by the preparation method by freeze-thawing and freeze-drying gave a very high CTL induction rate.

Figure 5A:
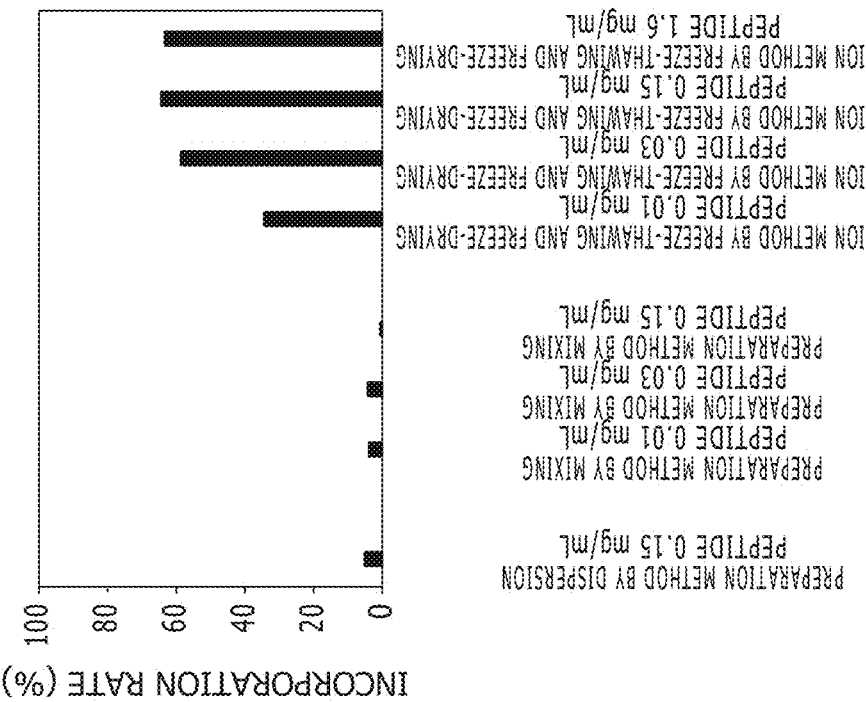
FIGS. 5(A)-(C) depict the result of evaluation of incorporation rate.
Figure 5B:
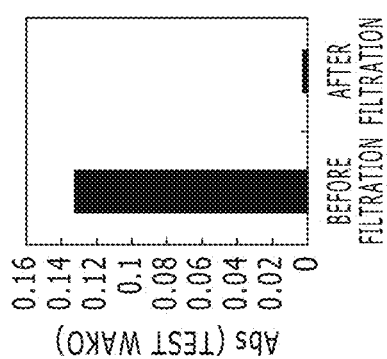

Without wishing to be bound by any particular theory, a probable reason for this is that the incorporation of the antigen into the adjuvant composition improves the efficiency of delivery to the cytosol, which in turn produces the effect of greatly enhancing the CTL induction rate. Thus, the incorporation rate of the antigen into the adjuvant composition was evaluated. First, the system for evaluation was verified. In the case of solution containing peptide alone, there was no change in absorbance measured by Lowry method before and after filtration, and the peptide was not caught by the filter (FIG. 5(A)). On the other hand, in the case of solution containing peptide test Wako, absorbance completely disappeared after filtration (FIG. 5(B)). This suggests that the adjuvant composition is caught by the filter. The foregoing suggests that the evaluation system mentioned herein permits the evaluation of the incorporation rate of the antigen into the adjuvant composition.

Figure 5C:
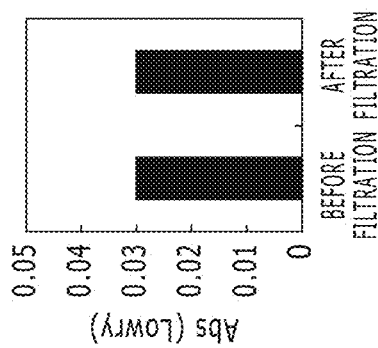

FIG. 5(C) depicts the result of evaluation of the incorporation rate in the case where each of the vaccine compositions were prepared by by dispersion, by mixing, or by freeze-thawing and freeze-drying. The dispersion resulted in a low incorporation rate (approximately 5%), and mixing also resulted in a low incorporation rate. By contrast, the preparation method involving freeze-thawing and freeze-drying resulted in a high incorporation rate (approximately 60% at the maximum) (FIG. 5(C)). This suggests that the vaccine composition prepared by the preparation method by freeze-thawing and freeze-drying is composed of the adjuvant composition and the antigen which are integrated with each other in a high ratio. The amphipathic substance is DLPC, and the pH-sensitive compound is deoxycholic acid (160 nmol). The content of MPL is 0.227.

It is assumed that the preparation method by freeze-thawing and freeze-drying realized a high incorporation rate for the antigen and this led to a high probability that the adjuvant composition and the antigen are integrated into the same endosome. The result of this assumption is that the membrane disruptive function promoting effect efficiently increases the delivery to the cytosol, which further leads to the high CTL induction rate as depicted in the result mentioned in (3) above.

(5) Regarding Amount of MPL

The result mentioned in (1) above depicts that the instance in which the MPL-free DLPC-deoxycholic acid complex was used did not bring about the CTL induction. This suggests that a substance to activate innate immune system is necessary if the pH-sensitive carrier is to be utilized as the adjuvant composition. In order to test the intensity of stimulus to activate innate immune system, ex vivo experiments (which use mice spleen cells) were conducted according to the reports in Nature Materials 2011 vol. 10(3) 243-251 and Cancer Res. 2011 71 2858-2870. In this way the amount of MPL required was sought.

First, the system for evaluation was verified.

FIGS. 6(A)-6(F) depicts the result of verification of the system for evaluation. FIG. 6(A) depicts the result of flow cytometry in which the cultured mice spleen cells were evaluated without staining. This indicates the region of dead cells. FIGS. 6(B) and 6(C) depict respectively how much the expression of CD80 is enhanced when the cultured mice spleen cells are incorporated with PBS alone and LPS in a concentration of 400 ng/mL. FIG. 6(D) depicts the result obtained when LPS is added in varied concentrations. FIGS. 6(E) and 6(F) depict the result of the increase in expression of CD86 and CD40 which are other costimulatory molecules.

It is noted that the fluorescence intensity of CD80PE increases in proportion to the amount of LPS in the region monitored (FIG. 6(B) to 6(D)). It is also noted that the fluorescence intensity of CD86 and CD40, which are another costimulatory molecules, increases in the same way as above (FIGS. 6(E) and 6(F)). The foregoing verifies that the evaluation system mentioned herein is capable of evaluating the intensity of stimulus to activate innate immune system.

Figure 7C:
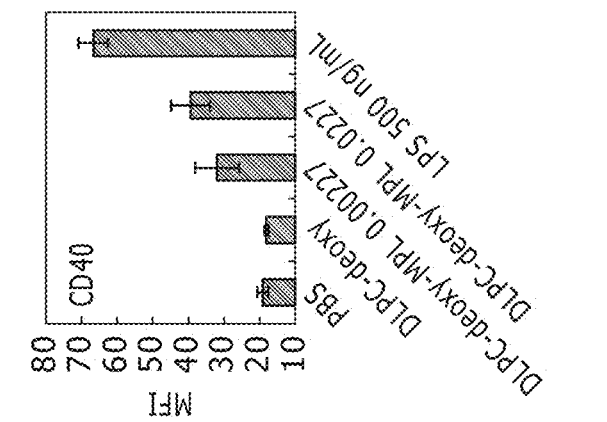
FIG. 7(C) depicts the result of evaluation of the enhanced expression of CD40 as another indicator.
Figure 7B:
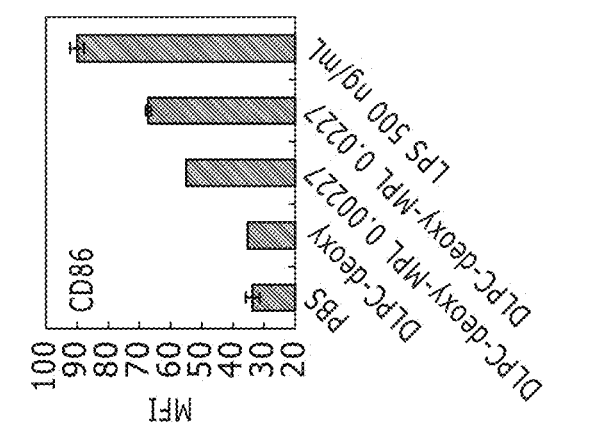
FIG. 7(B) depicts the result of evaluation of the enhanced expression of CD86 as another indicator.
Figure 7A:
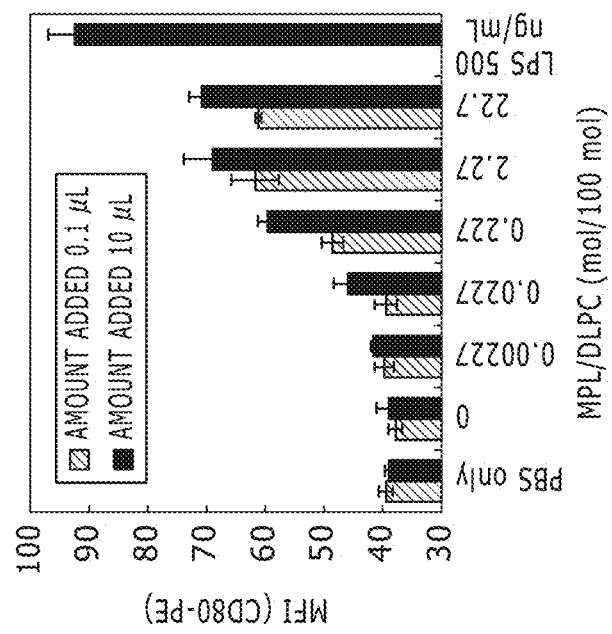
FIG. 7(A) depicts the result of evaluation of the enhanced expression of CD80.

Next, an evaluation was made on the stimulus to activate innate immune system by the adjuvant composition, with the amount of MPL varied appropriately. The results are depicted in FIGS. 7(A)-7(C). The amphipathic substance and the pH-sensitive compound in the adjuvant composition are respectively DLPC and deoxycholic acid (160 nmol). The sample for comparison was prepared from PBS, pH-sensitive carrier (DLPC-deoxycholic acid) in dispersion form, and lipopolysaccharide (LPS) in solution form.

FIG. 7(A) depicts the result of evaluation for increase in expression of CD80. FIGS. 7(B) and 7(C) depict the result of evaluation for increase in expression of CD86 and CD40 as other indicators. The MPL-free DLPC-deoxycholic acid complex (added in an amount of 0.1 μL or 10 μL) gave the fluorescence intensity equivalent to that in the case where PBS was added alone. This indicates the absence of stimulus to activate innate immune system (FIG. 7(A)). On the other hand, it was found that the fluorescence intensity increases and the stimulus to activate innate immune system also increases in proportion to the MPL content (FIG. 7(A)). In the case where the MPL content is 0.00227, the value of MFI (fluorescence intensity) is 41.6. This value is larger than the MFI (39.1) in the case where PBS is used alone and the MFI (38.8) of the pH-sensitive carrier without MPL. In the case where the MPL content is 2.27 or 22.7, the value of MFI is 69.1 or 70.9, respectively. This indicates that the stimulus to activate innate immune system is close to the point of saturation (The value depicted in FIG. 7(A) is that in the case where the amount added is 10 μL.).

The increase of expression of CD40 and CD86, which are other costimulatory molecules, suggests that these adjuvant compositions certainly possess the stimulus to activate innate immune system (FIGS. 7(B) and 7(C)).

(6) Regarding Enhancement of Cell-Mediated Immunity and Activation of Innate Immune System This section is intended to verify the relationship between the enhancement of cell-mediated immunity and the activation of innate immune system.

First, the MPL-free DLPC-deoxycholic acid complex which did not induce CTL as mentioned in (1) above was found to have no stimulus to activate innate immune system as mentioned in (5) above. This is depicted in more detail in FIG. 8(A). It is to be noted that the fluorescence intensity of CD80PE does not exceed that of PBS even though the MPL-free DLPC-deoxycholic acid complex increases in amount from 0.5 μL to 50 μL. This suggests that the MPL-free DLPC-deoxycholic acid complex does not have stimulus to activate innate immune system (FIG. 8(A)).

On the other hand, the adjuvant composition, which produced the effect of enhancing CTL induction as mentioned in (2) above, has the MPL content of 0.227, and it apparently has stimulus to activate innate immune system as mentioned in (5) above. This suggests a relationship between the enhancement of cell-mediated immunity and the activation of innate immune system.

Figure 8B:
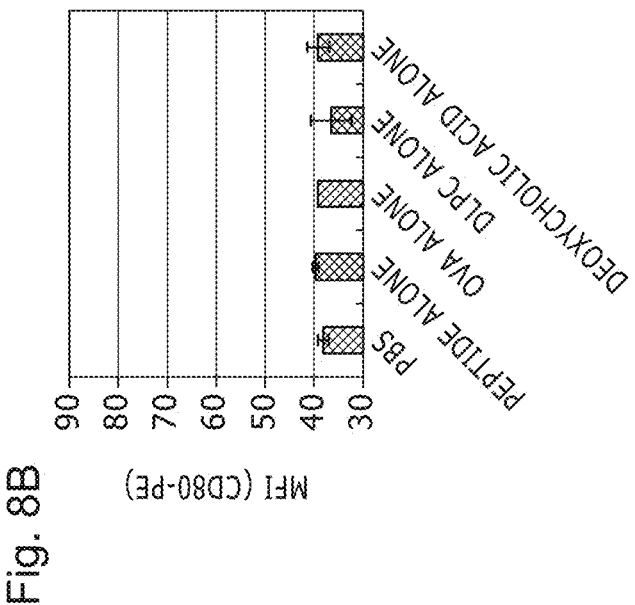
FIGS. 8(A)-8(B) depict the result of examination for the presence or absence of the stimulus to activate innate immune system in various materials.
Figure 8A:
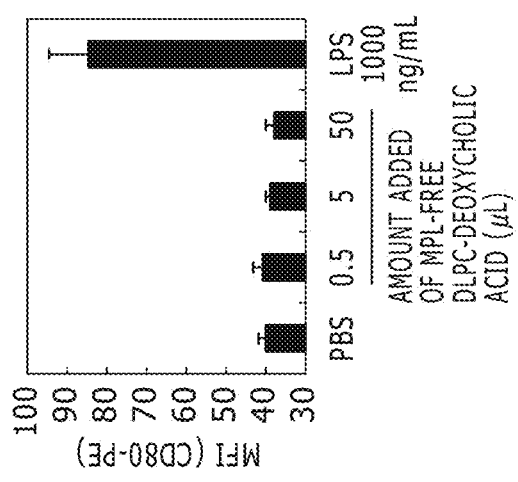

FIG. 8(B) depicts the result obtained when cultured mice spleen cells were given a solution (5 μL) of various samples and examined for the enhanced expression of CD80 (activation of innate immune system). Each solution contains 800 μg/mL each of peptide and OVA, 1000 nmol/mL of DLPC alone, and 1600 nmol/mL of deoxycholic acid alone.

In the case where peptide, OVA, DLPC, and deoxycholic acid were added alone, the fluorescence intensity of CD80PE remained unchanged from that in the case where PBS was added. This suggests the absence of stimulus to activate innate immune system (FIG. 8(B)).

Figure 9A:
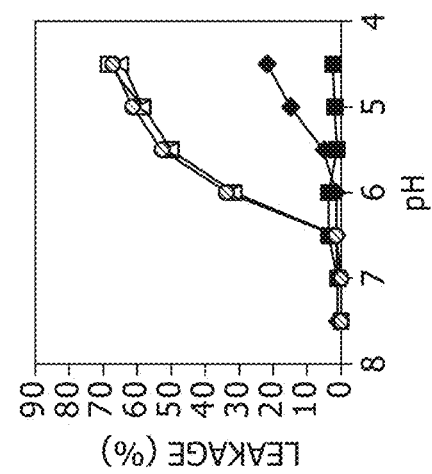
FIG. 9(A) depicts the leakage in the case where MPL is administered in an amount equivalent to the MPL content which is 0.227 mol.
Figure 9B:
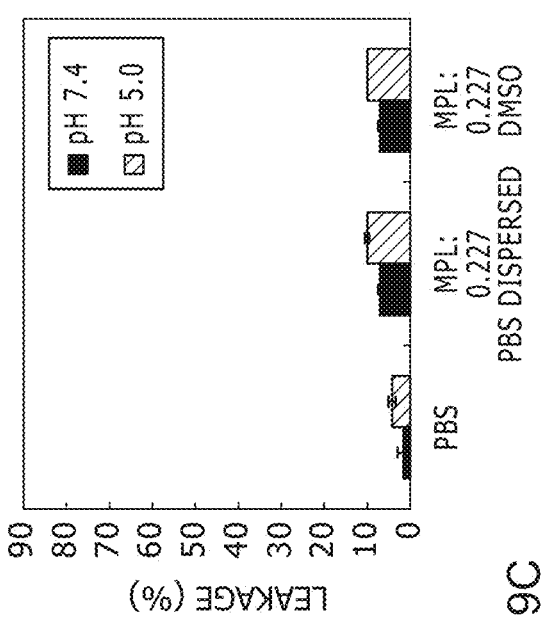
FIG. 9(B) depicts the leakage (at varied pH values) of the MPL-containing DLPC-deoxycholic acid complex.
Figure 9C:
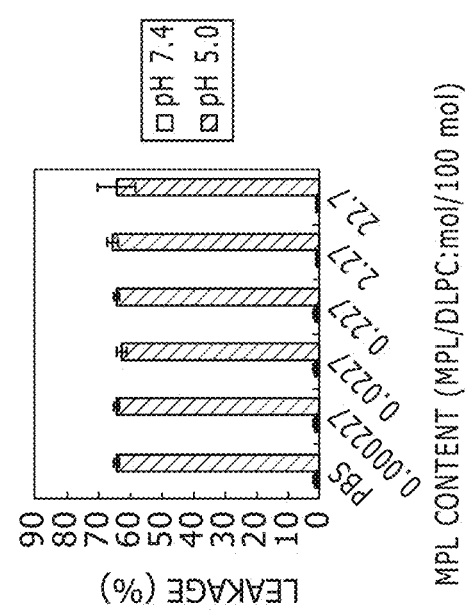
FIG. 9(C) depicts the result of the leakage (at pH 7.4 and pH 5.0) of the DLPC-deoxycholic acid complex, with the MPL content varied.

(7) Influence on Membrane Disruptive Function Promoting Effect (7-1) Influence of MPL Investigations were made as to the influence of MPL content on the membrane disruptive function promoting effect possessed by the adjuvant composition. The results are depicted in FIGS. 9(A)-9(C). FIG. 9(A) depicts the leakage in the case where MPL (in an amount equivalent to the MPL content of 0.227 mol) is added to the evaluation system for the release test. FIG. 9(B) depicts the leakage for MPL-containing DLPC-deoxycholic acid complex at varied pH values. FIG. 9(C) depicts the leakage for DLPC-deoxycholic acid complex containing MPL in varied amount at pH 7.4 and pH 5.0.

An investigation was performed to see whether the leakage increases at a low pH value when MPL (dispersed in PBS or DMSO) is added to cuvette. In all the cases of investigation, the result in all the cases was equivalent to that in the case where PBS was used alone (FIG. 9(A)). This suggests that MPL has no ability to bring about the release.

Several adjuvant compositions were prepared in which the pH-sensitive carrier contains MPL in varied amount, and they were examined for the leakage at various pH values. Even in the case where the MPL content is 0.227 or 2.27, the leakage at each pH value coincided with that in the case where the normal pH-sensitive carrier (DLPC-deoxycholic acid complex) was used (FIG. 9(B)). This suggests that the MPL content has only little influence on the pH value suitable for the membrane disruptive function promoting effect. The influence of MPL content over a broad range was investigated by monitoring the leakage at pH 5.0. It was found that, even in the case where the MPL content is 22.7, the observed leakage remained unchanged from that in the case where an normal pH-sensitive carrier (with MPL content=0) is used (FIG. 9(C)). It was confirmed again that the MPL content influences only little on the membrane disruptive function promoting effect. Without wishing to be bound by any particular theory, a probable reason for this is that the amount of MPL is so small relative to the amphipathic substance in the pH-sensitive carrier that MPL has only little influence on the membrane disruptive function promoting effect.

(7-2) Influence of Method for Preparation

Figure 10:
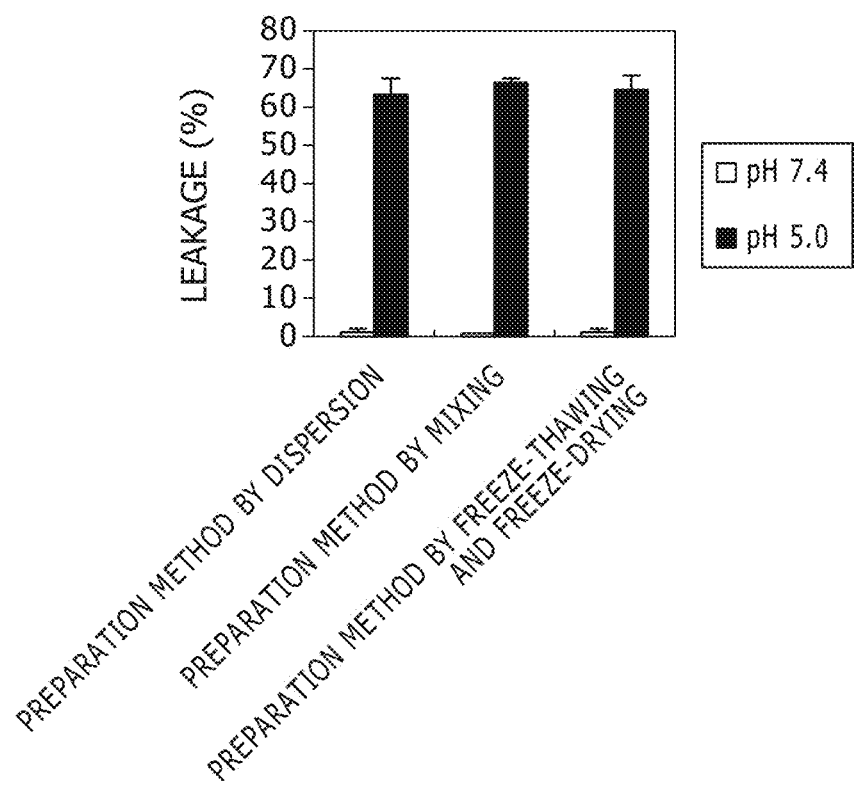
FIG. 10 depicts the result of examination for the leakage (at pH 7.4 and pH 5.0) of the vaccine composition which was prepared by dispersion, by mixing, or by freeze-thawing and freeze-drying.

An investigation was made as to how the method for preparing the vaccine composition (composed of the antigen and the adjuvant composition) influences the membrane disruptive function promoting effect. FIG. 10 depicts the leakage (at pH 7.4 and pH 5.0) of the vaccine composition prepared by the preparation method by dispersion, the preparation method by mixing, or the preparation method by freeze-thawing and freeze-drying. In this vaccine composition, the amphipathic substance is DLPC and the pH-sensitive compound is deoxycholic acid. The content of MPL is 0.227 and the amount of complex product is 160 nmol. The amount of peptide is 15 μg.

All the vaccine compositions, regardless of the method for preparation, gave the similar leakage at pH 7.4 and pH 5.0. This suggests that the method for preparing the vaccine composition does not influence the membrane disruptive function promoting effect (FIG. 10).

(7-3) Influence by Amount of Complex Product in pH-Sensitive Compound

Figures 11A, 11B, 11C:
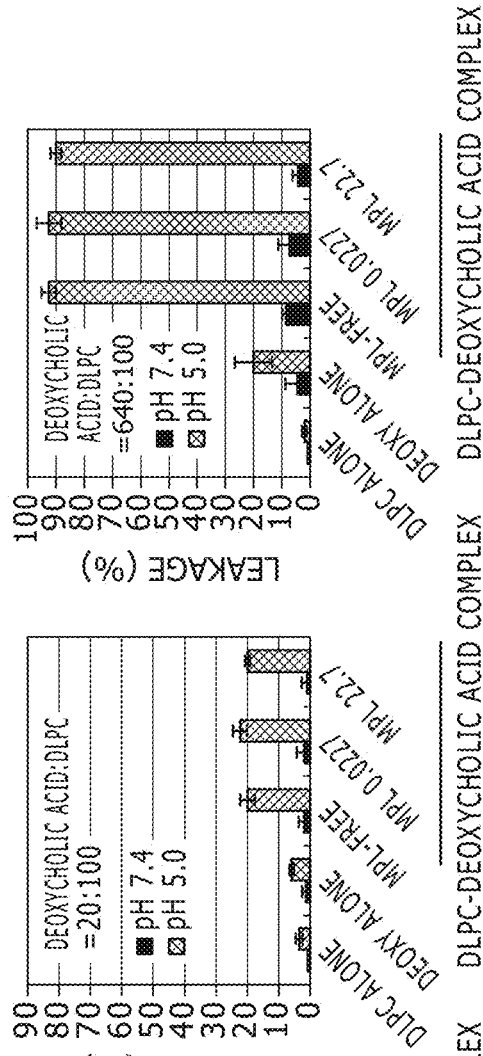
FIGS. 11(A)-11(C) depict the result of examination for the influence of MPL content on the adjuvant composition's membrane disruptive function promoting effect, with the amount of deoxycholic acid varied.

FIGS. 11(A)-11(C) depict the results of an investigation which was made as to how much the MPL content influences the adjuvant composition's membrane disruptive function promoting effect which varies depending on the amount of complex product of deoxycholic acid. The amphipathic substance in the adjuvant composition is DLPC, and the amount of complex product of deoxycholic acid is 10 nmol, 20 nmol, and 640 nmol in FIGS. 11(A), 11(B), and 11(C), respectively. The content of MPL is 0.0227 and 22.7. The samples for comparison are DLPC alone, deoxycholic acid alone, and pH-sensitive carrier (not containing MPL). The leakage was measured at pH 7.4 and pH 5.0.

First, the adjuvant composition not containing MPL (the pH-sensitive carrier; indicated as MPL-free in the figure) produced the membrane disruptive function promoting effect regardless of the amount of complex product (FIGS. 11(A)-11(C)). Next, the adjuvant compositions in which the MPL content is 0.0227 and 22.7 gave the leakages similar to each other or equivalent to those of the MPL-free adjuvant composition at both pH 7.4 and pH 5.0 (FIG. 11(A)). Also, similar results were found for the adjuvant composition in which the amount of complex product was 20 and 640 (FIGS. 11(B) and 11(C)). These results suggest that the content of MPL does not influence the adjuvant composition's membrane disruptive function promoting effect regardless of the amount of complex product.

It was confirmed that the membrane disruptive function promoting effect is not influenced by the MPL content regardless of difference in the amount of complex product of the pH-sensitive compound (FIG. 11).

(7-4) Influence by Kind of Amphipathic Substance or pH-Sensitive Compound

An investigation was made as to the influence of the amphipathic substance of different kind and the pH-sensitive compound of different kind on the adjuvant composition's membrane disruptive function promoting effect.

Tables 1 and 2 depict the result of evaluation of the membrane-disruption function of the adjuvant composition which was prepared from the amphipathic substance of different kind, and the result of evaluation of the membrane-disruption function of the adjuvant composition which was prepared from the pH-sensitive compound of different kind.

TABLE 1

The membrane disruptive function promoting effect of adjuvant composition prepared from amphipathic substance of different kind

| pH-sensitive substance or amphipathic substance | Alone | | Complex with deoxycholic acid | | | |
|---|---|---|---|---|---|---|
| | | | MPL: 0 | | MPL: 0.227 | |
| | pH 7.4 | pH 5.0 | pH 7.4 | pH 5.0 | pH 7.4 | pH 5.0 |
| Deoxycholic acid | 1.0 ± 0.1 | 12.9 ± 1.6 | — | — | — | — |
| DLPC | 1.8 ± 1.2 | 5.5 ± 0.9 | 0.6 ± 0.2 | 58.6 ± 0.5 | 0.6 ± 0.1 | 63.6 ± 6.4 |
| DDPC | 17.4 ± 0.1 | 37.1 ± 1.3 | 24.3 ± 4.5 | 92.7 ± 5.3 | 27.7 ± 3.1 | 92.6 ± 1.9 |
| Tween 20 | 70.4 ± 3.9 | 74.0 ± 2.0 | 63.7 ± 1.9 | 87.7 ± 2.8 | 75.3 ± 2.2 | 93.9 ± 1.6 |
| Tween 80 | 5.0 ± 1.4 | 9.8 ± 1.3 | 5.5 ± 1.3 | 34.5 ± 5.6 | 3.7 ± 1.3 | 34.2 ± 4.5 |
| Peg10 castor oil | 1.0 ± 0.1 | 4.6 ± 0.7 | 2.1 ± 0.3 | 24.9 ± 1.7 | 1.4 ± 0.5 | 30.0 ± 0.9 |
| Span 80 | 6.1 ± 0.6 | 18.1 ± 1.0 | 1.6 ± 0.4 | 36.3 ± 1.2 | 1.7 ± 0.3 | 34.9 ± 1.8 |
| α-tocopherol | 5.5 ± 0.3 | 10.6 ± 1.3 | 10.6 ± 0.5 | 51.3 ± 2.6 | 2.4 ± 0.5 | 43.5 ± 10.9 |
| DLPC:EYPC (100:150) | 1.5 ± 0.2 | 2.4 ± 0.1 | 0.8 ± 0.1 | 35.8 ± 2.1 | 0.5 ± 0.2 | 31.0 ± 2.2 |
| DLPC:EYPC (100:25) | 2.1 ± 0.3 | 4.6 ± 1.2 | 2.3 ± 0.3 | 63.8 ± 1.0 | 2.3 ± 0.2 | 62.9 ± 2.8 |

Values represent the leakage (%), and ±identifies the standard deviation (SD).

TABLE 2

The membrane disruptive function promoting effect of adjuvant composition prepared from pH-sensitive compound of different kind

| | | | Complex with DLPC | | | |
|---|---|---|---|---|---|---|
| | Alone | | MPL: 0 | | MPL: 0.227 | |
| pH-sensitive substance | pH 7.4 | pH 5.0 | pH 7.4 | pH 5.0 | pH 7.4 | pH 5.0 |
| Cholic acid | 2.4 ± 0.1 | 9.8 ± 0.3 | 2.7 ± 0.3 | 34.5 ± 2.0 | 1.6 ± 0.3 | 34.1 ± 2.2 |
| Ursodeoxycholic acid | 3.6 ± 0.5 | 6.8 ± 0.3 | 1.4 ± 1.0 | 23.9 ± 2.5 | 2.2 ± 1.0 | 28.1 ± 2.8 |
| Chenodeoxycholic acid | 0.7 ± 0.5 | 14.1 ± 0.9 | 3.0 ± 1.4 | 52.8 ± 8.8 | 1.4 ± 0.1 | 48.5 ± 8.5 |
| Hyodeoxycholic acid | 4.2 ± 0.9 | 12.6 ± 0.4 | 2.1 ± 0.8 | 62.1 ± 8.3 | 2.2 ± 0.6 | 63.5 ± 6.4 |
| Glycodeoxycholic acid | 1.9 ± 1.2 | 9.8 ± 0.8 | 2.1 ± 0.2 | 36.3 ± 4.1 | 1.6 ± 0.3 | 35.4 ± 1.6 |
| Glycyrrhizinic acid | 4.2 ± 1.2 | 16.7 ± 2.9 | 1.8 ± 0.3 | 59.8 ± 3.3 | 1.3 ± 0.1 | 63.9 ± 6.8 |

Values represent the leakage (%), and ±identifies the standard deviation (SD).

First, all the pH-sensitive carriers (represented as MPL: 0 in the table) produced the membrane disruptive function promoting effect regardless of the kind of the amphipathic substances used and the kind of the pH-sensitive compounds used (Tables 1 and 2). Next, the MPL-containing adjuvant composition (represented as MPL: 0.227 in the table) produced, at both pH 7.4 and pH 5.0, the similar membrane disruptive function promoting effect as that of the MPL-free adjuvant composition (or the pH-sensitive carrier) which was prepared with either of the amphipathic substance and the pH-sensitive compound (Tables 1 and 2). These results suggest that the inclusion of MPL has no influence on the adjuvant composition's membrane disruptive function promoting effect regardless of the kind of the amphipathic substance used and the kind of the pH-sensitive compound used.

It was confirmed that the kind of the amphipathic substance or the kind of the pH-sensitive compound has no connection with the membrane disruptive function promoting effect which is produced by the inclusion of MPL.

It is considered from the foregoing discussions (7-1) to (7-4) that the adjuvant composition produces the membrane disruptive function promoting effect irrespective of the method for preparation, the amount of complex product, the amphipathic substance, and the pH-sensitive compound.

(8) Influence on the Membrane Fusion Function Promoting Effect

Figure 12:
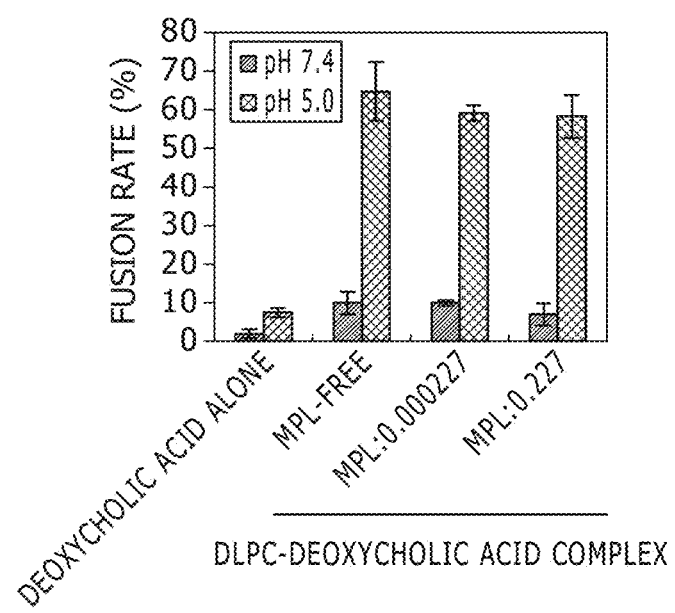
FIG. 12 depicts the result of examination for the influence of the MPL inclusion on the adjuvant composition's membrane fusion function promoting effect.

FIG. 12 depicts the result of an investigation made to examine the influence of the MPL inclusion on the adjuvant composition's membrane fusion function promoting effect. The amphipathic substance is DLPC, and the pH-sensitive compound is deoxycholic acid (160 nmol). The MPL content ranges from 0 to 0.227, and the adjuvant composition is prepared by the preparation method by dispersion. It is apparent from FIG. 12 that the MPL inclusion has no influence on the membrane-fusion promoting function.

(9) Influence on Stimulus to Activate Innate Immune System
(9-1) Influence of the Amount of Antigen An investigation was made to examine how the amount of antigen influences the stimulus to activate innate immune system in the case of the vaccine composition composed of the antigen and the adjuvant composition. The amphipathic substance is DLPC and the pH-sensitive compound is deoxycholic acid (160 nmol). Two kinds of the adjuvant compositions were used, one in which the MPL content is 0.0227 (referred to as "low MPL" hereinafter) and the other in which the MPL content is 22.7 (referred to as "high MPL" hereinafter). The vaccine composition was prepared by the preparation method by dispersion.

Figure 13B:
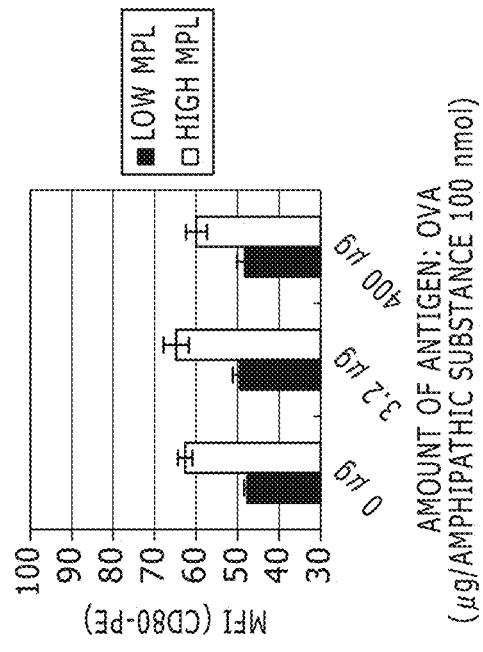
FIGS. 13(A)-13(B) depict the result of examination for the influence of the antigen amount on the vaccine composition's ability to activate innate immune system.
Figure 13A:
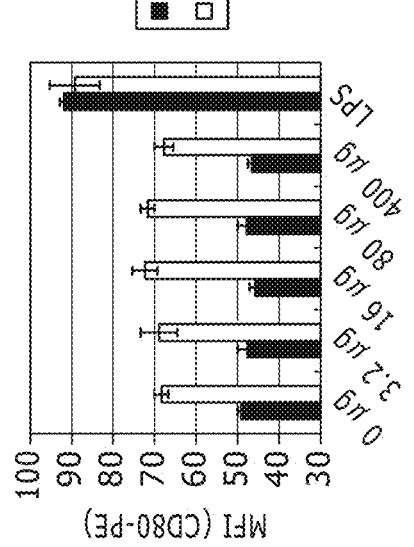

The results are depicted in FIGS. 13(A) and 13(B). FIG. 13(A) depicts the fluorescence intensity of CD80PE which was observed in the case where the vaccine composition containing peptide in varied amounts was added to the cultured mice spleen cells. FIG. 13(B) depicts the fluorescence intensity of CD80PE which was observed in the case where the vaccine composition containing OVA protein (simply referred to as "OVA" hereinafter) in varied amounts was added to the cultured mice spleen cells.

In both low MPL and high MPL, the fluorescence intensity of CD80PE remained constant regardless of the amount of OVA (FIGS. 13(A) and 13(B)). This suggests that the amount of the antigen does not influence the strength of stimulus to activate innate immune system.

(9-2) Influence of the Kind of Amphipathic Substance

Figure 14:
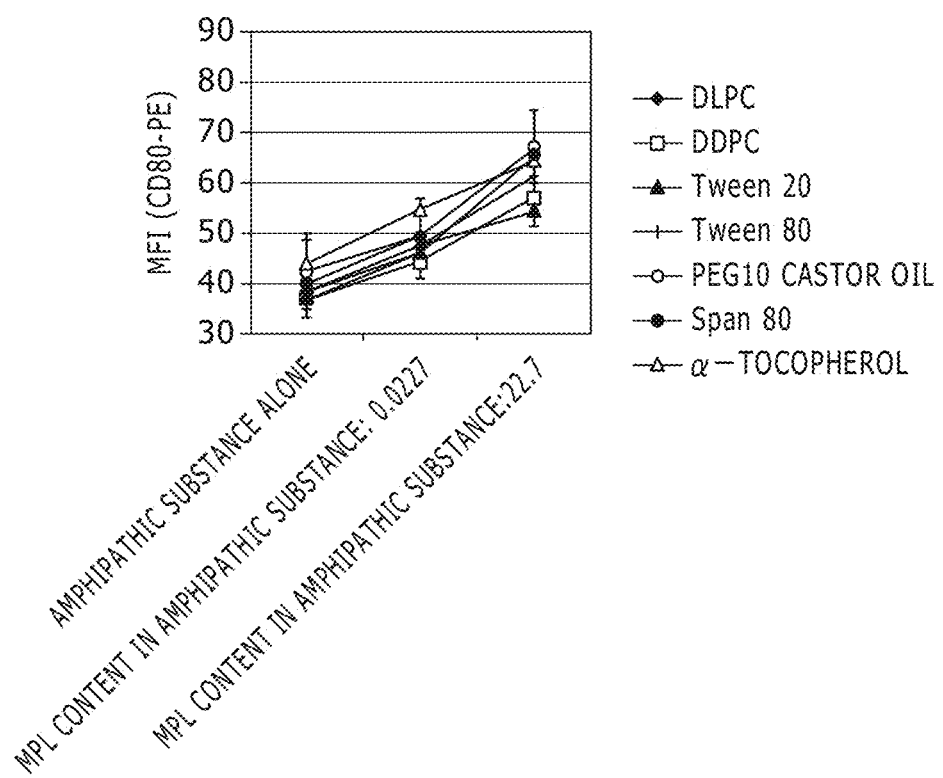
FIG. 14 depicts the result of examination for the influence of the amphipathic substance on the adjuvant composition's stimulus to activate innate immune system.

An investigation was made to examine how the amphipathic substance influences the adjuvant composition's stimulus to activate innate immune system. Table 3 and FIG. 14 depicts the result of the investigation in which the adjuvant composition was prepared from a variety of amphipathic substances. The pH-sensitive compound is deoxycholic acid (160 nmol) and the MPL content ranges from 0.0227 to 22.7. The preparation method by dispersion was employed for sample preparation.

TABLE 3

Influence of amphipathic substance on stimulus to activate innate immune system

| | CD80 MFI | | |
|---|---|---|---|
| Amphipathic substance | Amphipathic substance | MPL content: 0.0227 | MPL content: 22.7 |
| DLPC | 38.5 ± 2.9 | 44.3 ± 0.7 | 65.5 ± 2.6 |
| DDPC | 36.5 ± 1.1 | 43.8 ± 3.1 | 57.0 ± 2.7 |
| Tween 20 | 38.0 ± 3.2 | 46.8 ± 2.9 | 54.8 ± 4.0 |
| Tween 80 | 36.0 ± 3.2 | 45.6 ± 2.7 | 60.9 ± 3.5 |
| Peg10 castor oil | 42.1 ± 2.9 | 48.9 ± 4.6 | 67.0 ± 9.2 |
| Span 80 | 39.6 ± 1.8 | 48.8 ± 4.7 | 65.9 ± 4.4 |
| α-Tocopherol | 43.8 ± 4.9 | 54.7 ± 1.8 | 64.0 ± 4.8 |

Values represent the MFI (fluorescence intensity) (%), and ±identifies the standard deviation (SD).

The adjuvant composition containing the amphipathic substance, no matter what their kind might be, gave a higher fluorescence intensity of CD80PE than that containing the amphipathic substance alone. This implies the addition of stimulus to activate innate immune system (Table 3 and FIG. 14). This result suggests that the adjuvant composition functions satisfactorily irrespective of the kind of the amphipathic substance used.

(9-3) Influence of Amount of Complex Product of pH-Sensitive Compound

FIGS. 15(A)-(B) depict the results of an investigation to examine how the complex product of the pH-sensitive compound influences the strength of the adjuvant composition's and the vaccine composition's stimulus to activate innate immune system. The amphipathic substance is DLPC, the pH-sensitive compound is deoxycholic acid, and MPL content is 0.0227 or 22.7, and the amount of the antigen is 0 µg (in the adjuvant composition) and 400 µg (in the vaccine composition). All the samples were prepared by dispersion. Evaluation was performed by using dispersion (5 µL).

FIG. 15(A) depicts the fluorescence intensity of CD80PE which is observed in the case where the MPL content is 0.0227 and DLPC is complexed with deoxycholic acid in varied amounts. FIG. 15(B) depicts the fluorescence intensity of CD80PE which is observed in the case where the MPL content is 22.7 and DLPC is complexed with deoxycholic acid in varied amounts.

In the case where the MPL content is 0.0227 and 22.7, the fluorescence intensity of CD80PE remained constant regardless of the complexing of the deoxycholic acid and the amount of the complex product. This indicates that the complexing of the deoxycholic acid does not influence the adjuvant composition's and the vaccine composition's stimulus to activate innate immune system (FIGS. 15(A) and 15(B)).

(9-4) Influence of the Kind of pH-Sensitive Compound

Figure 16B:
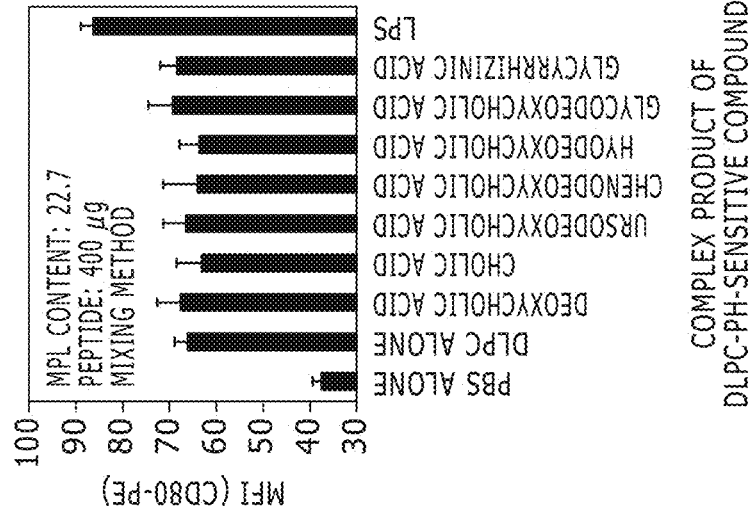
FIGS. 16(A)-16(B) depict the result of examination for the influence of the pH-sensitive compound varying in kind on the strength of the vaccine composition's stimulus to activate innate immune system.
Figure 16A:
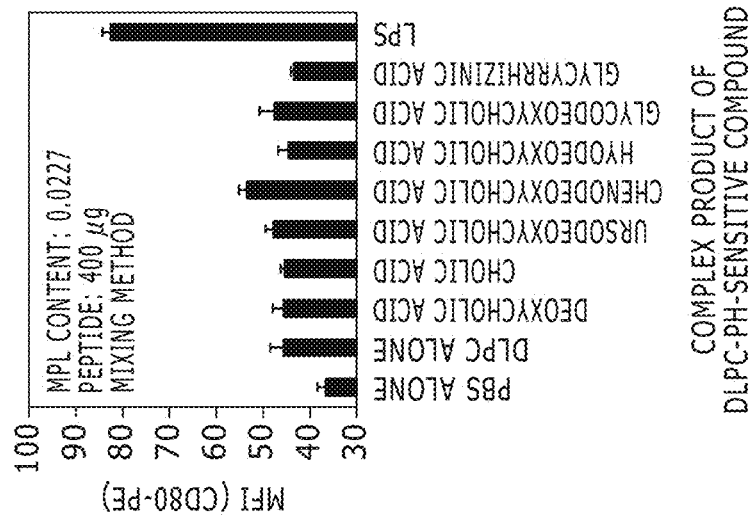

FIGS. 16(A) and 16(B) depicts the result of an investigation to examine the influence of the kind of the pH-sensitive compound on the strength of the vaccine composition's stimulus to activate innate immune system. FIGS. 16(A) and 16(B) depict the fluorescence intensity of CD80 in the case where the pH-sensitive compound of different kinds was added to the cultured mice spleen cells. The amphipathic substance used is DLPC, and the amount of complex product of the pH-sensitive compound is 160 nmol. The MPL content is 0.0227 and 22.7, and the antigen is peptide (400 µg). The preparation method by mixing was used for preparation.

It is noted that the fluorescence intensity of CD80PE for all the pH-sensitive compounds is higher than in the case of the antigen and PBS (PBS alone in the figure), and that the stimulus to activate innate immune system was added. This suggests that the stimulus to activate innate immune system is not influenced by the kind of the pH-sensitive compound used (FIGS. 16(A) and 16(B)).

It is considered from (9-1) to (9-4) above that the adjuvant composition functions satisfactorily independently of the amount of antigen, the amphipathic substance, the complex product, and the pH-sensitive compound.

(10) Verification of Immune Response Induction (10-1) Influence of the Amount of MPL The adjuvant composition, in which the MPL content is 0.0227 (low MPL) or 22.7 (high MPL), was examined for the effect of enhancing the induction of CTL. The amphipathic substance is DLPC, and the pH-sensitive compound is deoxycholic acid (160 nmol). The antigen is OVA peptide in an amount of 3.2 µg to 400 µg per head. The vaccine composition was subcutaneously administered once to the back of C57BL/6N mice. The preparation method by dispersion was used. For each group, n=3. The results are depicted in Table 4 below. "MPL alone" depicts the results in the case where the antigen and the MPL dispersion were used.

TABLE 4

Verification of effect of enhancing CTL induction in the case of low MPL and high MPL

| Amount of antigen (µg) | Low MPL | | High MPL | |
|---|---|---|---|---|
| | MPL alone | Adjuvant composition | MPL alone | Adjuvant composition |
| 3.2 | 0.14 | 0.57 | 0.45 | 1.11 |
| 16 | 0.31 | 0.66 | 0.36 | 1.00 |
| 80 | 0.26 | 0.74 | 0.37 | 2.61 |
| 400 | 0.46 | 0.50 | 0.58 | 2.10 |

Amphipathic substance: DLPC pH-sensitive compound: deoxycholic acid (160 nmol)

MPL content: low MPL (0.0227), high MPL (22.7)

Antigen: peptide in an amount of 3.2 to 400 µg

Method of preparation: preparation method by dispersion

Each group: n=3 (evaluation was made for three heads altogether)

Figure 17A:
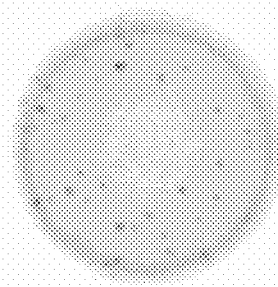
FIGS. 17(A)-17(B) depict the result of evaluation by ELIspot method in the case where the vaccine composition is used.
Figure 17B:
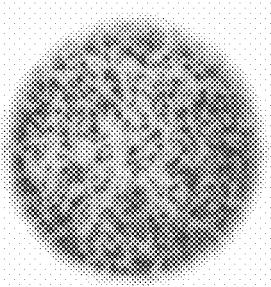

The result in each experiment with the antigen in a fixed amount depicts that the adjuvant composition with either a high MPL content or a low MPL content gave a higher CTL induction rate than that containing MPL alone (Table 4). It was depicted that the adjuvant composition produces the effect of enhancing the induction of CTL under the above-mentioned conditions. FIGS. 17(A) and 17(B) depict the results of evaluation by ELIspot method in the case where the vaccine composition was used. The antigen used is OVA (80 µg). FIG. 17(A) depicts the spot formation in the case where the peptide and the MPL dispersion (MPL alone) were used under the condition of high MPL. FIG. 17(B) depicts the spot formation in the case where the vaccine composition composed of the peptide and the adjuvant composition was used under the condition of high MPL. The condition for evaluation is 1×10⁶ cells/well.

Evaluation by ELIspot method also supports the foregoing result by the fact that the adjuvant composition induces more IFNγ-related spots than MPL used alone (FIGS. 17(A) and 17(B)).

(10-2) Influence of Amount of Complex Product of pH-Sensitive Compound

An investigation was made as to the influence of the amount of complex product of the pH-sensitive compound on the adjuvant composition's effect of enhancing the induction of CTL. To be more specific, the adjuvant composition was prepared in which the DLPC is complexed with deoxycholic acid in varied amounts, and the resulting adjuvant composition was examined for the effect of enhancing the induction of CTL. The content of MPL is 0.227. The vaccine composition containing peptide (80 µg) or OVA (80 µg) as the antigen was subcutaneously administered to C57BL/6N mice. It was prepared by the preparation method by dispersion. For each group, n=1. The results are depicted in Table 5.

TABLE 5

Effect of enhancing CTL induction that varies depending on amount of complex product

| Amount of complex product of | CTL induction rate by adjuvant composition (%) | |
| --- | --- | --- |
| deoxycholic acid | Antigen: peptide | Antigen: OVA |
| MPL alone | 0.22 | 0.18 |
| Deoxycholic acid: 10 | 0.38 | 0.37 |
| Deoxycholic acid: 20 | 0.44 | 0.42 |
| Deoxycholic acid: 160 | 0.68 | 0.66 |
| Deoxycholic acid: 640 | 0.40 | 0.57 |

Amphipathic substance: DLPC
pH-sensitive compound: deoxycholic acid (10 to 640 nmol)
MPL content: 0.227
Antigen: peptide (80 μg) or OVA (80 μg)
Method of preparation: preparation method by dispersion
Each group: n=1

The CTL induction rate in the case where the adjuvant composition with peptide or
OVA was used is higher than that in the case where MPL was used alone (antigen and MPL dispersion) regardless of the amount of complex product (Table 5). It was depicted that the effect of enhancing the induction of CTL is produced in the case where the pH-sensitive compound (10 to 640 nmol) is used for the amphipathic substance (100 nmol).

(10-3) Influence Attributable to the Kind of Amphipathic Substances or pH-Sensitive Compounds Next, an investigation was made as to how the adjuvant composition's effect of enhancing the induction of CTL varies depending on the kind of the amphipathic substance and the kind of the pH-sensitive compound. To be concrete, samples of the adjuvant composition were prepared from various amphipathic substances or pH-sensitive compounds, and they were examined for the presence or absence of the effect of enhancing the induction of CTL.

In this investigation, the content of MPL is 0.227 and the antigen is OVA (80 μg). The amount of complex product of the pH-sensitive compound is 160 nmol. The preparation method by dispersion was employed. For each group, n=1.

Table 6 depicts the results obtained in the case where the adjuvant composition was prepared from various amphipathic substances. Table 7 depicts the results obtained in the case where the adjuvant composition was prepared from various pH-sensitive compounds.

TABLE 6

Effect of enhancing CTL induction by adjuvant composition in the case where various kinds of amphipathic substance are used

| | CTL induction rate (%) | |
| --- | --- | --- |
| | Amphipathic substance-MPL | Adjuvant composition |
| No treatment | 0.11 | — |
| MPL alone | 0.20 | — |
| DLPC | 0.23 | 0.62 |
| DDPC | 0.19 | 0.27 |
| Tween 20 | 0.20 | 0.54 |
| Tween 80 | 0.23 | 0.37 |
| Peg 10 castor oil | 0.16 | 0.32 |

TABLE 6-continued

Effect of enhancing CTL induction by adjuvant composition in the case where various kinds of amphipathic substance are used

| | CTL induction rate (%) | |
| --- | --- | --- |
| | Amphipathic substance-MPL | Adjuvant composition |
| Span 80 | 0.23 | 0.40 |
| α-tocopherol | 0.31 | 0.50 |

Amphipathic substance: 100 nmol each
pH-sensitive compound: deoxycholic acid (160 nmol)
MPL content: 0.227
Antigen: OVA (80 μg)
Method of preparation: preparation method by dispersion
Each group: n=1
Amphipathic substance—MPL: Prepared by dispersing a mixed thin film of amphipathic substance and MPL in an antigen solution

TABLE 7

Effect of enhancing CTL induction by adjuvant composition and antigen specificity due to adjuvant composition in the case where various kinds of pH-sensitive compound are used

| | CTL induction rate (%) | |
| --- | --- | --- |
| | Adjuvant composition | Adjuvant composition (with antigen not restimulated) |
| No treatment | 0.17 | 0.15 |
| MPL alone | 0.25 | 0.14 |
| Cholic acid | 0.43 | 0.21 |
| Ursodeoxycholic acid | 0.55 | 0.14 |
| Chenodeoxycholic acid | 0.50 | 0.20 |
| Hyodeoxycholic acid | 0.51 | 0.10 |
| Glycodeoxycholic acid | 0.35 | 0.09 |
| Glycyrrhizinic acid | 0.57 | 0.12 |

Amphipathic substance: DLPC
pH-sensitive compound: 160 nmol each
MPL content: 0.227
Antigen: OVA (80 μg)
Method of preparation: preparation method by dispersion
Each group: n=1

The adjuvant composition prepared from the amphipathic substance of any kind and the pH-sensitive compound of any kind gave a higher CTL induction rate than that of the adjuvant composition prepared from MPL alone. This indicates that the adjuvant composition produces the effect of enhancing the induction of CTL (Tables 6 and 7).

Also, FIGS. 18(A)-(E) depict the results of evaluation by ELIspot method for the vaccine composition in which the pH-sensitive compound was varied. The condition for evaluation is $2 \times 10^6$ cells/well, and the antigen used was OVA (80 μg). The MPL content is 0.227. FIG. 18 depicts spots which differ in appearance depending on the substance to stimulate innate immune system or the adjuvant composition. FIG. 18(A) depicts spots observed when the MPL dispersion was used. FIG. 18(B) depicts spots observed when the MPL-containing DLPC-deoxycholic acid was used. FIG. 18(C) depicts spots observed when the MPL-containing DLPC-cholic acid was used. FIG. 18(D) depicts spots observed when the MPL-containing DLPC-ursodeoxycholic acid was used. FIG. 18(E) depicts spots observed when the MPL-containing DLPC-hyodeoxycholic acid was used.

The adjuvant composition prepared from any one of the pH-sensitive compound induces more IFNγ-related spots than that prepared from MPL alone. This suggests that the adjuvant composition prepared from whatever pH-sensitive compound produces the effect of enhancing the induction of CTL (FIGS. 18(A)-18(E)). These results coincide with those obtained when the ICS method is employed.

(11) Regarding Method for Preparation

Figure 19:
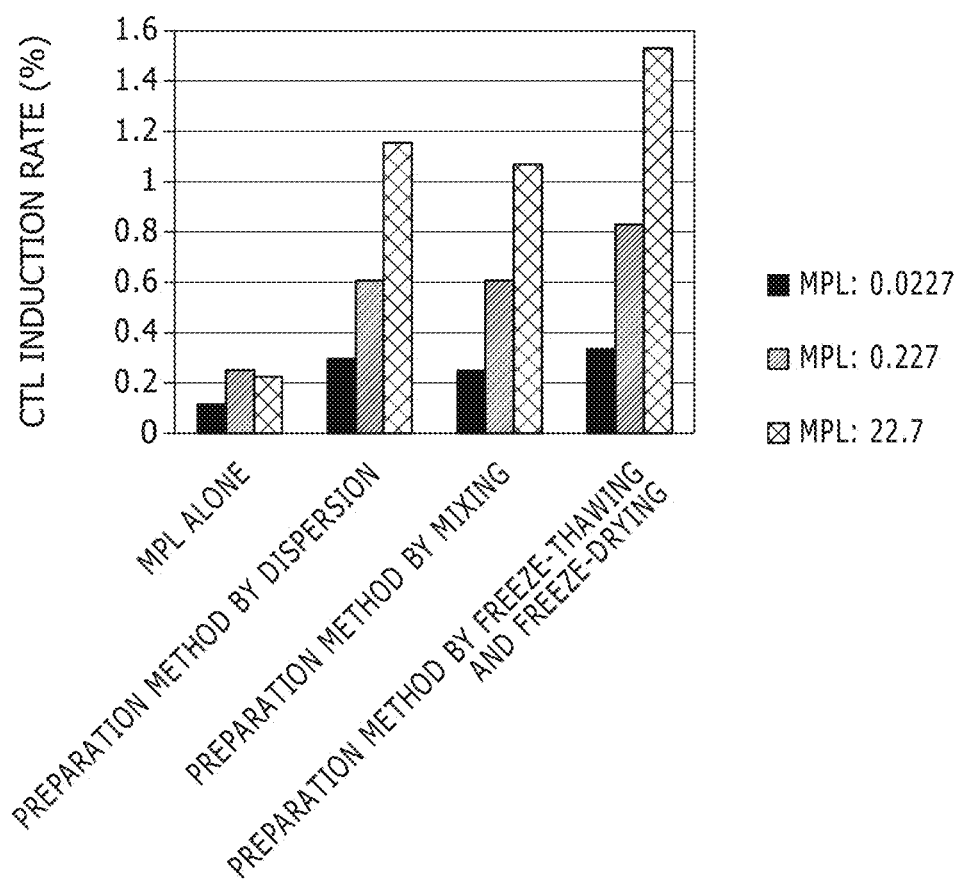
FIG. 19 is a graph depicting the CTL induction rate of the vaccine composition prepared by various preparation methods.

An investigation was made to examine how the vaccine composition varies depending on the method of preparation in the case where protein is used. FIG. 19 is a graph depicting the CTL induction rate due to various vaccine compositions prepared by different methods. The vaccine compositions were prepared by dispersion, by mixing, and by freeze-thawing and freeze-drying. The amphipathic substance is DLPC and the pH-sensitive compound is deoxycholic acid (160 nmol). The content of MPL is 0.0227 to 22.7. The antigen is OVA (80 µg). For each group, n=1.

It is noted from FIG. 19 that the vaccine composition, regardless of its method of preparation, gave a higher CTL induction rate that that prepared from MPL alone. Particularly, preparation by freeze-thawing and freeze-drying gave a high CTL induction rate. These results suggest that no matter how the vaccine composition may be prepared, the adjuvant composition produces the effect of enhancing the induction of CTL (FIG. 19). Even in the case where protein is used as the antigen, the vaccine composition prepared by freeze-thawing and freeze-drying gave a higher CTL induction rate than those prepared by other methods (FIG. 19).

(12) Regarding Antigen Specificity

An investigation was made to confirm whether or not the CTL induced by the vaccine composition has antigen specificity. To be concrete, this object was achieved by checking the difference in the CTL induction rate between two methods of cell culture. Culture by the first method involves OVA peptide as an antigen added to the suspension of mice spleen cells (with restimulation); and culture by the second method relies on a medium alone containing no OVA peptide (without restimulation). The vaccine composition contains DLPC as the amphipathic substance and deoxycholic acid (160 nmol) as the pH-sensitive compound. The content of MPL is 22.7. OVA (80 µg) was administered to C57BL/6N mice. The dispersion of the vaccine composition was prepared by preparation method by mixing. For each group, n=1.

Figure 20A:
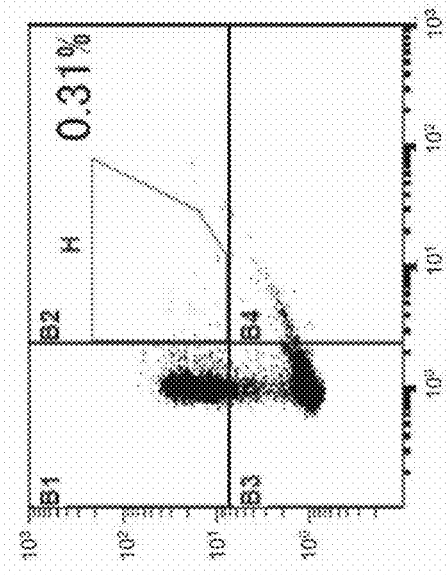
FIGS. 20(A)-20(B) depict the result of evaluation for the antigen specificity of the CTL induced by the vaccine composition.
Figure 20B:
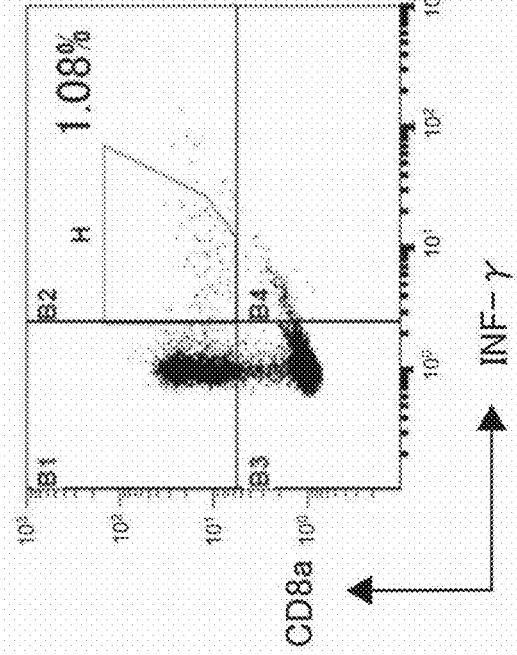

The results obtained are depicted in FIGS. 20(A) and 20(B). FIG. 20(A) depicts the CTL induction rate in the case of culture with restimulation. FIG. 20(B) depicts the CTL induction rate in the case of culture without restimulation. In the case with restimulation, the CTL induction rate is 1.08%, (this value suggests the presence of CTL induction); in the case without restimulation, the CTL induction rate is 0.31%, (this value is smaller than that in the case with restimulation of the antigen) (FIGS. 20A and 20B) Similar results were observed also in the case where various pH-sensitive compounds were used (Table 7). The foregoing results suggest that the CTL induced by the vaccine composition is antigen-specific.

An additional investigation was made to confirm antigen specificity by the ELIspot method. The vaccine composition contains DLPC as the amphipathic substance and deoxycholic acid (160 nmol and 640 nmol) as the pH-sensitive compound. The MPL content is 0.227. OVA (80 µg) or peptide (80 µg) was administered to a C57BNL/6N mice. The dispersion of the vaccine composition was prepared by preparation method by dispersion. Evaluation was performed under the condition of 2×10⁶ cells/well.

The results obtained are depicted in FIG. 21. FIGS. 21(A)-21(F) depict spot formation in culture with OVA peptide as antigen (with restimulation). FIGS. 21(G)-21(L) depict spot formation in culture with medium alone (without restimulation). In the case where the vaccine composition was used, spot formation without restimulation is much less insignificant than spot formation with restimulation. This indicates that the CTL induced by the vaccine composition has antigen specificity. The result obtained by ELIspot method was also similar to that obtained by ICS method.

(13) Regarding Enhancement of Humoral Immunity

An investigation was made to verify the induction of humoral immunity by the vaccine composition and the effect of enhancing the induction of humoral immunity by the adjuvant composition. To be concrete, in this investigation, one of the vaccine compositions prepared by various methods was subcutaneously administered twice into the back of C57BL/6N mice, and the IgG antibody titer in blood was measured. The amphipathic substance is DLPC, and the pH-sensitive compound is deoxycholic acid (160 nmol). The content of MPL is 0.227 and the antigen is OVA (80 µg). For comparison, one group was not given the antigen and one group was given the antigen-containing MPL alone. For each group, n=3.

Figure 22:
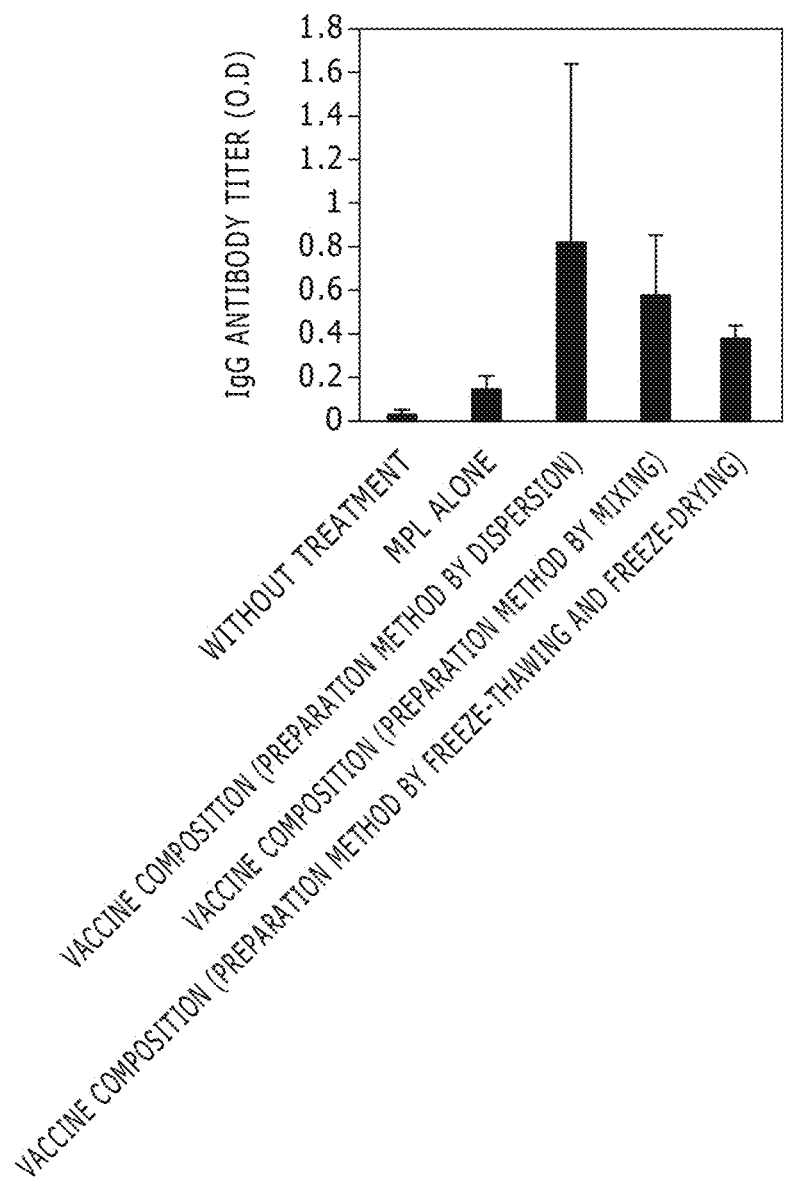
FIG. 22 is a graph depicting the IgG antibody titer in the case where the vaccine compositions prepared by various preparation methods are used.

The results obtained are depicted in FIG. 22. The subject which was given the vaccine composition depicted a higher IgG antibody titer than the untreated subject regardless of the method (by dispersion, by mixing, and by freeze-thawing and freeze-drying) by which the vaccine composition was prepared. This apparently suggests that the vaccine composition induced humoral immunity (FIG. 22).

The antibody titer is higher in the case of the vaccine compositions (each composed of the antigen and the adjuvant composition), regardless of the method of their preparation, than that containing MPL alone (or composed of antigen and MPL dispersion) (FIG. 22). The fact that the vaccine composition containing the adjuvant composition gives a higher antibody titer than that containing MPL alone suggests that the adjuvant composition produces the effect of enhancing the induction of humoral immunity (FIG. 22).

(14) Regarding Adjuvant Composition Containing CpG-DNA

An investigation was made to verify the adjuvant composition's effect of enhancing the induction of CTL in the case where CpG-DNA (or CpG-ODN) is used as the substance (other than MPL) to activate innate immune system. To be concrete, the adjuvant composition was prepared from a mixture of CpG-ODN (5 µg per head) and DLPC-deoxycholic acid complex, and this adjuvant composition was mixed with OVA (80 µg) to give the desired vaccine composition. The amount of deoxycholic acid is 160 nmol and the total amount of the vaccine composition is 100 µL. This vaccine composition was administered to C57BL/6N mice (one head per group). Evaluation by ELIspot method was performed under the condition of 2×10⁶ cells/well.

Table 8 depicts the CTL induction rate in the case where the restimulation of antigen was given or not given. These results were obtained when the antigen and CpG-ODN (CpG-ODN alone) were administered or the adjuvant composition containing CpG-ODN (vaccine composition) was administered. In the case where the adjuvant composition containing CpG-ODN is used, the CTL induction rate is higher than in the case of CpG-ODN alone (Table 8). It was found that even in the case where the substance other than MPL which activates innate immune system is used, the adjuvant composition produces the effect of enhancing CTL induction. The CTL induction rate in the absence of restimulation is lower than that in the presence of restimulation. This apparently suggests that the CTL induced by the vaccine composition containing CpG-ODN is antigen specific as in the case of MPL (Table 8). The same result as above was obtained in evaluation by ELIspot method (FIGS. 23(A)-(D)).

FIG. 23(A) depicts spot formation resulting from administration of OVA (80 μg) and CpG-ODN alone. FIG. 23(B) depicts spot formation resulting from administration of OVA (80 μg) and the adjuvant composition containing CpG-ODN. FIG. 23(C) depicts spot formation resulting from administration of OVA (80 μg) and CpG-ODN alone, without restimulation of the antigen. FIG. 23(D) depicts spot formation resulting from administration of OVA (80 μg) and the adjuvant containing CpG-ODN, without restimulation of the antigen.

TABLE 8

Effect of enhancing CTL induction by adjuvant composition containing CpG-DNA, and antigen specificity

| | CTL induction rate (%) | |
| --- | --- | --- |
| | With restimulation | Without restimulation |
| CpG-ODN alone | 0.27 | 0.12 |
| Adjuvant composition (CpG-ODN) | 0.80 | 0.09 |

Amphipathic substance: DLPC
pH-sensitive compound: deoxycholic acid (160 nmol)
CpG-ODN: 5 μg
Antigen: OVA (80 μg)
Each group: n=1

Having described several embodiments of the present disclosure which represent examples of the adjuvant composition, the vaccine composition containing the adjuvant composition and methods of making the same, it is to be understood that the disclosure is not limited to those precise embodiments and that various chanes and modications could be effected therein by those skilled in the art without departing form the spirit or scope of the disclosure as defined in the appended claims. It is expressly intended that all such changes, modifications and equivalents which fall within the scope of the claims are embraced by the claims.

What is claimed is:

1. An adjuvant composition comprising a pH-sensitive carrier and a substance with stimulus to activate innate immune system,
    wherein the pH-sensitive carrier comprises a pH-sensitive compound and an amphipathic sub stance,
    wherein the pH-sensitive compound is selected from the group consisting of deoxycholic acid, cholic acid, ursodeoxycholic acid, chenodeoxycholic acid, hyodeoxycholic acid, bile acid, glycodeoxycholic acid, glycyrrhizinic acid, and glycyrrhetinic acid, and salts thereof,
    wherein the amphipathic substance is selected from the group consisting of phosphatidylcholine having a fatty acid moiety of 10 to 12 carbon atoms wherein said fatty acid constitutes a hydrophobic moiety of the amphipathic substance, sorbitan fatty acid ester having a fatty acid moiety of 16 to 18 atoms wherein said fatty acid constitutes a hydrophobic moiety of the amphipathic substance, glycerol monooleate, glycerol dilaurate, glycerol distearate, glycerol dioleate, and polyoxyethylene castor oil,
    wherein the substance with stimulus to activate innate immune system is monophosphoryl lipid A.

2. An adjuvant composition comprising a pH-sensitive carrier and a substance with stimulus to activate innate immune system, wherein the pH-sensitive carrier comprises:
    at least one species of pH-sensitive compound; and
    at least one species of amphipathic substance, and
    produces the membrane disruptive function promoting effect,
    the pH-sensitive compound being selected from the group consisting of deoxycholic acid, cholic acid, ursodeoxycholic acid, chenodeoxycholic acid, hyodeoxycholic acid, bile acid, glycodeoxycholic acid, glycyrrhizinic acid, and glycyrrhetinic acid, and salts thereof;
    the amphipathic substance being selected from the group consisting of phosphatidylcholine having a fatty acid moiety of 10 to 12 carbon atoms wherein said fatty acid constitutes a hydrophobic moiety of the amphipathic substance, sorbitan fatty acid ester having a fatty acid moiety of 16 to 18 carbon atoms wherein said fatty acid constitutes a hydrophobic moiety of the amphipathic substance, glycerol monooleate, glycerol dilaurate, glycerol distearate, glycerol dioleate, and polyoxyethylene castor oil,
    wherein the substance with stimulus to activate innate immune system is monophosphoryl lipid A.

3. The adjuvant composition according to claim 1, comprising the substance with stimulus to activate innate immune system in an amount of 0.0227 to 22.7 mol for 100 mol of the amphipathic substance.

4. A method for producing an adjuvant composition, comprising:
    associating
        at least one species of pH-sensitive compound,
        at least one species of amphipathic substance, and
        a substance with stimulus to activate innate immune system;
    the pH-sensitive compound being selected from the group consisting of deoxycholic acid, cholic acid, ursodeoxycholic acid, chenodeoxycholic acid, hyodeoxycholic acid, bile acid, glycodeoxycholic acid, glycyrrhizinic acid, and glycyrrhetinic acid, and salts thereof;
        the amphipathic substance being selected from the group consisting of phosphatidylcholine having a fatty acid moiety of 10 to 12 carbon atoms wherein said fatty acid constitutes a hydrophobic moiety of the amphipathic substance, sorbitan fatty acid ester having a fatty acid moiety of 16 to 18 carbon atoms wherein said fatty acid constitutes a hydrophobic moiety of the amphipathic substance, glycerol monooleate, glycerol dilaurate, glycerol distearate, glycerol dioleate, and polyoxyethylene castor oil,
    wherein the substance with stimulus to activate innate immune system is monophosphoryl lipid A.

5. The adjuvant composition according to claim 1, having 10 mol or more of the pH-sensitive compound for 100 mol of the amphipathic substance.

6. The adjuvant composition according to claim 1, having 10 mol to 640 mol of the pH-sensitive compound for 100 mol of the amphipathic substance.

7. The adjuvant composition according to claim 1, wherein the amphipathic substance is selected from the group consisting of dilauroyl phosphatidylcholine, didecanoyl phosphatidylcholine, sorbitan monooleate, and polyoxyethylene castor oil.

8. The adjuvant composition according to claim 1, wherein the pH-sensitive compound is selected from the group consisting of deoxycholic acid, ursodeoxycholic acid, and glycyrrhizinic acid, and salts thereof.

9. The adjuvant composition according to claim 1, wherein the pH-sensitive compound and the amphipathic substance form micelle particles having a diameter of 10 to 200 nm.

10. The adjuvant composition according to claim 1, comprising an aqueous solvent.

11. The method according to claim 4, wherein the pH sensitive compound is selected from the group consisting of deoxycholic acid, ursodeoxycholic acid, and glycyrrhizinic acid, and salts thereof.

* * * * *